US011192109B2

United States Patent
Ben-Yakar et al.

(10) Patent No.: US 11,192,109 B2
(45) Date of Patent: Dec. 7, 2021

(54) MICROFLUIDIC DEVICES FOR THE RAPID AND AUTOMATED PROCESSING OF SAMPLE POPULATIONS

(71) Applicant: BOARD OF REGENTS, THE UNIVERSITY OF TEXAS SYSTEM, Austin, TX (US)

(72) Inventors: Adela Ben-Yakar, Austin, TX (US); Navid Ghorashian, Sunnyvale, CA (US); Sertan Kutal Gökçe, Austin, TX (US); Sam Xun Guo, Katy, TX (US); William Neil Everett, Cedar Park, TX (US); Frederic Bourgeois, Lynn, MA (US)

(73) Assignee: Board of Regents, The University of Texas System, Austin, TX (US)

( * ) Notice: Subject to any disclaimer, the term of this patent is extended or adjusted under 35 U.S.C. 154(b) by 265 days.

(21) Appl. No.: 16/038,415

(22) Filed: Jul. 18, 2018

(65) Prior Publication Data
US 2019/0232288 A1    Aug. 1, 2019

Related U.S. Application Data

(62) Division of application No. 14/772,156, filed as application No. PCT/US2014/020679 on Mar. 5, 2014, now Pat. No. 10,052,631.
(Continued)

(51) Int. Cl.
*B01L 3/00*         (2006.01)
*G01N 33/483*      (2006.01)

(52) U.S. Cl.
CPC ... *B01L 3/502761* (2013.01); *B01L 3/502715* (2013.01); *B01L 3/502738* (2013.01);
(Continued)

(58) Field of Classification Search
CPC .... B01L 3/502761; B01L 3/5027; B01L 3/00; G01N 35/00; G01N 33/48
See application file for complete search history.

(56) References Cited

U.S. PATENT DOCUMENTS

| | | |
|---|---|---|
| 6,432,290 B1 | 8/2002 | Harrison |
| 6,748,975 B2 | 6/2004 | Hartshorne et al. |
| (Continued) | | |

FOREIGN PATENT DOCUMENTS

| | | |
|---|---|---|
| EP | 2486979 A2 | 8/2012 |
| WO | 2009039284 A1 | 3/2009 |

OTHER PUBLICATIONS

Non-Final Office Action filed in U.S. Application No. 14/772,156, dated Dec. 28, 2017.
(Continued)

*Primary Examiner* — Brian J. Sines
(74) *Attorney, Agent, or Firm* — Meunier Carlin & Curfman LLC

(57) ABSTRACT

Microfluidic devices for the rapid and automated processing of sample populations are provided. Described are multiplexer microfluidic devices configured to serially deliver a plurality of distinct sample populations to a sample processing element rapidly and automatically, without cross-contaminating the distinct sample populations. Also provided are microfluidic sample processing elements that can be used to rapidly and automatically manipulate and/or interrogate members of a sample population. The microfluidic devices can be used to improve the throughput and quality of experiments involving model organisms, such as *C. elegans*.

18 Claims, 30 Drawing Sheets

Related U.S. Application Data

(60) Provisional application No. 61/772,899, filed on Mar. 5, 2013, provisional application No. 61/907,837, filed on Nov. 22, 2013.

(52) U.S. Cl.
CPC .... *G01N 33/4833* (2013.01); *B01L 2200/027* (2013.01); *B01L 2200/0652* (2013.01); *B01L 2200/0668* (2013.01); *B01L 2300/0816* (2013.01); *B01L 2300/0861* (2013.01); *B01L 2300/0867* (2013.01); *B01L 2300/0877* (2013.01); *B01L 2400/0487* (2013.01); *B01L 2400/06* (2013.01); *B01L 2400/0655* (2013.01); *G01N 2333/43534* (2013.01)

(56) References Cited

U.S. PATENT DOCUMENTS

| | | |
|---|---|---|
| 6,767,194 B2 | 7/2004 | Jeon et al. |
| 7,143,785 B2 | 12/2006 | Maerkl et al. |
| 7,312,611 B1 | 12/2007 | Harrison |
| 7,359,548 B2 | 4/2008 | Douglass et al. |
| 7,892,496 B2 | 2/2011 | McAvoy et al. |
| 10,052,631 B2 * | 8/2018 | Ben-Yakar ........ B01L 3/502715 |
| 2002/0029814 A1 | 3/2002 | Unger et al. |
| 2002/0033939 A1 | 3/2002 | Hansen |
| 2002/0168278 A1 | 11/2002 | Jeon et al. |
| 2003/0217923 A1 | 11/2003 | Harrison |
| 2004/0086424 A1 | 5/2004 | Schembri |
| 2004/0086869 A1 | 5/2004 | Schembri |
| 2004/0094479 A9 | 5/2004 | Schulte et al. |
| 2004/0115731 A1 | 6/2004 | Hansen |
| 2006/0050376 A1 | 3/2006 | Houston et al. |
| 2006/0171846 A1 * | 8/2006 | Marr ................ G01N 21/05 422/82.11 |
| 2007/0237686 A1 | 10/2007 | Mathies et al. |
| 2007/0280857 A1 | 12/2007 | Maengseok et al. |
| 2009/0305901 A1 * | 12/2009 | Seemann ............... B01F 5/064 506/7 |
| 2009/0314970 A1 | 12/2009 | McAvoy et al. |
| 2010/0028928 A1 | 2/2010 | Levchenko et al. |
| 2010/0116343 A1 | 5/2010 | Weibel et al. |
| 2010/0154890 A1 | 6/2010 | Maerkl et al. |
| 2010/0263599 A1 | 10/2010 | Yanik et al. |
| 2011/0136252 A1 | 6/2011 | Tseng et al. |
| 2011/0151578 A1 | 6/2011 | Abate et al. |
| 2011/0212844 A1 | 9/2011 | Yanik et al. |
| 2012/0052568 A1 * | 3/2012 | Subramanian ....... C12N 5/0607 435/325 |
| 2012/0061305 A1 | 3/2012 | Quake et al. |
| 2013/0035257 A1 * | 2/2013 | Yu ..................... C12N 11/04 506/11 |

OTHER PUBLICATIONS

Astle, T., "Standards in robotics and instrumentation," J. of Biomolecular Screening, 1996, vol. 1, No. 4, pp. 163-168.
Unger, M.A, et al., "Monolithic microfabricated valves and pumps by multilayer soft lithography," Science, 2000, 288:5463, pp. 113-116.
Thorsen, T., et al., "Microfluidic large-scale integration", Science, 2002, 298:5593, pp. 580-584.
Chokshi, et al., "An automated microfluidic platform for calcium imaging of chemosensory neurons in Caenorhabditis elegans," Lab on a Chip, 2010, vol. 10, No. 20, p. 2758.
Hulme, et al., "Lifespan-on-a-chip: microfluidic chambers for performing lifelong observation of C. elegans," Lab on a Chip, 2010, vol. 10, No. 5, pp. 589-597.
Wang, et al., "Microfluidic worm-chip for in vivo analysis of neuronal activity upon dynamic chemical stimulations," Analytica Chimica Acta, Elsevier, Amsterdam, NL, 2011, vol. 701, No. 5, pp. 23-28.
Wen, et al., "Analysis of Caenorhabditis elegans in microfluidic devices," Science China Chemistry, SP Science China Press, 2012, vol. 55, No. 4, pp. 484-493.
International Search Report and Written Opinion, issued in connection with International Application No. PCT/US2014/020679, dated Dec. 10, 2014.
International Preliminary Report on Patentability, issued in connection with International Application No. PCT/US2014/020679, dated Sep. 8, 2015.
Chung, K., et al., "Automated on-chip rapid mircoscopy, phenotyping and sorting of C. elegans," Nature Methods, 2008, 5:7, pp. 637-643.
Rohde, C.B., et al., "Microfluidic system for on-chip high-throughput whole-animal sorting and screening at subcellular resolution," Proceedings of the National Academy of Sciences of the United States of America, 2007, 104:35, p. 13891.
Samara, C., et al., "Large-scale in vivo femtosecond laser neurosurgery screen reveals small-molecule enhancer of regeneration," Proceedings of the National Academy of Sciences of the United States of America, 2010, 107:43, p. 18342-18347.
Squiban, B., et al., "Quantitative and automated high-throughput genome-wide RNAi screens in C. elegans," J. Visualized Experiments, 2012, vol. 60.
Chronis, N., et al., "Microfluidics for in vivo imaging of neuronal and behavioral activity in Caenorhabditis elegans," Nature Methods, 2007, 4:9, pp. 727-731.
Chung, K., et al., "Automated high-throughput cell microsurgery on-chip," Lab on a chip, 2009, 9:19, pp. 2764-2766.
Cui, X., et al., "Lensless high-resolution on-chip optofluidic microscopes for Caenorhabditis elegans and cell imaging," Proceedings of the National Academy of Sciences of the United States of America, 2008,105:31, p. 10670-10675.
Gray, J.M., et al., "Oxygen sensation and social feeding mediated by a C. elegans guanylate cyclase homologue," Nature, 2004, 430, pp. 317-322.
Guo, S.X., et al., "Femtosecond laser nanoaxotomy lab-on-a-chip for in vivo nerve regeneration studies," Nature Methods, 2008, 5:6, pp. 531-533.
Han, M., "Advancing biology with a growing worm field," Developmental dynamics: an official publication of the American Association of Anatomists, 2010, 239:5, pp. 1263-1264.
Hardy, B.S., et al., "The deformation of flexible PDMS microchannels under a pressure driven flow," Lab on a chip, 2009, 9:7, pp. 935-938.
Johnson, T.E., et al., Proceedings of the National Academy of Sciences of the United States of America, 1982, 79, pp. 6603-6607.
Kim, N., et al., "Automated microfluidic compact disc (CD) cultivation system of Caenorhabditis elegans," Sensors and Actuators B: Chemical, 2007,122:2, pp. 511-518.
Nguyen, N.T., et al., Fundamentals and Applications of Microfluidics, 2002, p. 471, Artech House, Boston, MA.
Yanik, M.F., et al., "Neurosurgery: functional regeneration after laser axotomy," Nature, 2004, 432:7019, p. 822.
Vogel, A et al., "Mechanisms of femtosecond laser nanosurgery of cells and tissues," Applied Physics B: Lasers and Optics, 2005, 81:8, pp. 1015-1047.
Hilliard, M.A., et al., "In vivo imaging of C. elegans ASH neurons: cellular response and adaptation to chemical repellents," EMBO J., 2005,24, pp. 63-72.
Stirman, J.N., et al., "High-throughput study of synaptic transmission at the neuromuscular junction enabled by optogenetics and microfluidics," Journal of Neuroscience Methods, 2010, 191:1, pp. 90-93.
Wu, Z., et al., "Caenorhabditis elegans neuronal regeneration is influenced by life stage, ephrin signaling, and synaptic branching," Proc. Nat'l Acad. Sci, 2007, 104, p. 15132-15137.
Chokshi, et al., "CO2 and compressive immobilization of c.elegans on-chip," Lab on a Chip, 2008.
Avery, L., "The genetics of feeding in Caenorhabditis elegans," Genetics, Apr. 1993, 133:4, pp. 897-917.
Clark, et al., Development, 2003, 130, pp. 3781-3794, Cambridge, U.K.

(56) References Cited

OTHER PUBLICATIONS

Zeng, et al., "Sub-cellular precision on-chip small-animal immobilization, multi-photon imaging and femtosecond-laser manipulation," Lab on a Chip, 2008, 8:5, pp. 653-656.

Di Carlo, et al., "Equilibrium separation and filtration of particles using differential inertial focusing," Analytical Chemistry, 2008, 80:6, pp. 2204-2211.

Gonzalez, et al., "Digital image processing," 3rd ed., 2008, pp. xxii, 954, Pearson/Prentice Hall, Upper Saddle River, NJ.

Bovik, A.C., "Handbook of image and video processing," 2nd ed., 2005, pp. xvi, 1372, Elsevier/Academic Press Burlington, MA.

Bueno-Ibarra, et al., "Fast autofocus algorithm for automated microscopes," Optical Engineering, 2005, 44:6.

Sun, et al., "Autofocusing in computer microscopy: selecting the optimal focus algorithm," Microscopy Research and Technique, 2004, 65:3, pp. 139-149.

Ouyang, et al., "Overview of the development of a visual based automated bio-micromanipulation system," Mechatronics, 2007, 17:10, pp. 578-588.

Corke, et al., "Dynamic effects in visual closed-loop systems," IEEE Transactions on Robotics and Automation, 1996, 12:5, pp. 671-683.

Xu, et al., "Design, Fabrication, and Visual Servo Control of an XY Parallel Micromanipulator With Piezo-Actuation," IEEE Transactions on Automation Science and Engineering, 2009, 6:4, pp. 710-719.

Franklin, et al., "Feedback control of dynamic systems", 5th ed., 2006, pp. xvii, 910, Pearson Prentice Hall, Upper Saddle River, N.J.

Ghosh-Roy, et al., "Caenorhabditis elegans: A new model organism for studies of axon regeneration," Developmental Dynamics, 2010.

Crane, et al., "Computer-enhanced high-throughput genetic screens of C. elegans in a microfluidic system," Lab on a Chip, 2009, 9, pp. 38-40.

Chung, et al., "Automated laser ablation of neurons in microfluidic system," Lab on a Chip, 2009, 9, pp. 2764-2766.

Weaver, et al., "Static control logic for microfluidic devices using pressure-gain valves," Nature Physics, 2010, 6, pp. 218-223.

Gilleland, et al., "Microfluidic immobilization of physiologically active Caenorhabditis elegans," Nature Protocols, 2010, vol. 5, p. 1888.

Hulme, S.E., et al., "A microfabricated array of claims for immobilizing and imaging C. elegans," Lab on a chip, 2007, 7:11, pp. 1515-1523.

Wang, J., et al., "Integrated Microfluidics for Parallel Screening of an In Situ Click Chemistry Library," 2006, Angewandte Chemie, 118:32, pp. 5402-5407.

Rohde, et al., "Subcellular in vivo time-lapse imaging and optical manipulation of C. elegans in standard multiwell plates," Nat. Commun., 2011, 2:275.

Chen, et al., "Fast Convolution with Laplacian-of-Gaussian Masks," IEEE Transactions on Pattern Analysis and Machine Intelligence, 1987, 9:4, pp. 584-590.

\* cited by examiner

MICROFLUIDIC DEVICES FOR THE RAPID AND AUTOMATED PROCESSING OF SAMPLE POPULATIONS

CROSS-REFERENCE TO RELATED APPLICATIONS

This application claims benefit of U.S. Provisional Application Nos. 61/772,899, filed Mar. 5, 2013 and 61/907,837, filed Nov. 22, 2013, both of which are hereby incorporated herein by reference in their entirety.

STATEMENT REGARDING FEDERALLY SPONSORED RESEARCH OR DEVELOPMENT

This invention was made with Government Support under Grant No. R21 NS058646, R21 NS067340, R01 NS060129, and Grant No. R01 AG041135 awarded by the National Institutes of Health. The Government has certain rights in the invention.

FIELD OF THE DISCLOSURE

This invention relates generally to microfluidic devices for the rapid and automated processing of samples, including populations of organisms.

BACKGROUND

Model organisms are a powerful research tool in molecular biology. For example, *Caenorhabditis elegans* (*C. elegans*) has increasingly been employed by researchers to study various biological processes, including cellular differentiation, neural development and function, aging, reproduction, toxicology, and genetic function. *C. elegans* has attracted particular research interest due to its simple anatomy, highly conserved and fully sequenced genome, amenability to various biochemical experimental methods, and fully characterized cellular anatomy.

In order to perform many types of experiments with model organisms such as *C. elegans*, multiple distinct sample populations of the model organism must be manipulated and examined. In many cases, these experiments involve individually processing each organism in each sample population one or more times (e.g., to sequence each organism's genome, to surgically alter each organism, to microscopically evaluate each organism's anatomy, or to assess the response of each organism following a treatment). Results obtained for the organisms in each population can then be compared. In order to extract meaningful information from these types of experiments, cross-contamination between sample populations must be avoided.

Experimental throughput and accuracy could be greatly improved by developing platforms, which can rapidly and automatically process multiple unique populations of model organisms while maintaining segregation between the populations.

SUMMARY OF THE DISCLOSURE

Microfluidic devices for the rapid and automated processing of samples, including populations of organisms, are described. Also provided are methods of using these devices to rapidly and automatically process samples, including populations of organisms.

Provided is a multiplexer microfluidic device configured to facilitate the processing of sample populations. The multiplexer microfluidic device is configured to house and automatically deliver multiple unique sample populations to an outlet or sample processing element, such that the sample populations remain segregated from each other during delivery (i.e., during delivery, the members of each sample population are delivered to the outlet or sample processing element without substantially mixing members of one sample population with members of any other sample populations).

The multiplexer microfluidic device comprises a main channel, a plurality of sample reservoirs, and a plurality of inlet channels, each of which fluidly connects a single sample reservoir to the main channel. Where each inlet channel fluidly connects with the main channel, an intersection is formed. The multiplexer microfluidic device further comprises a plurality of valves positioned along the inlet channels to regulate fluid flow through the inlet channels. The plurality of valves in the multiplexer microfluidic device is configured such that operation of one or more of the plurality of valves selectively directs fluid flow through a predetermined inlet channel in the device. At least a first valve and a second valve are positioned along each fluid inlet channel to regulate fluid flow through the inlet channel. The first valve and the second valve are configured to be independently operable, meaning that the first valve and the second valve can be opened and closed independent of one another. The first valve is positioned in proximity to the intersection of the inlet channel and the main channel. The second valve is positioned upstream of the first valve (i.e., along the inlet channel between the sample reservoir and the first valve).

The downstream end of the main channel of the multiplexer microfluidic device can be fluidly connected to a sample processing element. The sample processing element can be configured to characterize and/or manipulate the sample populations delivered by the multiplexer, the individuals in each sample population delivered by the multiplexer, or combinations thereof. For example, the sample processing element can be a device for optically manipulating the individuals in a sample population (e.g., a device for performing laser surgery on an organism), a device for optically interrogating the individuals in a sample population (e.g., a microscope for imaging an organism), a device for physically manipulating and/or interrogating the individuals in a sample population (e.g., a device to perform microinjections into the individuals), a device for electrically manipulating and/or interrogating the individuals in a sample population (e.g., electrodes for performing electrotaxis or electropharyngeogram (EPG) experiments), a device for magnetically manipulating the individuals in a sample population (e.g., magnets for interrogating the response of magnetically active neurons) or combinations thereof.

The multiplexer microfluidic device can be used to rapidly and automatically process samples, including populations of organisms. One or more distinct sample populations (e.g., nematodes such as *C. elegans*, zebrafish embryos and larvae, *Drosophila* embryos and larvae, cell aggregates, nanoparticles, or microparticles) can be introduced into one or more different sample reservoirs of the multiplexer microfluidic device. Pressure can then be applied to the sample reservoirs, and one or more valves within the multiplexer microfluidic device can be actuated to selectively direct fluid flow from a predetermined sample reservoir to the sample processing element (via flow through (i.) the inlet channel fluidly connecting the predetermined sample reservoir to the main channel; and (ii.) the main channel). After delivery of the first sample population from the first sample reservoir, one or more valves can be actuated to deliver a second sample population to the sample processing element. The multiplexer microfluidic device is configured such that the sample populations are not substantially mixed during delivery to the sample processing element. This process can be repeated to serially deliver a plurality of unique sample populations to a sample processing element while maintaining segregation between the sample populations.

Also provided are microfluidic sample processing elements configured to individually process multicellular organisms. The microfluidic sample processing elements can be fluidly connected to the multiplexer microfluidic device described above. In these cases, the multiplexer microfluidic device in combination with the microfluidic sample processing element can be used to rapidly and automatically process multiple unique populations of model organisms while maintaining segregation between the populations.

For example, provided are microfluidic sample processing elements designed to serially process multiple unique populations of model organisms while maintaining segregation between the populations. In some embodiments, the microfluidic sample processing element comprises a loading chamber; a staging chamber fluidly connected to the loading chamber to form an intersection; a trapping chamber fluidly connected to the staging chamber to form an intersection; a first valve positioned in proximity to the intersection of the loading chamber and the staging chamber to regulate fluid flow between the loading chamber and the staging chamber; and a second valve positioned in proximity to the intersection of the staging chamber and the trapping chamber to regulate fluid flow between the staging chamber and the trapping chamber.

The first and second valves are configured such that sequential operation of the first valve and the second valve selectively directs a single organism first from the loading chamber into the staging chamber (termed "staging"), and subsequently from the staging chamber into the trapping chamber (termed "injection"). The dimensions of the staging chamber (e.g., height, width, and length) are selected in accordance with the dimensions of the multicellular organisms so as to permit only one of the multicellular organisms to be present within the staging chamber at a time. In this way, the first valve, second valve, and staging chamber combine to function as a 'sally port' which sequentially delivers single multicellular organisms from the loading chamber to the trapping chamber.

One or more devices to manipulate and/or interrogate the organism are configured so as to manipulate and/or interrogate the single organism localized within the trapping chamber. The device can be, for example, a device for optically manipulating the organism (e.g., a device for performing laser surgery on an organism), a device for optically interrogating the organism (e.g., a microscope for imaging an organism), a device for physically manipulating and/or interrogating the organism (e.g., a device to perform microinjections into the individuals), a device for electrically manipulating and/or interrogating the organism (e.g., electrodes for performing electrotaxis or electropharyngeograms—EPG experiments), a device for magnetically manipulating the organism (e.g., magnets for interrogating the response of magnetically active neurons) or combinations thereof. Upon entering the trapping chamber, each organism can be individually manipulated and/or interrogated. Once manipulated and/or interrogated, the organism can be flushed from the trapping chamber, and the process can be repeated to manipulate and/or interrogate the remaining multicellular organisms.

In some embodiments, one or more immobilization elements is configured to immobilize the organism within the trapping chamber and to facilitate the manipulation and/or interrogation of the organism. Examples of suitable immobilization elements include, but are not limited to, a sieve structure fluidly connected to the trapping chamber configured to fluidly restrict a multicellular organism within the trapping chamber; a valve configured to mechanically restrict a multicellular organism within the trapping chamber; protrusions (for example, extending from one or more walls of the trapping chamber) configured to physically restrict a multicellular organism within the trapping chamber; a cooling element configured to decrease the temperature of the trapping chamber and decrease the motility of the multicellular organism; and combinations thereof.

Also provided are microfluidic sample processing elements designed to trap and/or process multiple unique populations of model organisms in parallel while maintaining segregation between the populations. The sample processing elements can comprise a main channel inlet, a plurality of outlet channels fluidly connected to the main channel inlet, and a plurality of trapping chambers fluidly connected to each of the outlet channels. The sample processing element can further include one or more valves positioned along each outlet channel to regulate fluid flow through the outlet channels. The one or more valves positioned along each outlet channel can be configured to form a multiplexer, as described above, which can selectively and sequentially direct each population of model organisms from the main inlet channel into a predetermined outlet channel.

Also provided are multi-trap microfluidic devices for simultaneously housing and screening multiple unique populations of model organisms while maintaining segregation between the populations. The multi-trap microfluidic devices can include one or more sample reservoirs into which a sample population can be loaded, and a sample processing element fluidly connected to each sample reservoir which is configured to trap, house, interrogate, process, manipulate, and/or actuate members of each population in parallel. The devices can be configured to allow for multiple model organisms in a population to be, for example, housed, trapped, manipulated, and/or analyzed simultaneously.

BRIEF DESCRIPTION OF THE DRAWINGS

FIG. 14A illustrates an empty trapping chamber (e.g., without an organism present in the trapping chamber). FIG. 14B illustrates a trapping chamber containing a single *C. elegans* worm. The control layer of the pneumatic valve configured to mechanically restrict the worm within the trapping chamber is not pressurized, and the worm is able to freely move within the trapping chamber. FIG. 14C shows a worm immobilized in the trapping chamber. The worm was immobilized by pressurizing the control layer of the pneumatic valve configured to mechanically restrict the worm within the trapping chamber. As shown in FIG. 14C, laser axotomy could be performed on the trapped worm.

FIG. 20A is a schematic illustration of the gasket system components, including an exploded view illustrating how they vertically stack (left) and a perspective view illustrating the assembled device (right). FIG. 20B includes photographs of an example gasket system with pneumatic inputs and twist latches in an open (left) and sealed configuration (right).

FIG. 21A is a photograph of individual pneumatic outputs and their corresponding air delivery lines in the partially-assembled gasket. FIG. 21B illustrates the entire gasket system with a microfluidic device and the pneumatic outputs sealed to individual valve inputs on the chip. FIG. 21C is a schematic illustrating the delivery of pressurized air (top arrow) via the gasket to an individual liquid reservoir connected to an on-chip valve to pressurize the liquid (bottom arrow) and close the valve.

FIG. 26A is a schematic drawing illustrating the location of the four wells (highlighted in the schematic). FIG. 26B is a plot of the fraction of the total initial population in each well delivered during the delivery sequence as function of two operation pressures applied to the well reservoir array through the gasket (n=3).

FIG. 28A illustrates the first configuration of worm strains preloaded into the wells of rows A and H before initiating the delivery sequence (top) and a truth table for mixing events between given wells of interest and all other wells in the given row that cannot be logically eliminated in the given configuration (bottom). FIG. 28B illustrates the second preloaded configuration of worm strains and corresponding population mixing truth table. The coded worm strain name key is also shown. FIG. 28C illustrates the sequence order of well populations delivered during experiments to confirm elimination of cross-contamination between wells within rows of the device's well plate reservoir array. FIG. 28D illustrates overlapping the confirmed non-mixing cases of the truth tables for worm strain pre-loading configurations in FIGS. 28A and 28B. As shown in FIG. 28 D, validating both cases confirms that no mixing occurs within the given rows of the device during the delivery of sample populations.

DETAILED DESCRIPTION

General Definitions

Figure 1A:
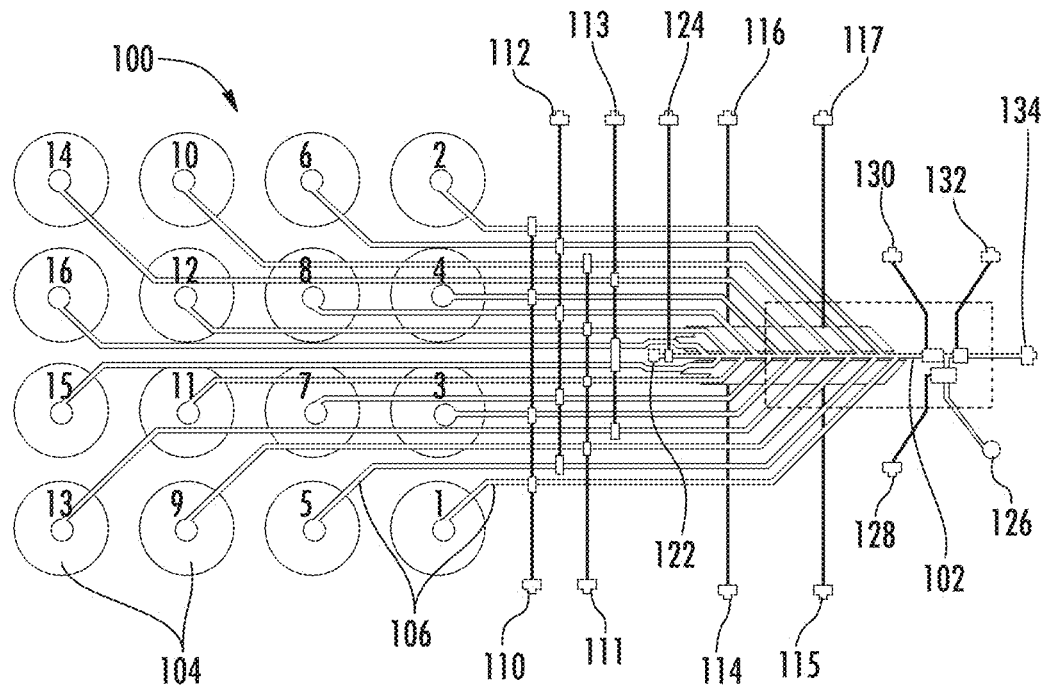
FIG. 1A is a schematic drawing illustrating a multiplexer microfluidic device.

"Microfluidic Device," as used herein, refers to a device that includes one or more microfluidic channels, one or more microfluidic valves, one or more microfluidic chambers, or combinations thereof, and are configured to carry, store, transport, and/or analyze samples in fluid volumes of less than ten milliliters (e.g., in fluid volumes of 5 mL or less, in fluid volumes of 2.5 mL or less, or in fluid volumes of 1.0 mL or less). The microfluidic device described herein can be configured to individually process a variety of samples. As used in this context, the term "process" can include transporting the individual members of one or more sample populations to a sample processing element (or fluid outlet), manipulating and/or interrogating the individual members of one or more sample populations, or combinations thereof.

"Microfluidic channel," as used herein, refers to a feature within a microfluidic device that forms a path, such as a conduit, through which one or more fluids can flow. In some embodiments, microfluidic channels have at least one cross-sectional dimension that is in the range from about 0.1 microns to about 10 millimeters (e.g., from about 1 micron to about 5 mm, from about 1 micron to 1 mm, from about 1 micron to about 750 microns, from about 1 micron to about 500 microns, from about 5 microns to about 500 microns, or from about 5 microns to about 150 microns).

"Sample Population," as used herein, refers to a sample that can be processed using one or more of the microfluidic devices described herein. The sample population can comprise a plurality of organisms, cells, cell aggregates, particles, or other suitable analytes. In certain embodiments, the sample populations comprise motile microscopic organisms. For example, the sample populations can be model organisms used in biochemical research. In other embodiments, the sample populations can be non-biological materials, such as populations of nanoparticles, microparticles, or combinations thereof. Examples of suitable sample populations include nematodes, such as *C. elegans*, zebrafish (*Danio rerio*) embryos and larvae, *Drosophila* embryos and larvae, cell aggregates, nanoparticles, and microparticles. In some embodiments, the members of a sample population processed by a microfluidic device share one or more characteristics which distinguishes them from one or more other sample populations processed using the microfluidic device.

Multiplexer Microfluidic Devices

Multiplexer microfluidic devices configured to automatically deliver one or more distinct sample populations to a sample processing element (or fluid outlet) are provided.

The multiplexer microfluidic device comprises a main channel, a plurality of sample reservoirs, and a plurality of inlet channels. Each inlet channel in the multiplexer microfluidic device fluidly connects a single sample reservoir to the main channel.

The particular design of the multiplexer microfluidic device, including the number and type of inlet channels and sample reservoirs, the presence or absence of additional microfluidic components in the device, and the arrangement of the microfluidic components within the device, will be dependent upon a number of factors. These factors can include the intended application of the multiplexer microfluidic device, and the number and nature of the one or more sample populations to be processed using the device.

In some cases, the microfluidic channels (e.g., the inlet channels and the main channel) can independently range in length from about 1 micron to about 50 cm (e.g. from about 10 microns to about 25 cm, from about 10 microns to about 10 cm, from about 100 microns to about 25 cm, or from about 100 microns to about 10 cm). At these length scales one observes very low Reynolds numbers, which can result in laminar or near laminar flow. As a consequence, the primary fluid mixing mechanism becomes diffusion rather than turbulence. The length scales of microfluidic channels are also ideal for manipulating samples with dimensions in the micron range.

The microfluidic channels can independently be linear in shape, or they can have any other configuration required for device function, including a curved configuration, spiral configuration, angular configuration, or combinations thereof. The microfluidic channels can be fabricated to have a variety of cross-sectional shapes, including but not limited to, square, rectangular, triangular (i.e., v-shaped), hemispherical, and ovular.

The microfluidic channels can have varied cross-sectional dimensions depending on the applications for the microfluidic device. For example, the cross-sectional dimensions of the microfluidic channels can be selected to accommodate the sample population being processed by the microfluidic device. Table 1 includes the dimensions (length and width) of representative multicellular microscopic organisms that can be processed using the microfluidic devices described herein. In some embodiments, the microfluidic channels have cross-sectional dimensions that are greater than 50% (e.g., greater than 80%, greater than 120%, greater than 140%, greater than 160%, greater than 180%, greater than 200%, greater than 225%, greater than 250%, or greater than 275%) of the largest cross-sectional dimension of the shortest body axis of the sample being processed by the microfluidic device.

TABLE 1

Dimensions of representative multicellular microscopic organisms that can be processed using the microfluidic devices.

| Organism | Length (microns) | Width (microns) |
|---|---|---|
| C. elegans (nematode) | 250-1500 | 5-100 |
| Danio rerio (zebrafish larvae) | ≤4000 | ≤300 |
| Drosophila melanogaster (fruitfly larvae) | 300-1500 | 150-350 |

In some embodiments, the inlet channels, main channel, or combinations thereof have a height and a width. In some embodiments, the inlet channels, main channel, or combinations thereof independently have a height that ranges from about 0.1 micron to about 1000 microns (e.g., from about 1 micron to about 750 microns, from about 1 micron to about 500 microns, from about 100 microns to about 750 microns, from about 5 microns to about 500 microns, or from about 5 microns to about 150 microns). In some embodiments, the inlet channels, main channel, or combinations thereof independently have a width that ranges from about 1 micron to about 1000 microns (e.g., from about 1 micron to about 750 microns, from about 1 micron to about 500 microns, from about 100 microns to about 750 microns, from about 5 microns to about 500 microns, or from about 5 microns to about 150 microns).

Where each inlet channel fluidly connects with the main channel, an intersection is formed. The intersections can be formed by the inlet channels fluidly connecting with the main channel at any suitable angle and in any suitable orientation. In certain embodiments, the intersections of the inlet channels and the main channel are not perpendicular (i.e., the angle formed between the main channel and the inlet channel at the intersection is not 90 degrees). All of the inlet channels in the device can be configured to intersect the same side of the main channel. Alternatively, the inlet channels in the device can be configured to intersect the main channel on both side walls of the main channel along its length. In some embodiments, the intersections of the inlet channels and the main channel are staggered, meaning that where an inlet channel forms an intersection with the main channel (e.g., on one side wall of the main channel), a second inlet channel does not intersect the main channel at the same point (e.g., on the opposite side wall of the main channel). In embodiments where the intersections of the inlet channels and the main channel are staggered, the entrances of two inlet channels do not sit directly across from one another along the main channel.

Valves

The multiplexer microfluidic device further comprises a plurality of valves positioned along the inlet channels to regulate fluid flow through the inlet channels. The plurality of valves in the multiplexer microfluidic device are configured such that operation of one or more of the plurality of valves selectively directs fluid flow through a predetermined inlet channel in the device when pressure is applied to the sample reservoirs.

At least a first valve and a second valve are positioned along each fluid inlet channel to regulate fluid flow through the inlet channel. The first valve and the second valve are configured to be independently operable, meaning that the first valve and the second valve can be opened and closed independent of one another.

The first valve is positioned in proximity to the intersection of the inlet channel and the main channel. In some embodiments, the distance between the first valve and the intersection of the inlet channel and the main channel is selected in view of the dimensions of the sample population being processed by the microfluidic device. For example, the distance between the first valve and the intersection of the inlet channel and the main channel can be selected such that the distance between the first valve and the intersection of the inlet channel and the main channel is less than largest dimension of the sample being processed by the device, so as to minimize the ability of members of a sample population to flow into other inlet channels and occupy the space between the first valve and the intersection of the inlet channels and the main channel. In this way, cross-contamination of sample populations can be minimized.

In some instances, the distance between the first valve and the intersection of the inlet channel and the main channel is less than 100% (e.g., less than 90%, less than 80%, less than 70%, less than 60%, less than 50%, less than 40%, less than 30%, less than 25%, less than 20%, or less than 10%) of the largest dimension of the sample being processed by the device.

In some embodiments, the distance between the first valve and the intersection of the inlet channel and the main channel is less than about 4000 microns (e.g., less than about 3500 microns, less than about 3000 microns, less than about 2500 microns, less than about 2000 microns, less than about 1500 microns, less than about 1250 microns, less than about 1000 microns, less than about 900 microns, less than about 800 microns, less than about 700 microns, less than about 600 microns, less than about 500 microns, less than about 400 microns, less than about 300 microns, less than about 200 microns, less than about 150 microns, less than about 100 microns, less than about 75 microns, less than about 50 microns, less than about 25 microns, less than about 20 microns, less than about 15 microns, less than about 10 microns, or less).

In some embodiments, the distance between the first valve and the intersection of the inlet channel and the main channel ranges from about 0.1 microns to about 4000 microns (e.g., from about 5 microns to about 3000 microns, from about 10 microns to about 3000 microns, from about 20 microns to about 2000 microns, from about 50 microns to about 2000 microns, from about 10 microns to about 1000 microns, from about 10 microns to about 750 microns, from about 10 microns to about 500 microns, from about 10 microns to about 400 microns, from about 10 microns to about 250 microns, from about 10 microns to about 150 microns, or from about 10 microns to about 100 microns).

The microfluidic valves incorporated into the multiplexer microfluidic device can independently have a variety of different structures. In certain embodiments, the microfluidic valves are pneumatically activated.

In some embodiments, the valves are configured to completely block fluid flow when in the closed position. The valves can also be configured such that, when the valves are in the closed position, they do not completely block fluid flow through the microfluidic device. In these embodiments, the valves can be configured such that when valves are in the closed position, they prevent the sample from flowing past the valve.

A variety of suitable pneumatically activated microfluidic valves are known in the art. For example, microfluidic valves may be formed by a region of overlap between two vertically stacked channel layers (a flow channel and a control channel) that are not fluidly connected, and are separated by a horizontal, thin membrane ceiling. When pressure is applied to the control channel, the membrane deflects into the flow channel (i.e., the microfluidic channel) and interrupts fluid flow through the microfluidic channel. See, for example, U.S. Patent Application Publication No. US 2012/0061305. Pneumatically activated microfluidic valves can also be formed from two adjacent channels (a flow channel and a control channel) that are not fluidly connected, and which are separated by vertical membrane wall. When pressure is applied in the control channel, the vertical wall deforms into the flow channel (i.e., the microfluidic channel), and interrupts fluid flow through the microfluidic channel. See, for example, U.S. Patent Application Publication No. US 2011/0151578. Pneumatically activated microfluidic valves can also be formed from a membrane layer positioned between two vertically stacked channel layers which are composed of glass or other high young's modulus material relative to the membrane material. The flow channel in the valve area is broken into two separated segments, which are non-continuous for fluid flow. When pressure is no longer applied to the control layer, the pressure in the flow layer deflects the membrane away from the flow layer and a connection is established between the two previously disconnected segments of the flow layer. See, for example, U.S. Patent Application Publication No. US 2007/0237686.

Microfluidic valves can also be formed from a screw or metallic pin embedded in the bulk material of the device that is positioned directly above the flow channel. When mechanical actuation is applied to the pin, the pin collapses the ceiling of the flow channel in the valve region, and blocks fluid flow. In these cases, the metallic pin can be activated via manual manipulation, magnetic actuation, or mechanical actuation. See, for example, U.S. Patent Application Publication No. US 2010/0116343. The microfluidic valve can also be a mechanical rotary valve positioned outside of the device that is fluidly coupled to device to control flow within a microchannel. See, for example, U.S. Pat. No. 6,748,975 to Hartshomre, et al. The microfluidic valves can also be mechanical pinch valve assemblies with built-in flow channels coupled to the device's microchannels. In these valves, the pinch valve is configured to collapse a pillar into its own built-in flow channels to stop fluid flow. The pillar can be retracted to resume flow through the channel. See, for example, U.S. Pat. No. 7,892,496 to McAvoy, et al. Other suitable microfluidic valves include horizontal and vertical one-way flow valves. See, for example, U.S. Patent Application Publication No. US 2002/0168278.

Figure 12:
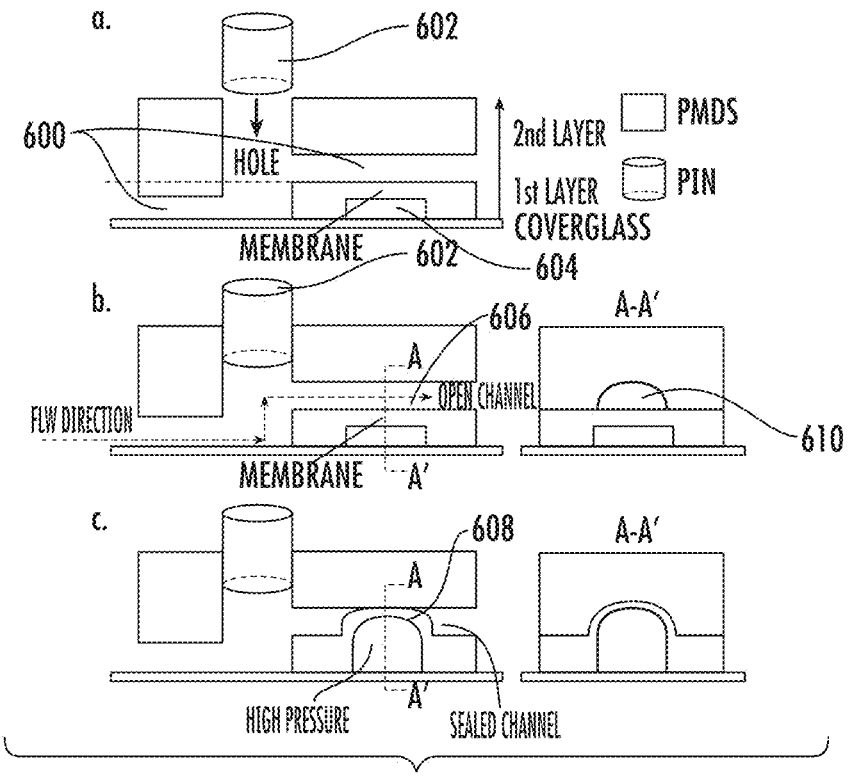
FIG. 12 is a schematic illustration of a 3-dimensional microfluidic valve.

In certain embodiments, the microfluidic valve is a 3-dimensional pneumatically activated valve configured to completely block fluid flow through a microfluidic channel. An example of a 3-dimensional valve is schematically illustrated in FIG. 12. As illustrated in FIG. 12, panel A, the 3-dimensional valve comprises two vertically stacked microfluidic layers containing a microfluidic channel (600). By punching a single hole through both layers and sealing the top of the hole with a metal plug (602), the microfluidic channels (600) are fluidly connected. A control channel (604) is located above or below the microfluidic channel (600) in one of the layers, separated by a deformable membrane.

When no pressure is applied to the control channel (FIG. 12, panel B), the microfluidic channel (600) is unobstructed, and fluid flows through the channel. When pressure is applied to the control channel (FIG. 12, panel C), the deformable membrane (608) is forced into the microfluidic channel (600), obstructing fluid flow. The microfluidic channel has a cross-section (610) that is complementary in shape to the deformable membrane when pressure is applied to the control channel (604), such that applied pressure completely seals the microfluidic channel. This tight sealing can allow fluid flow through the microfluidic channel (600) to be completely stopped when the 3-dimensional valve is in the closed position.

Sample Reservoirs

The multiplexer comprises a plurality of sample reservoirs, each of which is fluidly connected to the main channel by a unique inlet channel. In some embodiments, the inlet channels are fluidly connected to the base of the sample reservoirs.

The sample reservoirs can have a variety of shapes and structures, as desired to facilitate the processing of particular samples. Any number of sample reservoirs can be incorporated in the multiplexer microfluidic device. In some embodiments, the microfluidic device comprises from 6 to 9600 sample reservoirs (e.g., from 6 to 200 sample reservoirs).

In some embodiments, the sample reservoirs comprise microwells. The microwells can be structurally distinct from the multiplexer microfluidic device (e.g., they can be formed on or within a different piece of substrate material than the multiplexer microfluidic device). In these cases, the microwells can be fluidly connected to the sample reservoirs, for example, via tubing. In other embodiments, the microwells are integrated within the multiplexer microfluidic device (i.e., the microwells are formed on or within the substrate material that forms the multiplexer microfluidic device).

In some embodiments, the microwells comprise openings located on the surface of the multiplexer microfluidic device. The openings may have any shape. In some embodiments, the openings are circular, and have a diameter ranging from about 100 microns to about 15 mm (e.g., from about 500 microns to about 10 mm, from about 2 mm to about 8 mm, from about 4 mm to about 8 mm, or from about 6.75 mm to about 7.25 mm).

The depth of the microwells, governed by the height of the solid side walls forming the microwells, can vary to provide microwells having the desired volume and/or volume-to-surface-area ratio for particular applications. In certain instances, the depth of the microwells ranges from about 25 microns to about 10 cm (e.g., from about 50 microns to about 5 cm, or from about 100 microns to about 1.5 cm). In some embodiments, the volume of the microwells ranges from about 1 nL to about 1.5 mL (e.g., from about 50 nL to about 1 mL, or from about 50 µL to about 400 µL).

In some embodiments, the microwells are tapered in shape, such that the area of a horizontal cross-section of a microwell proximal to the base of the microwell is smaller than the area of a horizontal cross-section of the microwell distal to the base of the microwell. For example, the microwells can have a conical shape.

The microwells can be arranged in a variety of geometries depending upon the overall shape of the microfluidic device. For example, in some embodiments, the microwells are arranged in rectangular or circular arrays. The microwells may be equally spaced from one another or irregularly spaced. In some embodiments, the edges of neighboring microwells are separated by at least about 50 microns (e.g., at least about 75 microns, at least about 100 microns, at least about 150 microns, at least about 200 microns, at least about 300 microns, or at least about 400 microns).

In certain embodiments, the multiplexer microfluidic device comprises an array of microwells arranged in a 2:3 rectangular matrix, so as to form a microwell plate (also known as a MICROTITER® plate). In some cases, the multiplexer microfluidic device has a total of 6, 24, 96, 384, 1536, 3456, or 9600 microwells arranged in a 2:3 rectangular matrix. In certain embodiments, the multiplexer microfluidic device comprises from 6 to 9600 microwells (e.g., from 6 to 384 microwells, or from 6 to 200 microwells). In certain embodiments, the multiplexer microfluidic device comprises 6, 24, 96, 384, 1536, 3456, or 9600 microwells In some embodiments, the multiplexer microfluidic device comprises an array of microwells which together and individually have one or more dimensions, including well diameter, well spacing, well depth, well placement, plate dimensions, plate rigidity, and combinations thereof, equivalent to the standard dimensions for microwell plates published by the American National Standards Institute (ANSI) on behalf of the Society for Biomolecular Sciences (SBS). See, for example, Journal of Biomolecular Screening, Vol. 1, Number 4, 1996, pp. 163-168, which is incorporated herein by reference for its description of the standard dimensions of multi-well plates. In this way, the array of microwells in the multiplexer microfluidic device can be rendered compatible with existing technologies for plastic MICROTITER® plates, including 8-channel micropipettes and automated plate readers.

Figure 1B:
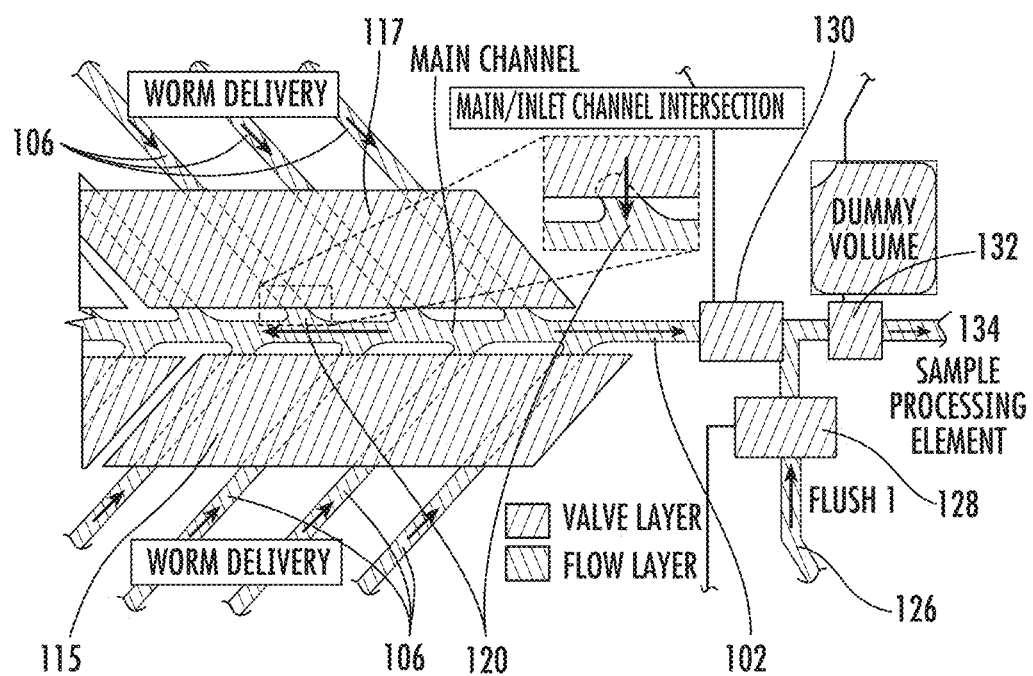
FIG. 1B is an enlarged picture showing a portion of the multiplexer microfluidic device illustrated in FIG. 1A. The enlarged region shown in FIG. 1B is indicated by the dashed rectangle superimposed on the device shown in FIG. 1A. The control channels are filled with yellow dye and the flow channels are filled with green dye. The picture indicates how well the pressurized control channels completely seal the whole cross section of the flow channels and block fluid movement in the flow channels.
Figure 1C:
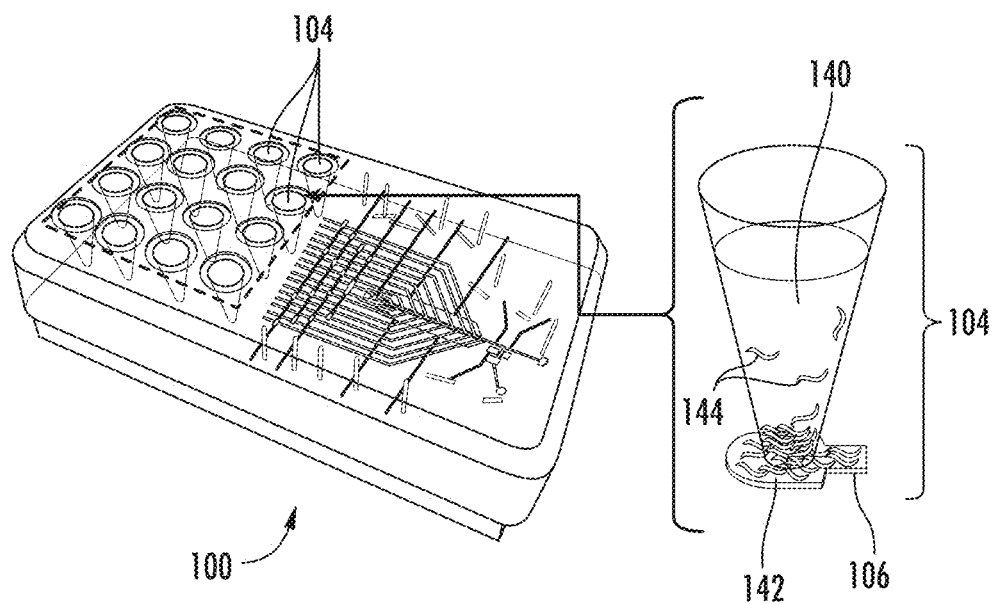
FIG. 1C illustrates the structure of an example sample reservoir comprising a microwell and shows a picture of a multiplexer microfluidic device with sixteen reservoirs.

An example sample reservoir is illustrated in FIG. 1C. The sample reservoir (104) comprises a conical microwell (140) with a height of approximately 1.4 cm. The inlet channel (106) is fluidly connected to the base of the sample reservoir (142). The diameter of the microwell is approximately 5 mm at the top opening of the microwell, and tapers down to a diameter of approximately 1.1 mm at the well channel entrance (FIG. 1C). The conical shape of the microwell encourages the sample population (illustrated in FIG. 1C as worms (144)) to settle to the base of the sample reservoir (142), in proximity to the opening of the inlet channel (106).

Sample Processing Elements

The downstream end of the main channel of the multiplexer microfluidic device can be fluidly connected to a sample processing element. The sample processing element can be configured to characterize and/or manipulate the sample populations delivered by the multiplexer, the individuals in each sample population delivered by the multiplexer, or combinations thereof. In some embodiments, the signal processing element is an external device or instrument fluidly connected to the downstream end of the main channel of the multiplexer microfluidic device. In certain embodiments, the sample processing element is integrated into the multiplexer microfluidic device (i.e., it is partially or completely fabricated within the same integral substrate material used to form the multiplexer microfluidic device).

In certain embodiments, multiple sample processing elements are fluidly connected to the downstream end of the main channel. In these cases, the plurality or sample processing elements can be configured to operate in series, in parallel, or simultaneously.

Suitable sample processing elements can be selected in view of the sample being processed, and the type of characterization and/or manipulation desired. For example, the sample processing element can be a device for optically manipulating the individuals in a sample population (e.g, a device for performing laser surgery on an organism), a device for optically interrogating the individuals in a sample population (e.g, a microscope for imaging an organism), a device for physically manipulating and/or interrogating the individuals in a sample population (e.g, a device to perform microinjections into the individuals), a device for electrically manipulating and/or interrogating the individuals in a sample population (e.g, electrodes for performing electrotaxis or electropharyngeograms—EPG experiments), a device for magnetically manipulating the individuals in a sample population (e.g., magnets for interrogating the response of magnetically active neurons) or combinations thereof.

Suitable sample processing elements include, but are not limited to, microfluidic laser axotomy platforms, flow sorter machines, white-light microscopes, fluorescence microscopes, confocal microscopes, two-photon microscopes, second harmonic generation microscopes, third harmonic generation microscopes, interference microscopes, microinjectors, devices configured to perform laser surgery, devices configured to function as optical tweezers, devices configured to perform a photoconversion, devices configured to perform photo-bleaching, devices configured to conduct photo-polymerization, devices configured to perform optogenetics experiments, devices configured to perform an optoinjection, devices configured to phenotypically characterize organisms or cells, electrodes configured to perform electrophysiological recording experiments, magnetic devices configured to interact with the sample, spectrometers (e.g., UV-, IR-, and/or fluorescence spectrometers), mass spectrometers, gas chromatographs, and combinations thereof.

In some embodiments, the sample processing element comprises the microfluidic sample processing element described herein.

In some embodiments, the downstream end of the main channel can comprise a fluid outlet. The fluid outlet can be fluidly connected to an external sample processing element, or fluidly connected to one or more external containers, which receives sample populations delivered by the device (e.g., the wells of a microplate).

Other Device Components

The multiplexer microfluidic device can further include one or more additional device components.

In some embodiments, the multiplexer microfluidic device further comprises a fluid inlet fluidly connected to the main channel upstream from the inlet channels. In some embodiments, the multiplexer microfluidic device further comprises a fluid inlet fluidly connected to the main channel downstream from the inlet channels. In certain embodiments, the multiplexer microfluidic device further comprises fluid inlets connected to the main channel both upstream and downstream from the inlet channels. Valves can be positioned downstream of the fluid inlets and/or along the fluid inlets to control fluid flow from the fluid inlets into the main channel of the multiplexer microfluidic device.

In some embodiments, the multiplexer microfluidic device further comprises one or more valves positioned along the main channel downstream from the inlets channels configured to regulate fluid flow through the main channel. These valves may have the structure of any of the valves described above. In some embodiments, valves are positioned along the main channel downstream from the inlets channels, both upstream and downstream of a fluid inlet fluidly connected to the main channel downstream from the inlet channels.

The multiplexer microfluidic device can further include one or more additional components (e.g., pressure gauges, gaskets, pressure inlets, pumps, computer-controlled solenoid valves, fluid reservoirs, and combinations thereof) to facilitate device function.

Figure 29:
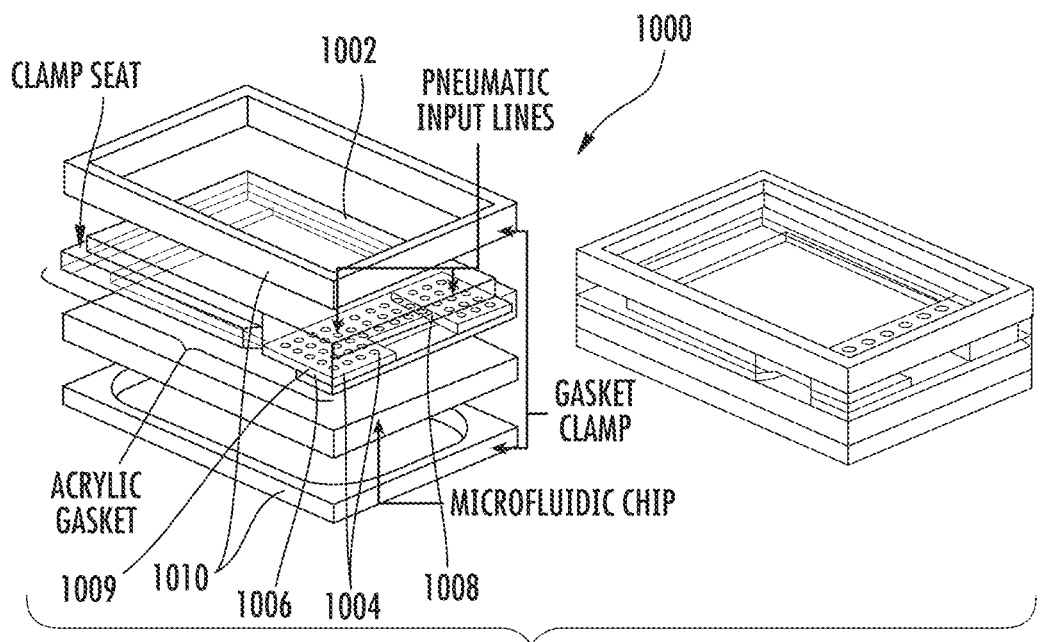
FIG. 29 is a schematic illustration of an example gasket system for use in conjunction with the microfluidic devices described herein.

In certain embodiments, the multiplexer microfluidic device can further include a gasket system configured to deliver a pneumatic input to one or more microfluidic valves in the microfluidic device, one or more sample reservoirs in the microfluidic device, one or more fluid inlets or fluid reservoirs in the microfluidic device, or combinations thereof. An example gasket system is schematically illustrated in FIG. 29. The gasket system (1000) can include a gasket (1002). The gasket can be fabricated from any suitable air-impermeable material. For example, the gasket can be fabricated from a polymer such as poly(methyl methacrylate). The gasket comprises one or more pneumatic channels (1004) that extend throughout the gasket (1002) from one or more points at the gasket exterior (1006) to one or more points on the gasket surface (1008) that are in contact with a microfluidic valve in the microfluidic device, a sample reservoir in the microfluidic device, or a fluid inlet or fluid reservoir in the microfluidic device, so as to provide a channel that pneumatically connect one or more of the points at the gasket exterior (1006) to one or more points on the gasket surface (1008) that are in contact with a microfluidic valve in the microfluidic device, a sample reservoir in the microfluidic device, or a fluid inlet or fluid reservoir in the microfluidic device. A pneumatic inlet or feed (1009) can be attached to each of the pneumatic channels (1004) at the one or more points at the gasket exterior (1006), so as to provide for the ability to pressurize the channel (e.g., to actuate a microfluidic valve in the microfluidic device pneumatically connected to the pneumatic inlet or feed via the pneumatic channel, or to apply pressure to a sample reservoir, fluid inlet, or fluid reservoir in the microfluidic device pneumatically connected to the pneumatic inlet or feed via the pneumatic channel). The gasket system (1000) can further comprise a gasket clamp (1010) configured to seal the bottom surface of the gasket to a surface of the microfluidic device, so as to so provide an airtight seal between each of the one or more pneumatic channels (1004) and a microfluidic valve in the microfluidic device, a sample reservoir in the microfluidic device, or a fluid inlet or fluid reservoir in the microfluidic device at a point on the gasket surface (1008). O-rings or other elements can be included the each point on the gasket surface (1008) to facilitate maintenance of an airtight seal at these points, so as to form a suitable means for pneumatically actuating a microfluidic valve in the microfluidic device pneumatically connected to the pneumatic inlet or feed via the pneumatic channel, or applying pressure to a sample reservoir, fluid inlet, or fluid reservoir in the microfluidic device pneumatically connected to the pneumatic inlet or feed via the pneumatic channel).

In some embodiments, the microfluidic device can include an all-stop valve. The all-stop valve can be configured to be actuated without an external pressurized input. The all-stop valve can be configured such that, when actuated, the flow from each of the sample reservoirs in the device can be stopped. The all-stop valve can facilitate device portability (e.g., enabling sample loading at any location, increasing the device's amenability with automated liquid handling systems, etc.) by obviating the need for external pneumatic pressure to maintain segregation between sample populations present in the one or more sample reservoirs in the device.

In some embodiments, the multiplexer microfluidic device further comprises signal processing circuitry or a processor configured to actuate one or more valves in the device in a predetermined fashion to direct fluid flow through the multiplexer microfluidic device. Accordingly, also provided is software configured to automatically deliver one or more sample populations to the sample processing element.

Example Device

An example multiplexer microfluidic device is illustrated in FIG. 1A. The multiplexer microfluidic device (100) comprises a main channel (102), a plurality of sample reservoirs (104), and a plurality of inlet channels (106), each of which fluidly connects a single sample reservoir to the main channel. Referring now to FIG. 1B, where each inlet channel (106) fluidly connects with the main channel (102), an intersection (120) is formed. The inlet channels (106) in the device can be configured to intersect the main channel (102) on both side walls of the main channel along its length. The intersections of the inlet channels (106) and the main channel are staggered, meaning that where an inlet channel (106) forms an intersection (120) with the main channel (102), a second inlet channel does not intersect the main channel at the same point (i.e., the entrances of two inlet channels do not sit directly across from one another along the main channel). The downstream end of the main channel of the multiplexer microfluidic device can be fluidly connected to a sample processing element via the fluid outlet (134).

The multiplexer microfluidic device further comprises a plurality of valves (110-117) positioned along the inlet channels (106) to regulate fluid flow through the inlet channels. The plurality of valves in the multiplexer microfluidic device is configured such that operation of one or more of the plurality of valves selectively directs fluid flow through a predetermined inlet channel in the device. At least a first valve (114-117) and a second valve (110-113) are positioned along each inlet channel (106) to regulate fluid flow through the inlet channel. The first valve and the second valve are configured to be independently operable, meaning that the first valve and the second valve can be opened and closed independent of one another. The first valve (114-117) is positioned in proximity to the intersection of the inlet channel (106) and the main channel (102). The second valve (110-113) is positioned upstream of the first valve (i.e., along the inlet channel (106) between the sample reservoir (104) and the first valve (114-117)).

The example multiplexer microfluidic device further comprises a fluid inlet fluidly connected to the main channel upstream from the inlet channels (122), and a fluid inlet fluidly connected to the main channel downstream from the inlet channels (126). Valves (124 and 128) are positioned downstream of the fluid inlets to control fluid flow from the fluid inlets into the main channel of the multiplexer microfluidic device.

The example multiplexer microfluidic device further comprises valves positioned along the main channel downstream from the inlets channels (106) configured to regulate fluid flow through the main channel (102). Valves (130 and 132) are positioned along the main channel (102) downstream from the inlets channels (106), both upstream (130) and downstream (132) of fluid inlet 126.

Methods of Use

Multiplexer microfluidic devices can be used to automatically deliver one or more distinct sample populations to a sample processing element. Methods of using multiplexer microfluidic devices to automatically deliver one or more distinct sample populations to a sample processing element can involve introducing one or more distinct sample populations into one or more different sample reservoirs of the multiplexer microfluidic device, applying pressure to one or more of the sample reservoirs; actuating the first valve and second valve positioned along a first inlet channel to selectively direct fluid flow from a first sample reservoir through the first inlet channel to the main channel to transfer a first sample population to the sample processing element; and actuating the first valve and second valve positioned along a second inlet channel to selectively direct fluid flow from a second sample reservoir through the second inlet channel to the main channel to transfer a second sample population to the sample processing element. In some embodiments, the method can further include washing the main channel with fluid flowing from a fluid inlet fluidly connected to the main channel upstream from the inlet channels, a fluid inlet fluidly connected to the main channel downstream from the inlet channels, or a combination thereof between the valve actuation steps.

The multiplexer microfluidic device can be configured such that the first sample population and the second sample population are not substantially mixed during delivery to the sample processing element. In some embodiments, at least 5% (e.g., at least 15%, at least 25%, at least 30%, at least 40%, at least 50%, at least 60%, at least 70%, at least 75%, at least 80%, at least 85%, at least 90%, or at least 95%) of the sample population delivered to the sample processing element (or fluid outlet) from a particular sample population loaded in a given sample reservoir are from the particular sample population initially loaded in the given sample reservoir.

The pressure applied to direct fluid flow through the device can vary based on a number of factors, including device design, sample identity, size of the sample populations(s), the nature of the sample processing element(s), and desired processing requirements (e.g., desired delivery time or desired fraction of the sample population to be delivered), and combinations thereof. In some embodiments, the applied pressure ranges from about 0.5 psi to about 50 psi (e.g., from about 5 psi to about 25 psi).

The sample populations can be rapidly delivered to the sample processing element(s). In some embodiment, each sample population is delivered to the sample processing element at a rate of at least 1 member of the sample population (e.g., organisms, cells, cell aggregates, or particles) per second (e.g., at a rate of at least 5 members of the sample population per second, at a rate of at least 10 members of the sample population per second, at a rate of at least 15 members of the sample population per second, at a rate of at least 20 members of the sample population per second, at a rate of at least 25 members of the sample population per second, at a rate of at least 30 members of the sample population per second, at a rate of at least 40 members of the sample population per second, or at a rate of at least 50 members of the sample population per second).

In some embodiments, the multiplexer microfluidic device is configured and operated such that substantially no air bubbles form within the microfluidic channels during sample processing. In these embodiments, substantially no air bubbles impinge on the sample processing element(s) during sample processing. The lack of air bubbles can eliminate potential errors in sample processing resulting from trapped air bubbles contacting the sample processing element(s).

An automatic valve actuation sequence can be used to automatically deliver one or more distinct sample populations to a sample processing element without substantial cross-contamination of distinct sample populations.

By way of exemplification, FIGS. 2A-2E illustrate the automated valve actuation sequence used to deliver worm populations from the microwells using the multiplexer microfluidic device illustrated in FIG. 1A. For purposes of illustration, FIGS. 2A-2E illustrate the valve actuations used to deliver worms from a first microwell (1, FIG. 2A). These steps can then be repeated to deliver sample populations from a second microwell (5, FIG. 2B) in the device, as discussed in more detail below.

Figure 2A:
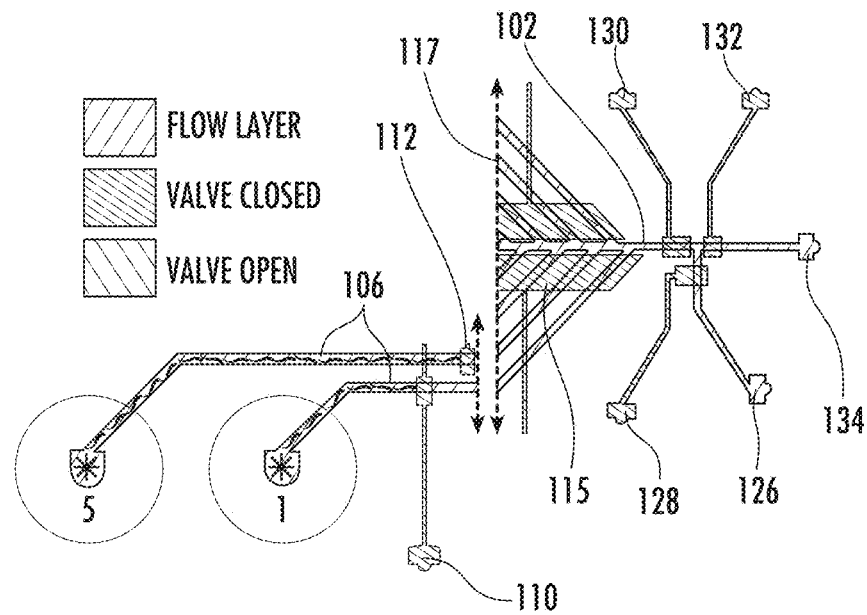
FIGS. 2A-2E are schematic drawings illustrating the automated valve actuation sequence used to deliver *C. elegans* populations from a sample reservoir of the multiplexer microfluidic device illustrated in FIG. 1.
Figure 2B:
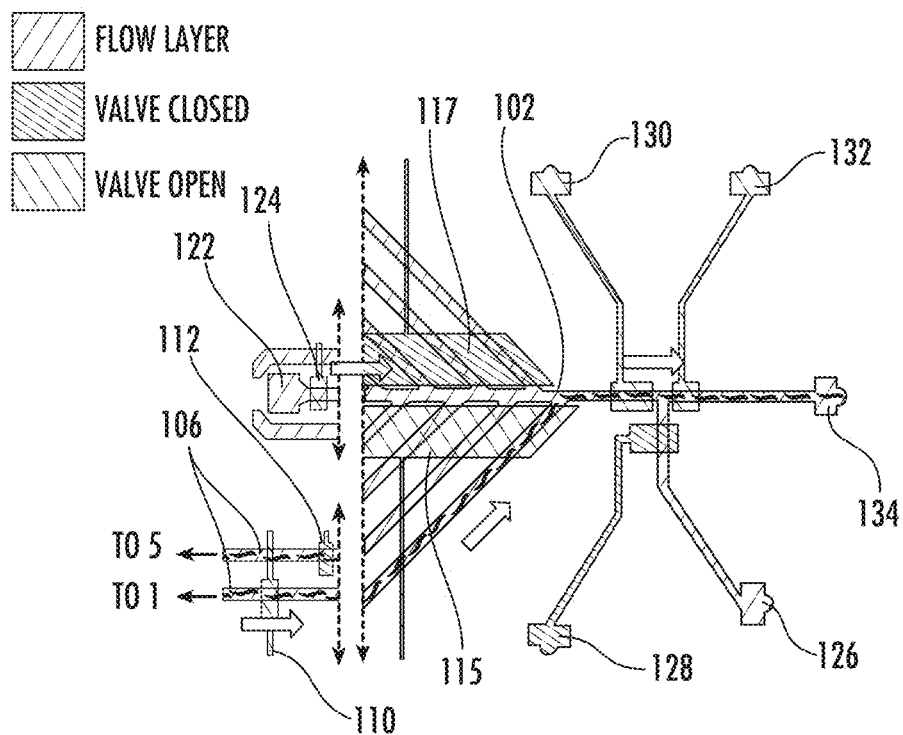
Figure 2C:
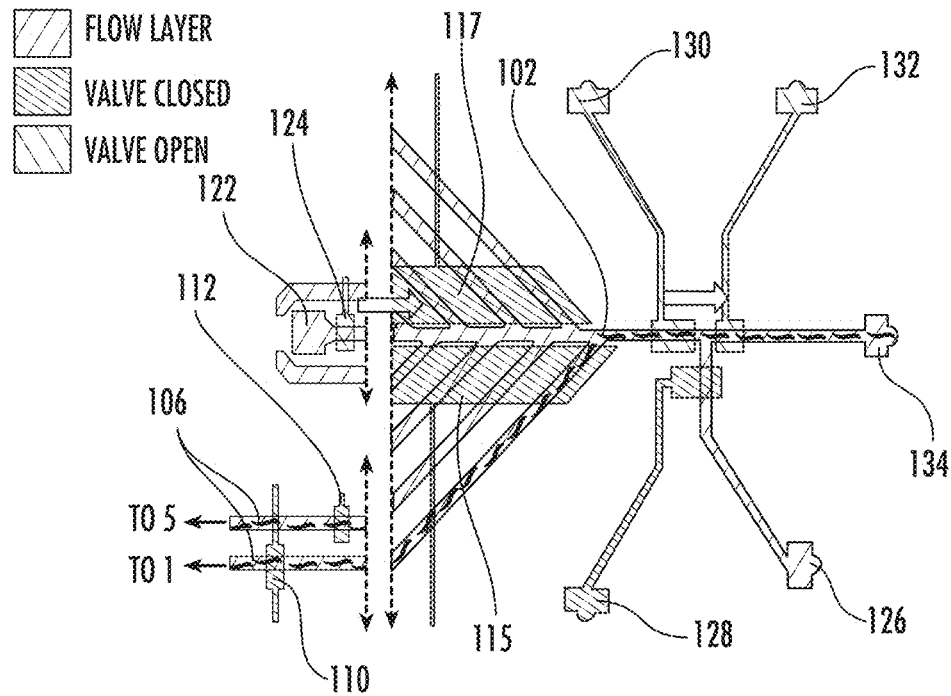
Figure 2D:
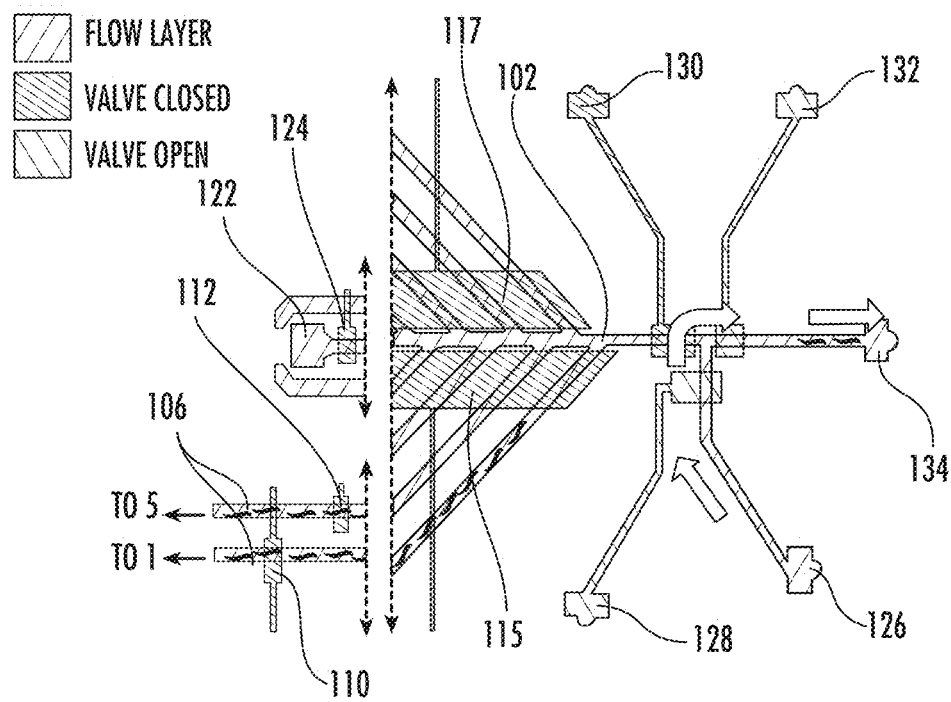
Figure 2E:
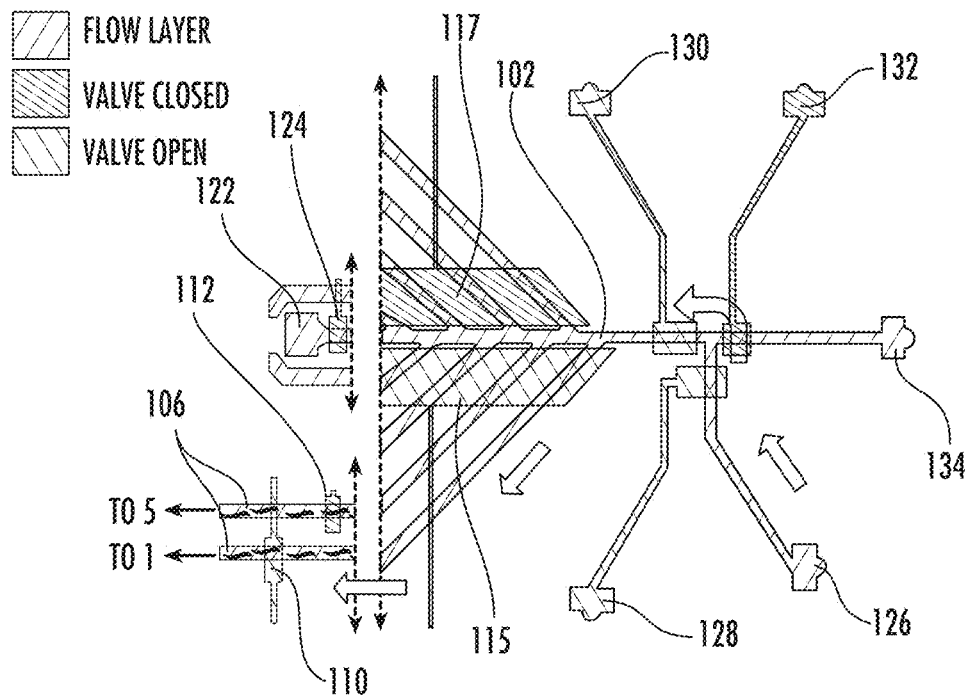

FIG. 2A schematically illustrates the elements of the multiplexer microfluidic device prior to delivery of worms from a first microwell (1). In this case, all valves in the multiplexer microfluidic device are in the closed position. Prior to delivery, the worms are pre-staged upstream of a valve (110 in the case of the first microwell 1, and 112 in the case of the second microwell 5) positioned along each fluid inlet channel (106). The closed valves prevent passage of the worms past the valves.

In step 1 (FIG. 2B), fluid flow is directed from the first microwell (1) to the exit of the main channel (e.g., a sample processing element from the fluid outlet, 134) by pressurizing the gasket and the appropriate valves (i.e., opening valves 110, 115, 130, and 132). Simultaneously, fluid flow was initiated from fluid inlet 122 by opening valve 124 and applying pressure to a fluid reservoir fluidly connected to fluid inlet 122. This causes worms to flow from microwell 1 to the exit of the main channel (e.g., a sample processing element from the fluid outlet, 134).

In step 2 (FIG. 2C), microwell 1 is no longer pressurized via the gasket, and valves 110 and 115 are closed. Fluid flow was continued from fluid inlet 122 to wash any excess animals from the main channel.

In step 3 (FIG. 2D), valves 124 and 130 were closed while stopping pressure application to 122, and fluid flow was initiated from fluid inlet 126 by opening valve 128 and applying pressure to a fluid reservoir fluidly connected to fluid inlet 126. The fluid flow from fluid inlet 126 was to wash all the animals from the main channel towards its ultimate destination (e.g., a sample processing element).

In step 4 (FIG. 2E), valve 132 was closed, and valves 130, 115, and 110 were opened. Fluid flow was continued from fluid inlet 126 to wash any remaining animals from the main channel and inlet channel back to the first microwell 1.

This automated valve actuation sequence could then be repeated to deliver sample populations from additional microwells in the multiplexer microfluidic device.

In some embodiments, the order in which the sample reservoirs were delivered to the sample processing element was selected in order to reduce the time needed to unload the worm populations, and to minimize the cross-contamination of sample populations.

With reference to FIG. 1A, in some embodiments, the microwells are delivered in a sequence such that microwells connected to the main channel by inlet channels sharing an upstream valve (e.g., sharing valve 110, 111, 112, or 113) in common, were all delivered using the sequence described above before moving on to the next series of wells. For example, fluid flow from microwells 1-4 is regulated by valve 110; therefore microwells 1-4 are all delivered prior to delivering sample populations from microwells 5-16. By unloading microwells in this fashion, the number of washing sequences required (e.g., step 4 described in FIG. 2E) are minimized. For example, sample populations can be delivered from 1-4 using steps 1-3 (FIGS. 2B-2D), for the first three microwells that share valve 110, while skipping step 4 until the fourth microwell is unloaded. Then, the automated program can perform step 4 on all four microwells simultaneously to wash back any excess worms in the inlet channels to their respective sample reservoirs.

Again with reference to FIG. 1A, in some embodiments, the order of microwells unloaded within a column group (i.e., the order with which microwells sharing a given valve 110, 111, 112, or 113) and the order in which the column groups were unloaded was selected such that the microwells whose inlet channels intersect with the main channel furthest downstream have their sample populations delivered earliest in the sequence (e.g., microwells 1-4 were delivered before microwells 13-16). In this way, a specific population of worms traveling from an inlet channel into the main channel only flows past inlet channels fluidly connected to microwells from which sample populations have already been delivered.

Microfluidic Sample Processing Elements

Also provided is a microfluidic sample processing element configured to individually and rapidly process samples (e.g., multicellular organisms, cells, cell aggregates, or particles).

The microfluidic sample processing element comprises a loading chamber; a staging chamber fluidly connected to the loading chamber to form an intersection; and a trapping chamber fluidly connected to the staging chamber to form an intersection. The microfluidic sample processing element further comprises a first valve positioned in proximity to the intersection of the loading chamber and the staging chamber to regulate fluid flow between the loading chamber and the staging chamber, and a second valve positioned in proximity to the intersection of the staging chamber and the trapping chamber to regulate fluid flow between the staging chamber and the trapping chamber.

The loading chamber is a microfluidic chamber having appropriate dimensions, including height, width, and length, to house a sample population to be processed by the device. One or more fluid inlets, optionally controlled by microfluidic valves, can be fluidly connected to the loading chamber. These fluid inlets can be used, for example, to flow fluid into the loading chamber, introduce sample populations into the loading chamber, or combinations thereof. In certain embodiments, a fluid inlet connected to a multiplexer microfluidic device, as described above, is fluidly connected to the loading chamber.

The dimensions of the staging chamber (e.g., height, width, and length) are selected in accordance with the dimensions of the samples being processed by the device so as to permit only a single sample to be present within the staging chamber at a time. For example, in the case of microfluidic sample processing elements configured to individually and rapidly process multicellular organisms, the height, width, and length of the staging chamber can be selected in accordance with the dimensions of the organism being processed by the device so as to permit only a single organism to be present within the staging chamber at a time.

In some embodiments, the staging chamber has cross-sectional dimensions (height and width) that are greater than 50% (e.g., greater than 75%, greater than 80%, greater than 120%, greater than 140%, greater than 150%, greater than 175%) but smaller than 200% of the largest cross-sectional dimension of the shortest body axis of the organism being processed by the device. In some embodiments, the staging chamber has cross-sectional dimensions (height and width) that are less than twice largest cross-sectional dimension of the organism being processed by the device.

In some embodiments, the staging chamber has a height that ranges from about 1 micron to about 1000 microns (e.g., from about 1 micron to about 750 microns, from about 1 micron to about 500 microns, from about 100 microns to about 750 microns, from about 5 microns to about 500 microns, or from about 5 microns to about 150 microns). In some embodiments, the staging chamber has a width that ranges from about 1 micron to about 1000 microns (e.g., from about 1 micron to about 750 microns, from about 1 micron to about 500 microns, from about 100 microns to about 750 microns, from about 5 microns to about 500 microns, or from about 5 microns to about 150 microns).

In some embodiments, the length of the staging chamber is between 80% and 500% of the largest dimension of the organism being processed by the device. In some embodiments, the length of the staging chamber is less than about 20,000 microns (e.g., less than about 9000 microns, less than about 8000 microns, less than about 7000 microns, less than about 6000 microns, less than about 5000 microns, less than about 4000 microns, less than about 3000 microns, less than about 2000 microns, less than about 1500 microns, less than about 1000 microns, less than about 900 microns, less than about 800 microns, less than about 700 microns, less than about 600 microns, less than about 500 microns, less than about 400 microns, or less than about 300 microns). In some embodiments, the length of the staging chamber ranges is greater than about 50 microns (e.g., greater than about 100 microns, greater than about 300 microns, greater than about 500 microns, greater than about 600 microns, greater than about 700 microns, greater than about 800 microns, greater than about 900 microns, greater than about 1000 microns, greater than about 1500 microns, greater than about 2000 microns, greater than about 3000 microns, greater than about 4000 microns, or greater than about 5000 microns).

The staging chamber can have a length ranging from any of the minimum values to any of the maximum values described above. In some embodiments, the length of the staging chamber ranges from about 50 microns to about 6000 microns (e.g., from about 50 microns to about 2000 microns, from about 250 microns to about 1200 microns, from about 300 microns to about 2000 microns, or from about 300 microns to about 1500 microns).

The first and second valves are configured such that sequential operation of the first valve and the second valve selectively directs a single member of the sample population first from the loading chamber into the staging chamber (termed "staging"), and subsequently from the staging chamber into the trapping chamber (termed "injection"). In this way, the first valve, second valve, and staging chamber combine to function as a 'sally port' which sequentially delivers single multicellular organisms from the loading chamber to the trapping chamber. The first and second valves can have any of the structures described above.

The trapping chamber is a microfluidic chamber having appropriate dimensions, including height, width, and length, to house a single sample to be processed by the device. In certain embodiments, the trapping chamber has a substantially T-shaped geometry. One or more microfluidic channels can be fluidly connected to the trapping chamber, as discussed in more detail below. In certain embodiments, a fluid inlet, controlled by a microfluidic valve, is fluidly connected to the trapping chamber.

The microfluidic sample processing element can further comprise an exit area fluidly connected to the trapping chamber. The exit area can comprise one or more microfluidic channels, optionally controlled by microfluidic valves, which form a fluid flow path leading out of the trapping chamber. In some embodiments, the exit area comprises a first microfluidic channel and a second microfluidic channel and a first valve and a second valve, wherein the first valve is configured to control fluid flow through the first microfluidic channel, and wherein the second valve is configured to control fluid flow through the second microfluidic channel. In certain embodiments, the first valve and the second valve are configured to completely block fluid flow through the first microfluidic channel and the second microfluidic channel when the first valve and the second valve are in the closed position. In certain embodiments, the first valve and the second valve are 3-dimensional valves, as described above.

The microfluidic sample processing element can further comprise one or more sieve structures fluidly connected to the loading chamber. The sieve structures can be fluidly connected to the loading chamber by fluid flow paths, each having a height, width, and length selected in accordance with the dimensions of the sample, such that the sample cannot pass through the fluid flow paths.

The microfluidic sample processing element can further comprise one or more sieve structures fluidly connected to the staging chamber. The sieve structures can be fluidly connected to the staging chamber by fluid flow paths, each having a height, width, and length selected in accordance with the dimensions of the sample, such that the sample cannot pass through the fluid flow paths.

In some embodiments, filter structures are incorporated into the microfluidic sample processing element to prevent unwanted debris from impairing device performance. Suitable filter structures include arrays of pillars, slits, and/or frits having varying gaps. The gaps can be selected in view of the sample being processed, such the filter structures allow for the passage of sample, but blocks debris from flowing through the device. The filter structures can by incorporated at the entrance of each flow channel (e.g., within the loading chamber, within the trapping chamber, within sieve structures, or combinations thereof).

The microfluidic sample processing element can further include one or more additional components (e.g., pressure gauges, gaskets, pressure inlets, pumps, computer-controlled solenoid valves, fluid reservoirs, and combinations thereof) to facilitate device function.

In some embodiments, the microfluidic sample processing element further comprises signal processing circuitry or a processor configured to actuate one or more valves in the device in a predetermined fashion to direct fluid flow through the microfluidic sample processing element and serially deliver samples to the trapping chamber. Accordingly, also provided is software configured to automatically deliver one or more samples from the loading chamber to the trapping chamber.

Immobilization Elements

In some embodiments, one or more immobilization elements are configured to immobilize the sample within the trapping chamber in order to facilitate the manipulation and/or interrogation of the sample. Examples of suitable immobilization elements include, but are not limited to, a sieve structure fluidly connected to the trapping chamber configured to fluidly restrict a multicellular organism within the trapping chamber; a valve configured to mechanically restrict a multicellular organism within the trapping chamber; protrusions (for example, extending from one or more walls of the trapping chamber) configured to physically restrict a multicellular organism within the trapping chamber; a cooling element configured to decrease the temperature of the trapping chamber and decrease the motility of the multicellular organism; and combinations thereof.

In some embodiments, the trapping chamber further comprises a sieve structure fluidly connected to one or more walls of the trapping chamber. The sieve structure is fluidly connected to the trapping chamber by fluid flow paths within the wall, each having a height, width, and length selected in accordance with the dimensions of the sample, such that the sample cannot pass through the fluid flow paths. The sieve structure can be configured to form one or more fluid flow paths from the trapping chamber to the sieve structure that fluidly restricts the sample within the trapping chamber. In certain embodiments, the sieve structure is fluidly connected to the wall of the trapping chamber opposite (i.e., arranged perpendicular to) the staging chamber.

In some embodiments, the trapping chamber further comprises a plurality of protrusions extending from one or more side walls of the trapping chamber. In certain embodiments, the protrusions extend from a side wall of the trapping chamber which further comprises a sieve structure, as described above. The protrusions are configured to physically restrict the multicellular organism within the trapping chamber. In some embodiments, the length of the protrusions is at least 5 microns (e.g., at least 10 microns, at least 15 microns, at least 20 microns, at least 25 microns. at least 30 microns, or at least 35 microns). The protrusions should leave a gap between the protrusion and the opposite wall that is greater than 50% (e.g., greater than 80%, greater than 120%, greater than 140%, greater than 160%, greater than 180%, greater than 200%, greater than 225%, greater than 250%, or greater than 275%) of the largest cross-sectional dimension of the shortest body axis of the sample being processed by the microfluidic device.

In some embodiments, the microfluidic sample processing element further comprises a valve configured to mechanically restrict a sample within the trapping chamber. In some embodiments, the valve is a pneumatic valve comprising a control layer positioned above the trapping chamber. The control layer can be separated from the trapping chamber by a deformable membrane. Upon application of pressure to the control layer, the deformable membrane can be deformed, impinging into the trapping chamber, and mechanically restricting a sample within the trapping chamber. The deformable membrane can be designed to be gas permeable to permit a gas, such as $CO_2$, to diffuse into the trapping chamber.

Devices for Manipulating and or Interrogating the Sample

One or more devices to manipulate and/or interrogate the sample are configured so as to manipulate and/or interrogate a sample localized within the trapping chamber. The device can be, for example, a device for optically manipulating the organism (e.g., a device for performing laser surgery on an organism), a device for optically interrogating the organism (e.g., a microscope for imaging an organism), a device for optically actuating the organism (e.g., optogenetically activating or inactivating the neurons of an organism), a device for physically manipulating and/or interrogating the organism (e.g., a device to perform microinjections into the individuals), a device for electrically manipulating and/or interrogating the organism (e.g., electrodes for performing electrotaxis or electropharyngeograms—EPG experiments), a device for magnetically manipulating the organism (e.g., magnets for interrogating the response of magnetically active neurons), a device for acoustically manipulating and/or interrogating the organism (e.g., a device utilizes surface acoustic wave—SAW acoustophoresis), or combinations thereof.

In some embodiments, the microfluidic sample processing element further comprises a device for optical interrogation configured to optically interrogate a sample within the trapping chamber, such as a white-light microscope, a fluorescence microscope, a confocal microscope, a two-photon microscope, a second harmonic generation microscope, a third harmonic generation microscope, an interference microscope, a line scanning fluorescence microscope, a planar laser induced fluorescence microscope, or combinations thereof. In some cases, the microfluidic sample processing element comprises a device for stochastic optical reconstruction microscopy (STORM), holography, line scanning, or other super resolution methods.

In some embodiments, the microfluidic sample processing element further comprises a device for optical manipulation configured to optically manipulate a sample within the trapping chamber, such as a device is configured to perform laser surgery, a device is configured to function as optical tweezers, a device is configured to perform a photoconversion, a device is configured to perform photo-bleaching, a device is configured to conduct photo-polymerization, a device is configured to perform optogenetics experiments, a device is configured to perform an optoinjection, a device is configured to perform microinjection, a device is configured to perform magnetic actuation of neurons, a device is configured to perform electrical actuation of neurons, or combinations thereof.

Example Microfluidic Sample Processing Element

Figure 5A:
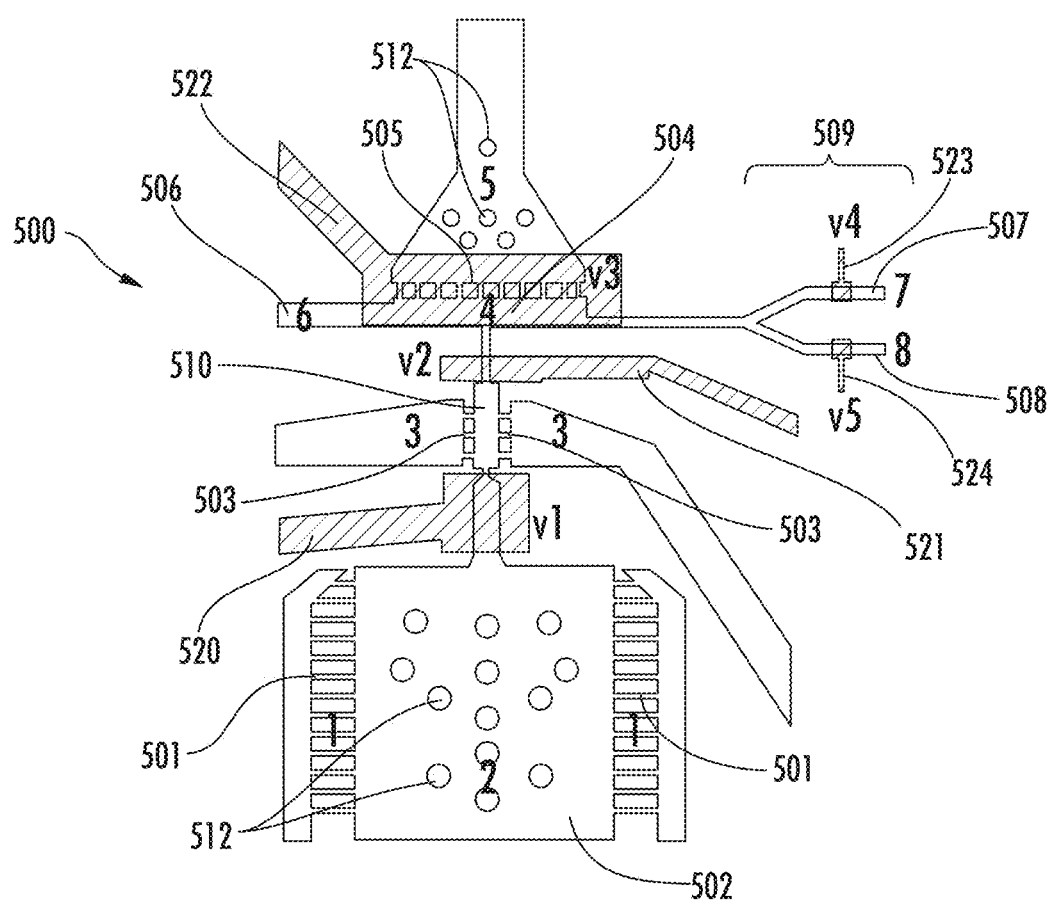
FIG. 5A is a schematic drawing illustrating a microfluidic sample processing element.

An example microfluidic sample processing element is illustrated in FIG. 5A.

The microfluidic sample processing element (500) comprises a loading chamber (502); a staging chamber (510) fluidly connected to the loading chamber to form an intersection; and a T-shaped trapping chamber (504) fluidly connected to the staging chamber to form an intersection. The microfluidic sample processing element further comprises a first valve (520) positioned in proximity to the intersection of the loading chamber and the staging chamber to regulate fluid flow between the loading chamber and the staging chamber, and a second valve (521) positioned in proximity to the intersection of the staging chamber and the trapping chamber to regulate fluid flow between the staging chamber and the trapping chamber.

The microfluidic sample processing element further comprises sieve structures (501) fluidly connected to the loading chamber (502). The sieve structures are fluidly connected to the loading chamber by fluid flow paths, each having a height, width, and length selected in accordance with the dimensions of the sample, such that the sample cannot pass through the fluid flow paths. The microfluidic sample processing element also comprises sieve structures (503) fluidly connected to the staging chamber (510). The sieve structures are fluidly connected to the staging chamber by fluid flow paths, each having a height, width, and length selected in accordance with the dimensions of the sample, such that the sample cannot pass through the fluid flow paths.

An exit area (509) is fluidly connected to the trapping chamber (504). The exit area comprises a first microfluidic channel (507) and a second microfluidic channel (508) and a first valve (523) and a second valve (524), wherein the valve 523 is configured to control fluid flow through microfluidic channel 507, and valve 524 is configured to control fluid flow through microfluidic channel 508. In this embodiment, valves 523 and 524 are 3-dimensional valves, as described above.

A sieve structure (505) is fluidly connected to the wall of the trapping chamber (504) opposite the staging chamber (510). Sieve structure 505 is fluidly connected to the trapping chamber by fluid flow paths within the wall, each having a height, width, and length selected in accordance with the dimensions of the sample, such that the sample cannot pass through the fluid flow paths. The sieve structure is configured to form fluid flow paths from the trapping chamber (504) to the sieve structure (505), which fluidly restricts the sample within the trapping chamber (504). A plurality of protrusions can optionally extend from the wall of the trapping chamber to which sieve structure 505 is fluidly connected. A pneumatic microfluidic valve (522) is positioned above the trapping chamber (504), and is configured to mechanically restrict a sample within the trapping chamber (504) when in the closed position.

A fluid inlet (506) is also fluidly connected to the trapping chamber. 506 is positioned relative to the trapping chamber (504) such that the fluid flow from fluid inlet 506 is directed perpendicular to the direction of fluid flow through the sieve structure (505) fluidly connected to the trapping chamber, and parallel to and/or towards the exit area (509).

The microfluidic sample processing element also comprises filter structures (512) incorporated within the loading chamber (502) and within the sieve structure (505) fluidly connected to the trapping chamber.

Methods of Use

The microfluidic sample processing element can be used to individually process samples from a sample population in a rapid and automated fashion.

By way of exemplification, FIGS. 5B-5H shows the sequence of valve and flow progression at each step during automation during the operation of the example device in FIG. 5A. The example device in FIG. 5A comprises optomechanical components configured to perform laser axotomies on *C. elegans* specimens delivered to the trapping chamber. Accordingly, for purposes of illustration, sample processing is discussed within the context of automated laser axotomy. However, it will be understood that other devices for the manipulation and/or interrogation of samples could be similarly integrated with the microfluidic sample processing element shown in FIG. 5A, and utilized to process samples.

Figure 5B:
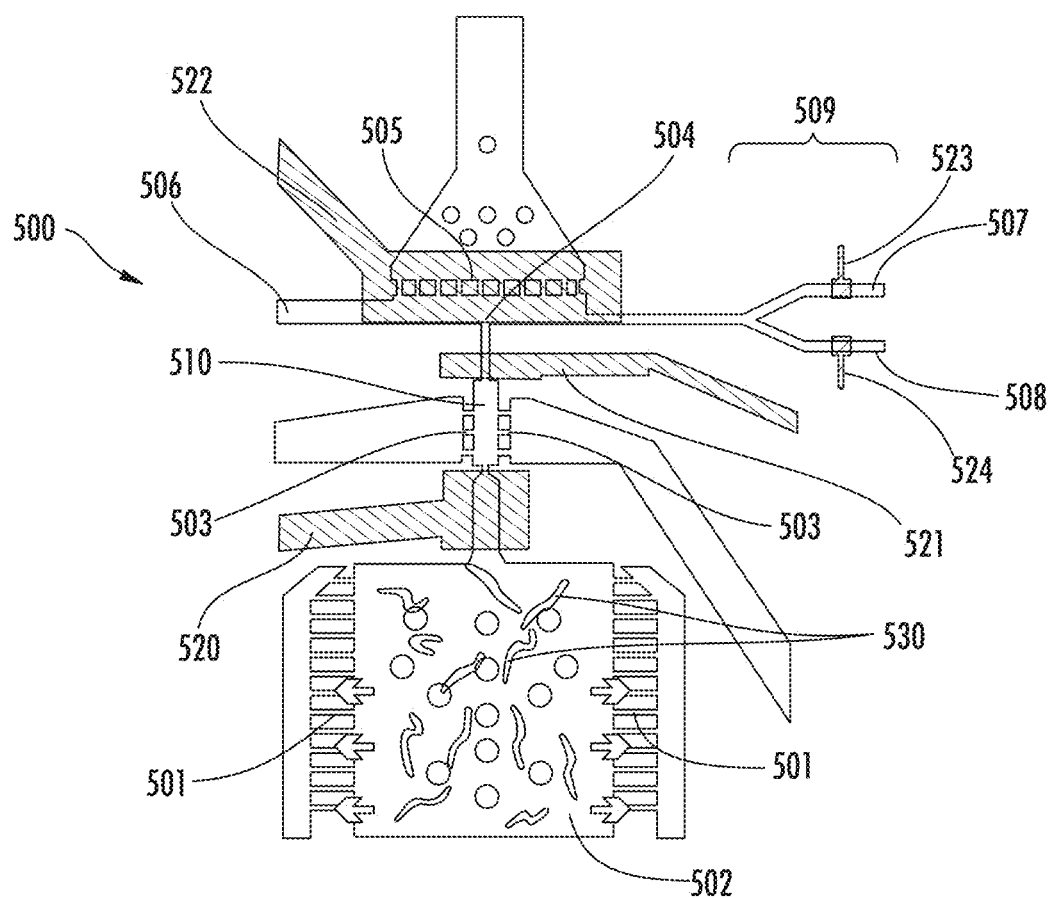
FIGS. 5B-5H are schematic drawings illustrating the automated valve actuation sequence and fluid flow patterns used to automatically process a *C. elegans* worm using the microfluidic sample processing element shown in FIG. 5A.

The microfluidic sample processing element is first loaded with a population of worms (530) by blocking all flow channels except the small flow exits provided by sieve structures (501) fluidly connected to the loading chamber (502) (FIG. 5B).

Figure 5C:
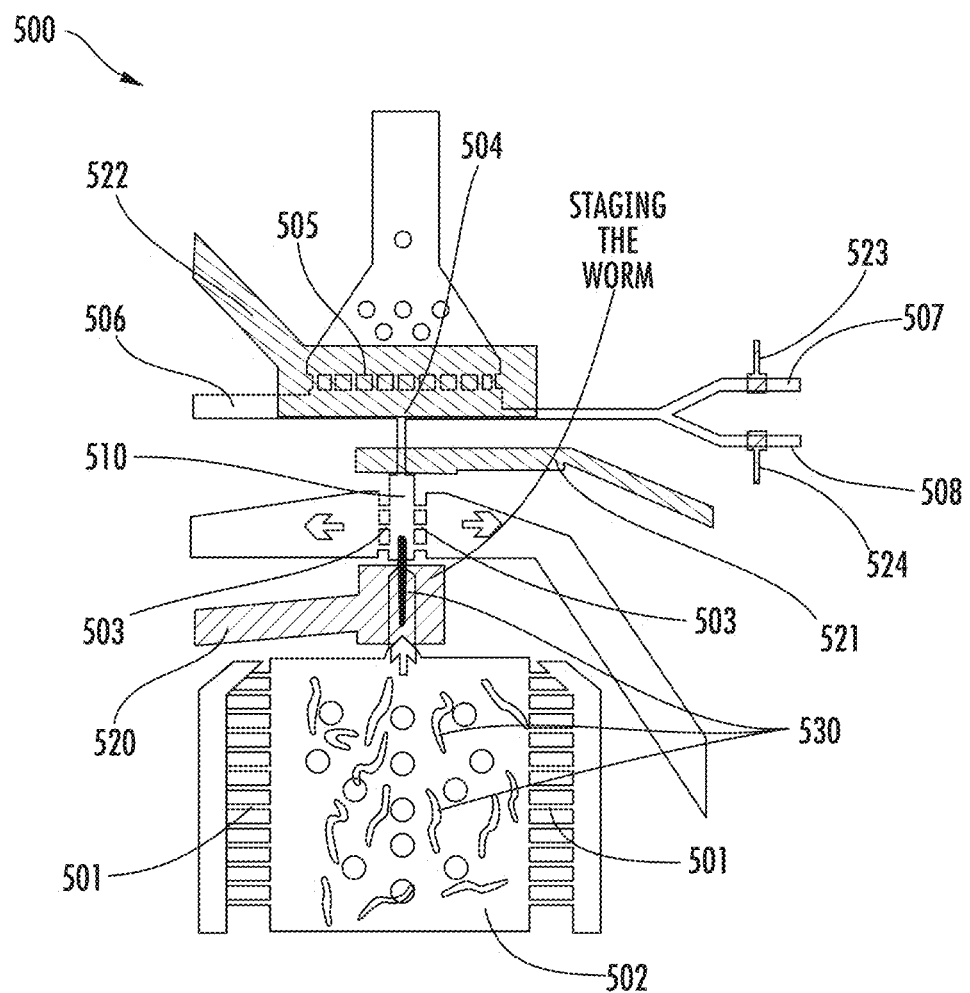
Figure 5D:
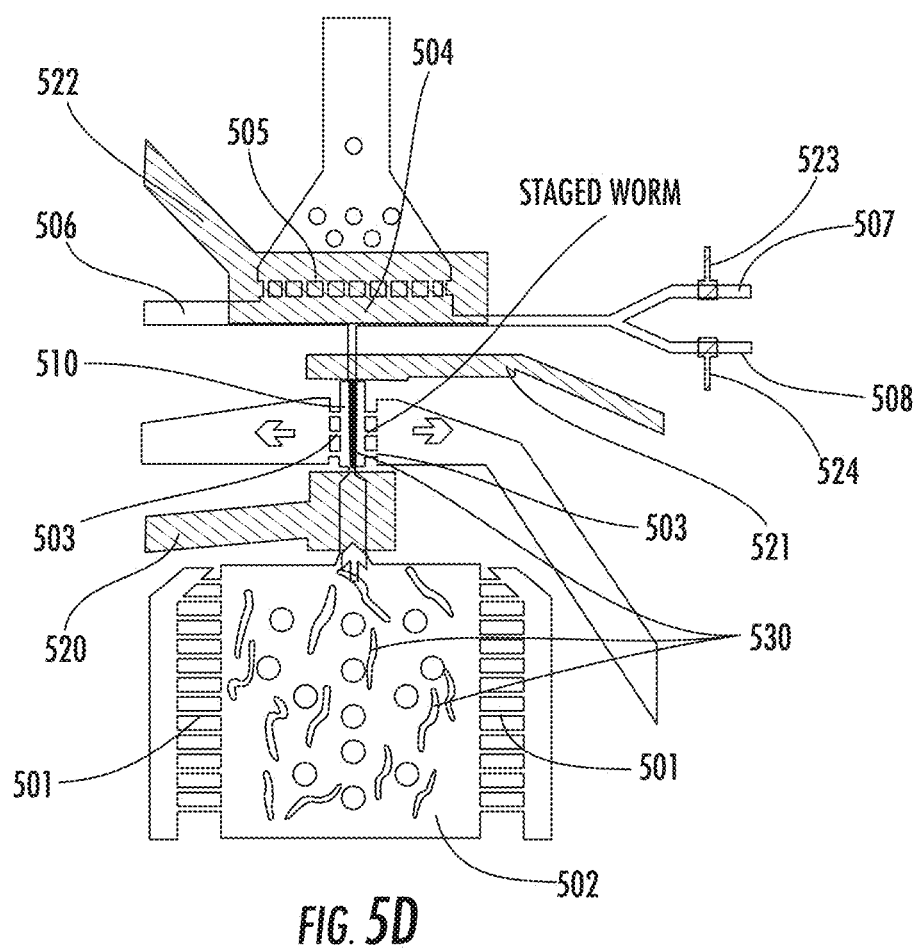

Once a population of worms was loaded into the loading chamber (502), a peristaltic-like gate is used to stage worms for serial injection into the trapping chamber (504) (FIGS. 5C-5D). The gate is operated by actuating two valves located on either side of the staging chamber (510): a first valve (520) positioned in proximity to the intersection of the loading chamber (502) and the staging chamber (510) that is configured to regulate fluid flow from the loading chamber to the staging chamber; and a second valve (521) positioned in proximity to the intersection of the staging chamber (510) and the trapping chamber (504) that is configured to regulate fluid flow from the staging chamber and the trapping chamber. Sieve structures (503) are fluidly connected to the staging chamber act to direct the worm between the first valve (520) and the second valve (521) during staging. The staging process involves two steps. In the first staging step, valve 520 is opened, and pressure is applied to the loading chamber (FIG. 5C). Valve 521 remains closed. As a result, fluid flow is directed from the loading chamber (502) and through the sieve structures (503) fluidly connected to the staging chamber (510). This fluid flow directs a worm (530) from the loading chamber (502) into the staging chamber (510). Once the worm travels into the staging chamber, the second staging step is performed. In the second staging step, valve 520 is closed, capturing a single worm (530) within the staging chamber (510) (FIG. 5D).

Figure 5E:
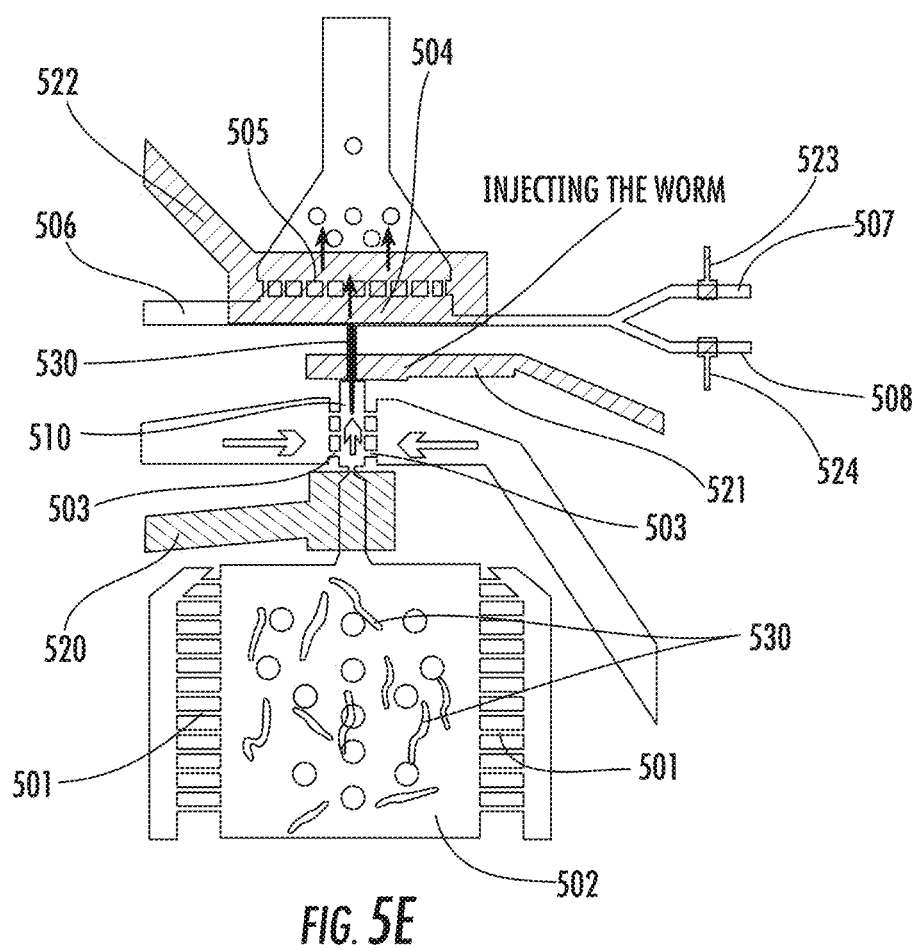

Once the worm is located in the staging chamber, the worm is then injected into the trapping chamber (504) by reversing the flow through the sieve structures (503) fluidly connected to the staging chamber (510), and opening valves 521 and 522 (FIG. 5E). The injection step lasts for approximately 1000 ms to allow the worm (530) to flow into the trapping chamber (504), and to straighten the worm against the sieve structure (505) fluidly connected to the trapping chamber. The reversed flow through the sieve structure fluidly connected to the staging chamber (503) prevents a second worm from flowing from the loading chamber (502) into the staging chamber (510) while the first worm is injected into the trapping chamber (504). In this way, only a single worm is delivered to the trapping chamber (504) at a time.

Figure 5F:
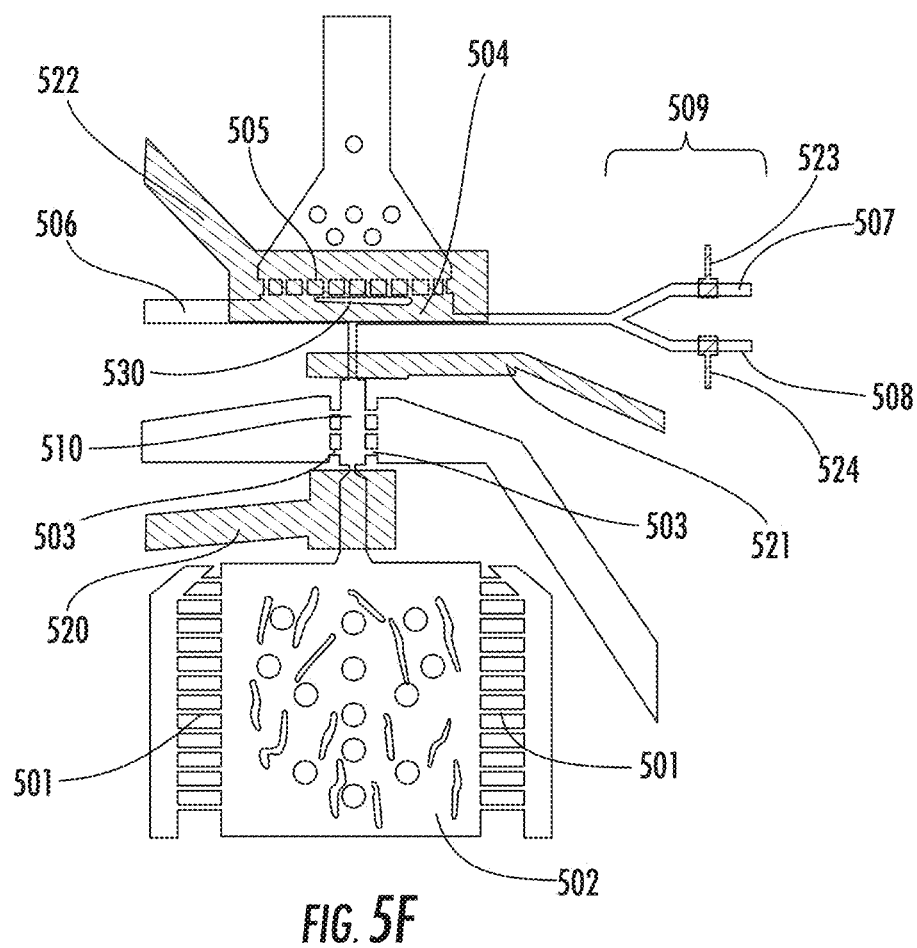

After the worm (530) is injected into the trapping chamber (504), valve 522, positioned over the trapping chamber (504), is closed in a pumping manner (repeatedly opened and closed before finally being closed) so as to avoid unfavorable folding of the worm against the sieve structure (505) fluidly connected to the trapping chamber (504) (FIG. 5F). When closed, valve 522 traps and flattens the worm (530) against the sieve structure (505) fluidly connected to the trapping chamber (504).

Figure 5G:
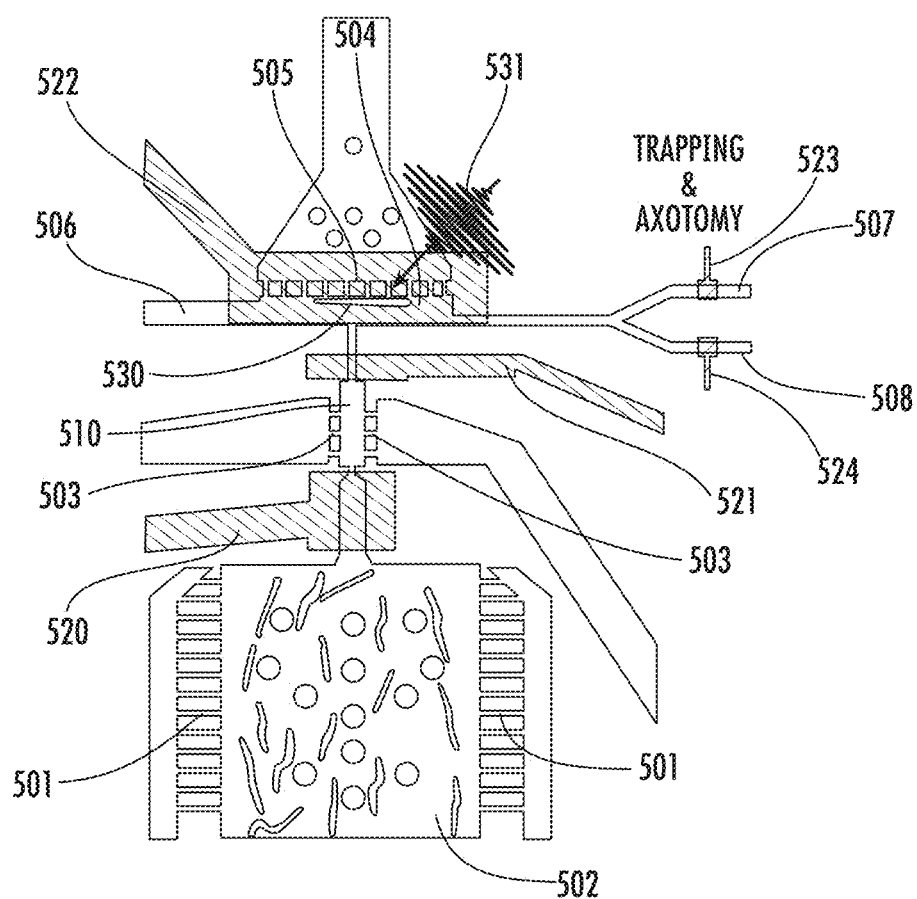

Once the worm (530) is positioned within the trapping chamber, the automation process proceeds to locate the worm body via image processing algorithms, a translation stage moves the field of view (FOV) to the center of the worm body, the objective is switched from 5× to 63×, and the white light source is turned off to proceed with the automated surgery. Then the automation software proceeds to positioning the neuronal cell body (soma), focusing and targeting the axon via image processing algorithms, which are explained below. The laser axotomy is then automatically performed (531) (FIG. 5G).

Figure 5H:
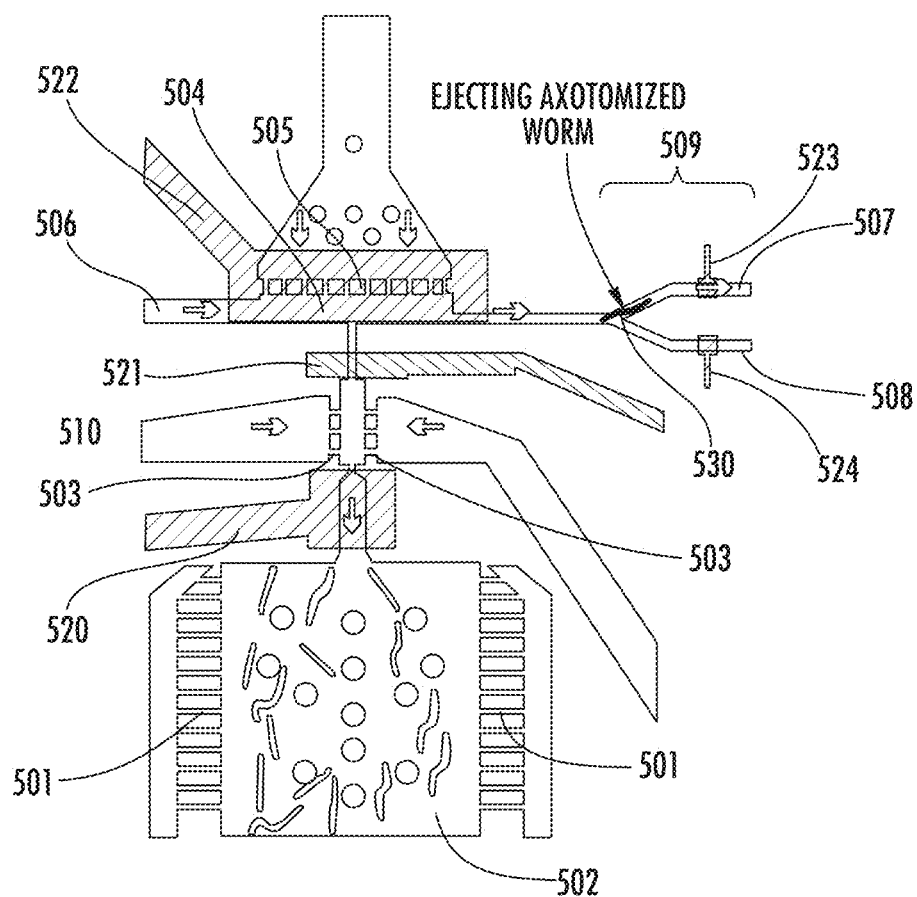

After finalizing the automated axotomy, the objective is switched back to 5×, the white light is turned on, and the software simultaneously actuates several valves to unload the worm (530) from the trapping chamber (504) via the exit area (509) (FIG. 5H). This process involves opening the valve in the trapping chamber (522) and either the valve (523) controlling fluid flow through the first microfluidic channel in the exit area (507) or the valve (524) controlling fluid flow through the second microfluidic channel in the exit area (508). One of these microfluidic channels connects to a vessel to collect worms on which successful axotomies are performed, while the second microfluidic channel connects to vessel to collect worms on which the axotomy procedure is unsuccessful (which are subsequently discarded). Flow through the sieve structure (505) fluidly connected to the trapping chamber (504) is reversed to push the worm away from the sieve structure against which it is fluidly restricted. Fluid flow is then initiated through a fluid inlet (506) fluidly connected to the trapping chamber (504) to push the worm (530) from the trapping chamber (504) out through the exit area (509). In addition, fluid flow through the sieve structures (503) fluidly connected to the staging chamber (510) is reversed to flow back towards the loading chamber (502) so as to prevent clogging at the intersection of the loading chamber and the staging chamber in anticipation of the next cycle.

The cycle is then repeated by staging a second worm (FIG. 5C) and proceeding throughout the cycle. For the entire duration of the automated platform operation, a constant head pressure of ~15 kPa is used to continually drive flow through the loading chamber and move worms into the staging chamber.

The automated process is repeated until axotomies are performed on the desired number of worms. The rest of the worms loaded into the device can then be removed from the chip by opening the valves (520), (521), and (522), and reversing the flow through the sieve structure (505) fluidly connected to the trapping chamber (504) towards one of the exit microfluidic channels dedicated for collecting worms on which the axotomy procedure is not performed, which are subsequently discarded).

The entire process of valve actuations and fluid flow used to serially deliver samples to the trapping chamber is automated, and controlled by software.

Automated Laser Axotomy

Image processing methodologies can be used to automatically perform laser axotomies on worms within the trapping chamber. Also provided are software, as well as signal processing circuitry and/or processors, configured to perform axotomies automatically on the microtubule ALM neuron of a *C. elegans* worm.

The software executes a five step procedure: (1) identify the location and center of the worm body in the trapping chamber within the region of interest (ROI); (2) identify a cell body within the field of view (FOV); 3) identify if the cell body the neuron of interest to be severed and focus coarsely on its soma; (4) focus finely on the targeted axon and move along it to the location of the laser focal point for precise axotomy; and (5) perform ablation and verify that the axon is cut successfully.

Step 1: Identification of the Worm Location and Center

In step 1, an image processing algorithm based on background subtraction and thresholding is used to identify the worm's position within the trapping chamber, and bring the worm to the center of the high magnification (63×) field of view (FOV) for performing high-resolution fluorescence imaging of the green fluorescent protein—GFP labeled neurons and fine focusing on the axons.

An image of the worm is captured at low magnification, and compared with a baseline image of the same and empty trapping chamber with the valve membrane deflected. The baseline image is subtracted from the image of the trapped worm, leaving only the worm in the processed image.

A binary thresholding is then applied to the subtracted image to identify the worm location as the object of interest. The image processing algorithm automatically defines the optimal threshold value as eight times the mean intensity of all the pixels in the processed image.

A Region-of-Interest (ROI) is then extracted from the processed image. A particle filter is used to filter out any arbitrary area within the ROI that has a total number of pixels that is smaller than 300. With this information, the 63×FOV could be sensibly moved to the expected location of the neuron of interest based on the known anatomy of the worm. In this specific case, our neuron of interest is one of the mechanosensory neurons, ALM—anterior lateral microtubule neuron that is located close at the center of the worm. If the detected center of the worm is not located in the pre-determined ROI (defined as the borders of the trapping area) or the centroid is found to be on the borders of the ROI, the trapping area is flushed and software proceeds with staging a single worm in the staging area.

Other suitable methods for the identification of the worm location and center of its body can also be used. For example, a low magnification fluorescence image can be obtained to image all of the GFP labeled mechanosensory neurons and locate the neuron of interest based on the known anatomy of the worm. With the aid of fluorescence microscopy and known anatomy, the relative location and head-tail orientation can be determined. Machine learning algorithms can also be used for the identification of the worm location and center of its body. By obtaining a library of different features of the nematode visualized in the white-light imaging (e.g., the contrast difference between head and tail, the shape of vulva, etc.), the orientation and the relative location of the worm can be determined.

Steps 2: Automated Identification of a Cell Body in the Small FOV

Step 2 in the flow chart involves a coarse focusing for identifying a cell body within the small FOV. Coarse focusing can be automatically performed. After the approximate location of a cell body (expected to be the ALM neuron) is determined in step 1, a 63× lens is moved into place, with the focal plane positioned close to the worm-glass interface. Fluorescence illumination is then applied. A translation stage can then be used to advance the focal plane in the z-direction into the worm in small (e.g., 2.5 µm) increments. This process is repeated as the focal plane moves towards an in-focus location of the ALM neuron, ALML or ALMR whichever is closer to the glass interface, until a circular shape is detected, corresponding to the cell body.

To carry out the cell body detection, the software collects fluorescence images of the GFP-labeled neurons at each 2.5 µm z-step, and thresholds them to a pre-determined intensity cutoff. In some embodiments, the pre-determined intensity cutoff is 8 times of mean intensity of the whole image at each individual z location. The cutoff was determined empirically until the software could successfully detect a cell body. Then the software program finds objects that can fit in a circle. The cell body detection is claimed when the circle has a radius that is between 2-6 µm. If the software program cannot detect a cell body in the FOV or the centroid is located at the edges of the FOV during a pre-determined number of iterations, the trapping area is flushed and software proceeds with staging a single worm in the staging area.

After locating the cell body, the program then translates the stage to bring the cell body to the center of the 63×FOV and performs fine focusing on the targeted neuron.

Step 3: Automated Verification of Neuron of Interest

Figure 9:
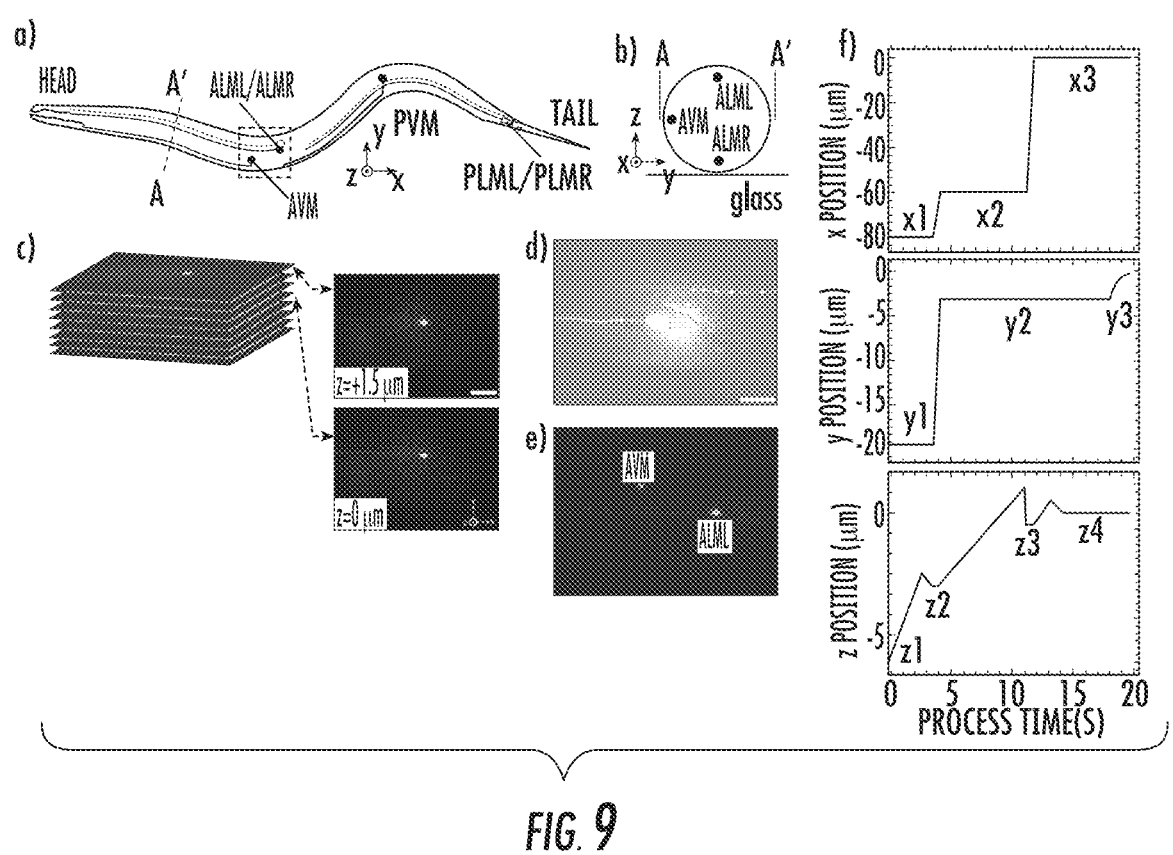
FIG. 9 illustrates the image processing methodology used to automatically perform laser axotomy on a *C. elegans* worm located in the trapping chamber of the microfluidic sample processing element shown in FIG. 5A. It specifically illustrates step 3 and step 4 in the automation process as described in the flow chart presented in FIG. 6, to verify if the detected cell body is the neuron of interest (ALM), then to identify the orientation of the worm, and finally to perform the axotomy in the desired location of the ALM axon. Panel A illustrates a simplified *C. elegans* neural anatomy, including the relative anatomical locations of the neurons of interest (i.e., ALM and PLM). Panel B illustrates a simplified cross-sectional view of a worm, including the positions of the ALM (or PLM) axons relative to each other and the AVM (or PVM) axon if the worm is positioned on its side. Panel C shows a typical z-stack obtained during fine focusing using the piezoelectric actuator with step size of 0.5 µm. The desired focal plane is determined by the image with the highest variance value. Two selected images from this stack are included in Panel C to show different degrees of focus. The scale bar is 20 µm. Panel D presents the method for verifying if the cell body is the ALM—the neuron of interest. This verification is achieved by looking if the cell body has a straight edge on one of its sides. The ALM neuron anatomy shown in Panel A has an axon sprouting from one of its sides. The orientation of the worm, namely the direction of its head and tail is then identified by the direction of the straight edge. Panel E shows an image of the location of the ablation after the software program translates the stage 60 µm in the x-direction away from the cell body along the axon where the final fine focusing is performed. Panel F is a plot of relative x, y, and z positions of axon with respect to the ablation spot as a function of time in the small FOV. Automation software first finds the centroid of the worm and moves the focus close to the glass/worm interface (x1, y1, z1); then locates a cell body using coarse focusing with the motorized stage at (x1, y1, z2); translates the stage in the x and y-directions to place the location of ablation on the cell body at (x2, y2, z2); using the piezo stage fine focuses the cell body to the plane of the axon to determine the neuron type and its orientation (x2, y2, z3), translates the stage 60 µm in the x-direction along the axon away from the cell body, to the approximate site of axotomy (x3, y2, z3); fine-focuses on the axon (x3, y2, z4); and moves the ablation spot onto the axon to perform axotomy (x3, y3, z4). After fine focusing, the shutter is opened to ablate the axon.

Fine focusing on the targeted neuron is then automatically performed. To determine the z-location of best focus, the variance of pixel intensity of each frame is used as the focusing function for direct image-to-image comparison from a z-stack collected at small increments of 0.5 µm steps using the piezoelectric actuator for translation (FIG. 9, panel C). The image with the highest variance of pixel intensity correlates to the most in-focus z-position. The sample variance of pixel intensity for each frame in the stack was defined as $$s_{MN}^2 = \frac{1}{MN} \sum_{i=1}^{M} \sum_{j=1}^{N} [I_{ij} - \bar{I}], \qquad (1)$$

where $I_{ij}$ is the intensity of a single pixel in the image and $\bar{I}$ is the average pixel intensity of an M×N array of pixels. Before the variance of intensity of each frame was calculated, a 2D Laplacian of Gaussian (LoG) bandpass filter was convolved with each image in order to simultaneously reduce high-frequency noise and enhance the intensity of the axon. The LoG-filtered image is given as:

$$f_{LoG(x,y)} = \nabla^2 g(x,y) * f_0(x,y), \qquad (2)$$

where $$\nabla^2 g(x, y) = \frac{x^2 + y^2 - 2\sigma^2}{\sigma^4} e^{-\left(\frac{x^2+y^2}{2\sigma^2}\right)}, \qquad (3)$$

$f_0(x, y)$ is the pre-filtered image.

By passing through the point of largest intensity variance, the optimal focus for performing axotomies is determined. After locating the device at the best focus, the automation program creates two small rectangular Region-of-Interests (ROI) on the left hand and right hand sides of the cell body to look for straight edges on each side to verify whether the soma found in the coarse focusing step is the neuron of interest. The relative location of the axon with respect to soma is also determined in this process. The existence of a straight edge is what differentiates the ALM neuron from the other nearby neuron, AVM. The AVM neuron does not have a straight edge on its right or left side that corresponds to an axon. If the software program does not detect straight edges in the vicinity of the detected cell body, the trapping area is flushed and software proceeds with staging a single worm in the staging area.

Step 4: Automated Axotomy

After determining the axon location by the side where the straight edge exists, the translation stage goes 60 µm in the corresponding direction along the axon.

In the final step before axon ablation, the axon-of-interest is brought to the focus of laser spot. For final fine focusing, the automation software collects z-stack images at 0.5 µm steps using the piezo-actuator four times and searches for the highest pixel intensity variance.

The piezoelectric actuator then moves to the precise y-position of the axon so that the axon is well aligned with the ablation target, given an axon diameter of ~300 nm. The $1/e^2$ diameter of the ablation spot is estimated to be ~620 nm. With the 63× objective, these dimensions correspond to three and six pixels respectively, giving a positioning tolerance for axotomy of approximately one pixel on either side of the axon. Due to the positioning hysteresis of the piezoelectric actuators, a closed-loop control algorithm is incorporated based on imaging to drive the actuators. Briefly, the CCD captures the focused image, and then processes the image to find the relative location of the axon in the y-axis. The distance on the image in pixels between the axon center and the ablation spot is converted into a physical distance based on pre-calibration. This distance serves as a feedback to the closed-loop control that commands the distance that the piezoelectric actuator translates. The process is repeated until the axon is within ~1 pixel from the ablation target. An axotomy could then be automatically performed. If the software program cannot align the ablation spot on the axon during a pre-determined number of iterations the trapping area is flushed and software proceeds with staging a single worm in the staging area.

Also provided are microfluidic sample processing elements designed to trap and/or process multiple unique populations of model organisms in parallel while maintaining segregation between the populations. Such sample processing elements can contain a plurality of trapping chambers or trapping regions, allowing for multiple model organisms to be trapped an analyzed simultaneously.

Figure 13:
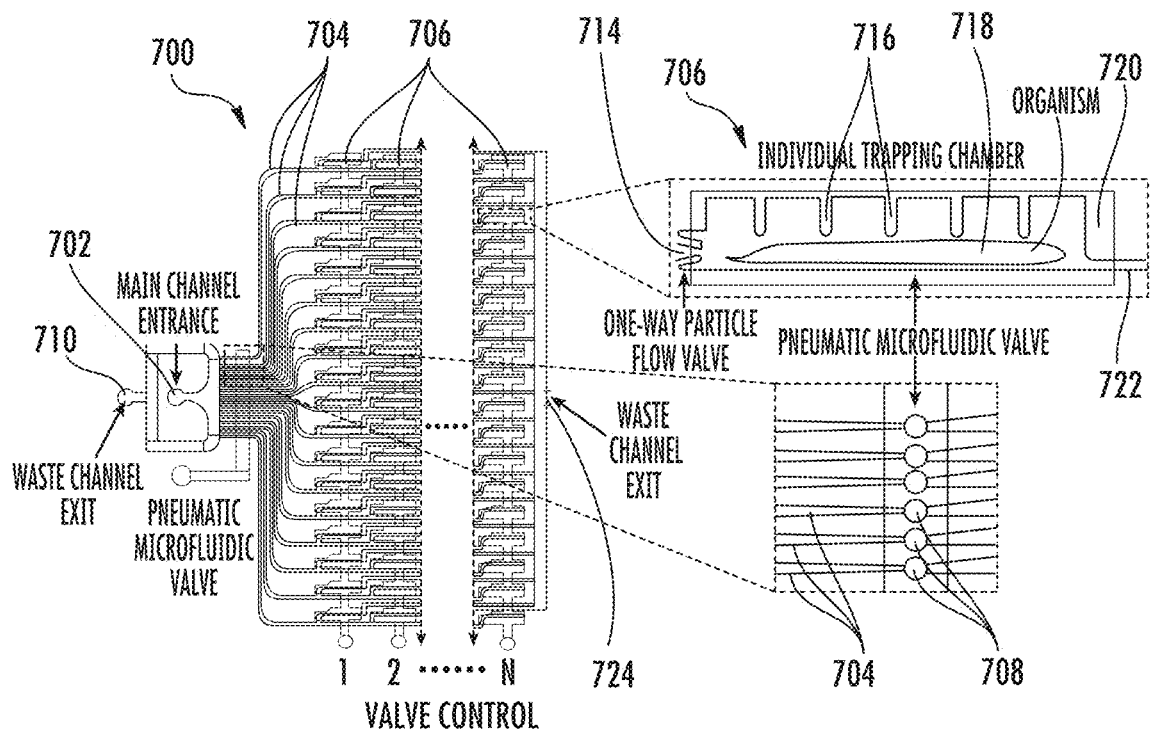
FIG. 13 is a schematic illustration of a microfluidic sample processing element designed to trap and/or process multiple unique populations of model organisms in parallel while maintaining segregation between the populations. The element includes an array of trapping chambers for housing individuals from organism populations. A population of model organisms can be delivered into the sample processing element via the main channel inlet. From the main channel inlet, individual organisms are directed into individual trapping chambers by way of outlet channels. The trapping chambers can confine individual organisms with a series of protrusions, a valve configured to restrain the organism within the trapping chamber, a one-way particle flow valve, and/or a small tapered exit channel.

An example sample processing element designed to trap and/or process multiple unique populations of model organisms in parallel while maintaining segregation between the populations is illustrated in FIG. 13.

The sample processing element (700) can comprise a main channel inlet (702), a plurality of outlet channels (704) fluidly connected to the main channel inlet (702), and a plurality of trapping chambers (706) fluidly connected to each of the outlet channels (704). The sample processing element (700) can further include one or more valves (708) positioned along each outlet channel (704) to regulate fluid flow through the outlet channels.

In some embodiments, the one or more valves (708) positioned along each outlet channel (704) are configured to form a multiplexer, as described above, which can selectively and sequentially direct each population of model organisms from the main inlet channel into a predetermined outlet channel. For example, in some embodiments, each outlet channel (704) fluidly connects with the main channel inlet (702) to form an intersection. At least a first valve and a second valve can be positioned along each outlet channel (704) to regulate fluid flow through the outlet channel (704), with the first valve being positioned in proximity to the intersection of the outlet channel and the main channel inlet. The first valve and the second valve can be configured to be independently operable. The plurality of valves positioned along the outlet channels in the sample processing element can be configured such that operation of one or more of the plurality of valves selectively directs fluid flow through a predetermined outlet channel in the sample processing element.

The dimensions of the channels, orientation of the channels, position of the valves, nature of the valves, and combinations thereof in the sample processing element can be selected to be identical or similar to those described for the multiplexer microfluidic devices and sample processing elements above. For example, in some embodiments, the main inlet channel, outlet channels, or combinations thereof have a height and a width. In some embodiments, the main inlet channel, outlet channels, or combinations thereof independently have a height that ranges from about 0.1 micron to about 1000 microns (e.g., from about 1 micron to about 750 microns, from about 1 micron to about 500 microns, from about 100 microns to about 750 microns, from about 5 microns to about 500 microns, or from about 5 microns to about 150 microns). In some embodiments, the main inlet channel, outlet channels, or combinations thereof independently have a width that ranges from about 1 micron to about 1000 microns (e.g., from about 1 micron to about 750 microns, from about 1 micron to about 500 microns, from about 100 microns to about 750 microns, from about 5 microns to about 500 microns, or from about 5 microns to about 150 microns).

The sample processing element can contain any number of outlet channels and trapping chambers. In general, in number of outlet channels and/or the number of trapping chambers in view of the number of unique populations of model organisms being processed, the number of model organisms in each population, or combinations thereof. For example, in some embodiments, the number of outlet channels is selected in view of the number of unique populations of model organisms being processed by the sample processing element (e.g., the sample processing element includes at least one inlet channel for each population of organisms being processed, or the sample processing element includes an inlet channel for each population of organisms being processed). In some embodiments, the number of trapping chambers connected to each outlet channel is selected in view of the number of model organisms present in each population of model organisms being processed by the sample processing element (e.g., the number of trapping chambers connected to each outlet channel can be greater than or equal to the number of model organisms present in each population of model organisms being processed by the sample processing element).

Referring again to FIG. 13, each of the plurality of trapping chambers (706) can comprise a one-way particle valve (714) configured to control the flow of a multicellular organism (718) between the outlet channel (704) and the trapping chamber (706), and an exit channel (722) fluidly connected to the trapping chamber (706).

In some embodiments, the height and width of the exit channel (722) are selected in accordance with the dimensions of the multicellular organisms, such that the multicellular organisms cannot pass from the trapping chamber into the exit channel under pressure-driven flow. For example, in some cases, the exit channel can have a height and/or width which is less than the largest cross-sectional dimension of the shortest body axis of the organism being processed. In some cases, the height and/or width of the exit channel is less than about 75% (e.g., less than about 50%, or less than about 25%) of the largest cross-sectional dimension of the shortest body axis of the organism being processed. In some cases, the height, width, and length of the trapping chamber (706) are selected in accordance with the dimensions of the multicellular organisms, such that only one of the multicellular organisms can be present in the trapping chamber. For example, is come embodiments, the height, width, length, or combinations thereof of the trapping chamber can be selected to be identical or similar to those described for the staging chamber above.

The one-way particle valve (714) can be configured to control the flow of a multicellular organism (718) between the outlet channel (704) and the trapping chamber (706). The one-way particle valve can be any suitable microfluidic valve, including those described above, which can (either passively or as a consequence of valve actuation) allow a multicellular organism to pass from the outlet channel into the trapping chamber while minimizing the ability of or preventing the organisms which have entered the trapping chamber from passing from the trapping chamber to the outlet channel. See also, for example, U.S. Pat. No. 6,767, 194 to Jeon, et al, which is hereby incorporated by reference for its teaching of microfluidic valves.

In some embodiments, the one-way particle valve comprises two protrusions: a first protrusion extending from a first wall of the outlet channel, and a second protrusion extending from a second (opposite) wall of the outlet channel. In some cases, the first wall and the second wall are side walls of the outlet channel. The first wall and the second wall can also be the top and bottom of the outlet channel. In these cases, the one-way particle valve can comprise two protrusions which extend from opposite walls of the outlet channel. The protrusions can be configured (e.g., in terms of their dimensions and orientation) to have an orientation with respect to the side-walls of the outlet channel and an orientation with respect to one another (e.g., a gap between the distal end of the first protrusion and the distal end of the second protrusion) such that an organism can readily pass between the protrusions when traveling in a first direction (e.g., in a direction from the outlet channel to the trapping chamber); however, the organism cannot readily pass between the protrusions when traveling in a second direction (e.g., in a direction from the trapping chamber to the outlet channel). In some cases, the protrusions are configured such that the rate at which an organism passes between the protrusions in a first direction (e.g., in a direction from the outlet channel to the trapping chamber) is at least five times (e.g., at least ten times, at least fifteen times, at least twenty times, at least twenty-five times, at least thirty times, at least forty times, at least fifty times, at least seventy-five times, or at least one hundred times) the rate at which the organism passes between the protrusions in a second direction (e.g., in a direction from the trapping chamber to the outlet channel) in the absence of pressure applied to drive fluid flow through the valve.

In some embodiments, the gap (i.e., the distance) between the distal end of the first protrusion and the distal end of the second protrusion is at least about 10% (e.g., at least about 15%, at least about 20%, at least about 25%, at least about 30%, at least about 40%, at least about 50%, at least about 60%, at least about 70%, at least about 75%, at least about 80% or at least about 90%) of the largest cross-sectional dimension of the shortest body axis of the organism being processed by the device. In some embodiments, the gap (i.e., the distance) between the distal end of the first protrusion and the distal end of the second protrusion is less than about 200% (e.g., less than about 175%, less than about 150%, or less than about 125%) of the largest cross-sectional dimension of the shortest body axis of the organism being processed by the device. In certain embodiments, the gap (i.e., the distance) between the distal end of the first protrusion and the distal end of the second protrusion is less than the largest cross-sectional dimension of the shortest body axis of the organism being processed by the device.

The protrusions can be linear, meaning that they linearly extend from a wall into the outlet channel. In other cases, the protrusions may be curved in shape. In some embodiments, the length of the protrusions (as measured from the point at which they extend from the wall to their distal end) is at least about 5 microns (e.g., at least about 10 microns, at least about 15 microns, at least about 20 microns, at least about 25 microns. at least about 30 microns, or at least about 35 microns).

In certain cases, the protrusions extend from a wall into the outlet channel in the direction of the incoming fluid flow vector in the outlet channel during expected device function. For example, the protrusions can be configured such that the angle formed between the protrusion and the wall of the outlet channel downstream of point at which they extend from the wall of the outlet channel is less than about 90 degrees (e.g., less than about 80 degrees, less than about 70 degrees, less than about 60 degrees, less than about 50 degrees, less than about 45 degrees, less than about 40 degrees, or less than about 30 degrees).

The trapping chamber (706) can further include one or more immobilization elements configured to immobilize a multicellular organism (718) within the trapping chamber (706) in order to facilitate the manipulation and/or interrogation of the multicellular organism. Examples of suitable immobilization elements include, but are not limited to, a sieve structure fluidly connected to the trapping chamber configured to fluidly restrict a multicellular organism within the trapping chamber; a valve configured to mechanically restrict a multicellular organism within the trapping chamber; protrusions (for example, extending from one or more walls of the trapping chamber) configured to physically restrict a multicellular organism within the trapping chamber; a cooling element configured to decrease the temperature of the trapping chamber and decrease the motility of the multicellular organism; and combinations thereof.

Referring again to FIG. 13, in some embodiments, the trapping chamber further comprises a plurality of protrusions (716) extending from one or more side walls of the trapping chamber. In certain embodiments, the protrusions extend from a side wall which is oriented parallel to the direction of fluid flow through the outlet channel (704) at the point where it fluidly connects to the trapping chamber (706), oriented parallel to the direction of fluid flow through the exit channel (722) at the point where it fluidly connects to the trapping chamber (706), or combinations thereof.

In some embodiments, the length of the protrusions (as measured from the point at which they extend from the wall to their distal end) is at least about 5 microns (e.g., at least about 10 microns, at least about 15 microns, at least about 20 microns, at least about 25 microns. at least about 30 microns, or at least about 35 microns). The protrusions can leave a gap between the distal end of the protrusion and the opposite wall of the trapping chamber from the wall of the trapping chamber to which the protrusions extend that is greater than about 50% (e.g., greater than about 80%, greater than about 120%, greater than about 140%, greater than about 160%, greater than about 180%, greater than about 200%, greater than about 225%, greater than about 250%, or greater than about 275%) of the largest cross-sectional dimension of the shortest body axis of the sample being processed by the microfluidic device.

In some embodiments, the microfluidic sample processing element further comprises a valve (720) configured to mechanically restrict a multicellular organism (718) within the trapping chamber (706). In some embodiments, the valve is a pneumatic valve comprising a control layer positioned above the trapping chamber. The control layer can be separated from the trapping chamber by a deformable membrane. Upon application of pressure to the control layer, the deformable membrane can be deformed, impinging into the trapping chamber, and mechanically restricting a sample within the trapping chamber. The deformable membrane can be designed to be gas permeable to permit a gas, such as $CO_2$, to diffuse into the trapping chamber.

The sample processing element can further include one or more devices to manipulate and/or interrogate a sample configured so as to manipulate and/or interrogate a sample localized within one or more of the trapping chambers. Suitable devices to manipulate and/or interrogate a sample include those described for the sample processing elements described above.

The sample processing element (700) can further comprise one or more additional microfluidic features to facilitate device operation. For Example, a gasket system configured to pressurize one or more of the one or more sample reservoirs connected the main channel inlet (702) can be included. In some cases, the plurality of immobilization valves (720) in the device is fluidly connected to a single pneumatic input. Additional pneumatic valves can be positioned along the one or more channels coming out of the single pneumatic input to precisely control the individual valves (720) above a given trapping chamber. These additional valves will allow for the actuation any number or combination of the pneumatic valves (720) that will immobilize organisms in the trapping chambers. The sample processing element (700) can further comprise a waste channel (710) fluidly connected to the main channel inlet (702). In some embodiments, the exit channels (722) fluidly connected to each of the plurality of trapping chambers (706) are fluidly connected to a main exit channel (724). The sample processing element (700) can further include signal processing circuitry or a processor configured to actuate one or more valves in a predetermined fashion to selectively direct the multicellular organisms from the main channel inlet into the plurality of trapping chambers.

The main channel (702) of sample processing element (700) can be fluidly connected directly to a sample reservoirs (as described above and below), in which case sample processing elements of this type can be used as multi-trap microfluidic devices (see below). In these embodiments, the multi-trap microfluidic devices can include multiple sample reservoirs, each of which is fluidly connected to the main channel (702) of sample processing element (700).

Multi-Trap Microfluidic Devices

Also provided are multi-trap microfluidic devices which provide for the simultaneous, parallel loading of multiple populations of organisms. The multi-trap microfluidic devices can include one or more sample reservoirs into which a sample population can be loaded, and a sample processing element fluidly connected to each sample reservoir which is configured to trap, house, interrogate, process, manipulate, and/or actuate members of each population in parallel. This can allow for multiple model organisms in a population to be, for example, housed, trapped, and/or analyzed simultaneously.

Multi-trap microfluidic devices can be designed to trap and/or process multiple unique populations of model organisms in parallel while maintaining segregation between the populations. In this way, multi-trap microfluidic devices can significantly reduce experimental time, and compartmentalization of specific populations eliminates the risk of cross-contamination by other animal populations being studied simultaneously using the same device. Moreover, without the need to transport the animals to multiple locations on the devices, screening time can be significantly reduced. Because genetic screening requires an enormous number of individual animals, as for example in regards to the study of the genetic component of axonal recovery or degradation following injury, efficiency and reduced error rates are paramount. The automated aspect of the system allows for minimal involvement by lab technicians and researchers, and multiple systems can be set up in parallel to further reduce screening times.

The multi-trap devices can contain any number of sample reservoirs and sample processing elements, so as to be capable of accommodating any number of sample populations. The dimensions of the sample reservoirs, orientation of the sample reservoirs, and combinations thereof in the device can be selected to be identical or similar to those described for the multiplexer microfluidic devices described above. For example, the sample reservoirs can comprise microwells that can be arranged in a variety of geometries depending upon the overall shape of the device. In certain embodiments, the device comprises an array of microwells arranged in a 2:3 rectangular matrix, so as to form a microwell plate (also known as a MICROTITER® plate). In some cases, the device has a total of 6, 24, 96, 384, 1536, 3456, or 9600 microwells arranged in a 2:3 rectangular matrix. In certain embodiments, the device comprises from 6 to 9600 microwells (e.g., from 6 to 384 microwells, or from 6 to 200 microwells).

The multi-trap microfluidic device can include one or more sample reservoirs, and an array of multiple trapping chambers to house and immobilize individual organisms fluidly connected to each sample reservoir (e.g., via an inlet channel). The trapping chambers can be T-shaped (as described above), rectangular shaped (as described above), triangularly shaped, square shaped, oval shaped, or circularly shaped, and can optionally include a sieve structure located at their output (i.e., fluidly connected to the trapping chamber opposite from the point where the organism enters the trapping chamber).

Figure 15:
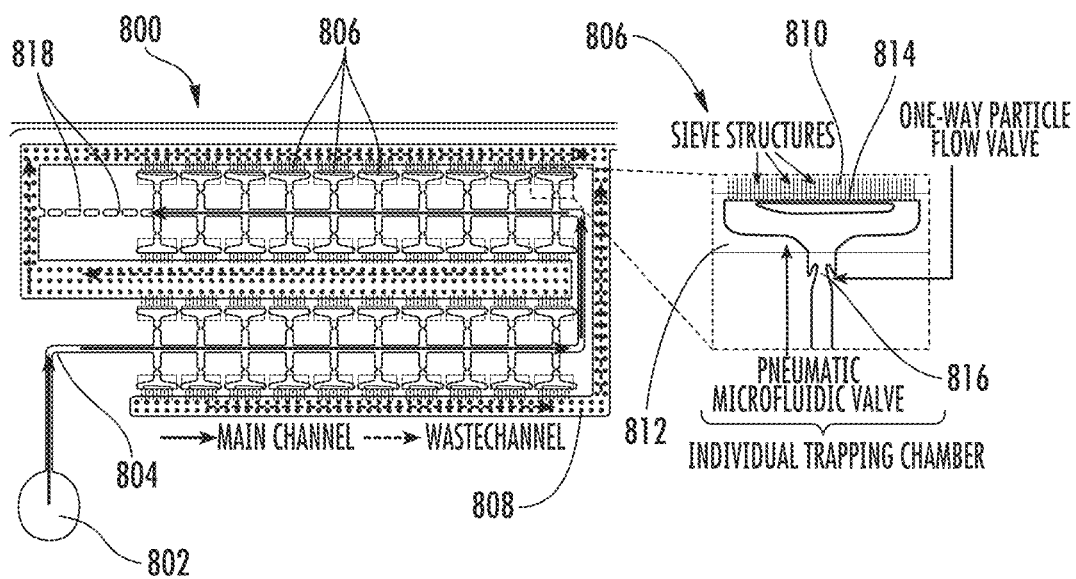
FIG. 15 is a schematic illustration of an example multi-trap microfluidic device which includes individual animal trapping chambers. A main channel interfaces with trapping chambers and a waste channel. Individual trapping chambers house single organisms from the loaded population, and they are immobilized by the microfluidic valve for interrogation steps and confined inside the chamber throughout the experiments via the sieve structures and the one-way particle flow valve.

An example multi-trap microfluidic device is illustrated in FIG. 15. The device (800) can contain one or more sample reservoirs (802), an inlet channel (804) fluidly connected to each sample reservoir (802), a plurality of trapping chambers (806) fluidly connected to each inlet channel (804), and a waste channel (808) fluidly connected to each of the trapping chambers (806).

The dimensions of the channels, orientation of the channels, and combinations thereof in the device can be selected to be identical or similar to those described for the multiplexer microfluidic devices and sample processing elements above. For example, in some embodiments, the inlet channels, waste channel, or combinations thereof have a height and a width. In some embodiments, the inlet channels, waste channel, or combinations thereof independently have a height that ranges from about 0.1 micron to about 1000 microns (e.g., from about 1 micron to about 750 microns, from about 1 micron to about 500 microns, from about 100 microns to about 750 microns, from about 5 microns to about 500 microns, or from about 5 microns to about 150 microns). In some embodiments, the inlet channels, waste channel, or combinations thereof independently have a width that ranges from about 1 micron to about 1000 microns (e.g., from about 1 micron to about 750 microns, from about 1 micron to about 500 microns, from about 100 microns to about 750 microns, from about 5 microns to about 500 microns, or from about 5 microns to about 150 microns).

As discussed above, the dimensions of the sample reservoirs, orientation of the sample reservoirs, number of sample reservoirs, or combinations thereof in the sample processing element can be selected to be identical or similar to those described for the multiplexer microfluidic devices described above.

Referring again to FIG. 15, the device (800) can further comprise a waste channel (808) fluidly connected to each of the inlet channels (804) downstream from the plurality of trapping chambers (806) that are fluidly connected to the inlet channel. One or more valves (818) can be positioned along each of the inlet channels (804) downstream from the plurality of trapping chambers (806) that are fluidly connected to the inlet channel, such that the valves (818) are configured to control the flow of the multicellular organisms from the inlet channel (804) to the waste channel (808). The one or more valves (818) can be any suitable microfluidic valve described above. In certain embodiments, the one or more valves (818) are one-way particle valves, including those described above, which can (either passively or as a consequence of valve actuation) allow a multicellular organism to pass from the inlet channels (804) into the waste channels (808) while minimizing the ability of or preventing organisms which have entered the waste channels (808) from passing from the waste channels (808) to the inlet channels (804). In some embodiments, the waste channels connected to each of the trapping chambers and the waste channels fluidly connected to each of the inlet channels downstream from the plurality of trapping chambers are fluidly connected to a main exit channel.

Referring again to FIG. 15, each of the plurality of trapping chambers (806) can include a one-way particle valve (816) configured to control the flow of a multicellular organism (814) between the inlet channel (804) and the trapping chamber (806). Each of the plurality of trapping chambers (806) can also include a valve (812) configured to mechanically restrict the multicellular organism (814) within the trapping chamber (806).

The height, width, and length of the trapping chamber can selected in accordance with the dimensions of the multicellular organisms, as described above with respect to other portions of sample processing elements, such that only one of the multicellular organisms can be present in the trapping chamber. For example, the dimensions of the trapping chamber can be selected to be identical or similar to those described for the staging chamber of the sample processing element described above. In these cases, as each trapping chamber fills up with a single organism, excess organisms are flushed out of the inlet channel (804) into the waste channel (808).

Referring again to FIG. 15, each of the plurality of trapping chambers (806) can further comprise a sieve structure (810) fluidly connected to the trapping chamber (806). The sieve structure (810) can fluidly connect the trapping chamber (806) to the waste channel (808). The sieve structure (810) can comprise fluid flow paths that fluidly connect the waste channel (808) to the trapping chamber (806), each fluid flow path having a height, width, and length selected in accordance with the dimensions of the multicellular organisms (814), such that the multicellular organisms cannot pass through the fluid flow path. In some embodiments, the fluid flow paths are configured to fluidly restrict the multicellular organism (814) within the trapping chamber (806). Optionally, the trapping chamber can further include a plurality of protrusions configured to immobilize a sample within the trapping chamber in order to facilitate the manipulation and/or interrogation of the sample. For example, in some embodiments, a plurality of protrusions can optionally extend from the wall of the trapping chamber to which sieve structure 810 is fluidly connected.

The device (800) can further include one or more devices to manipulate and/or interrogate the sample configured so as to manipulate and/or interrogate a sample localized within one or more of the trapping chambers. Suitable devices to manipulate and/or interrogate the sample include those described for the sample processing elements described above.

The device (800) can further comprise one or more additional microfluidic features to facilitate device operation. For example, the device (800) can further comprise a gasket system configured to pressurize one or more of the one or more sample reservoirs (802). In some cases, the plurality of pneumatic valves (812) for mechanical restriction of the organisms is fluidly connected to a single pneumatic input. Additional pneumatic valves can be positioned along one or more of the channels coming out of the single pneumatic input to precisely control the individual valves (812) above a given device unit. These additional valves will allow for the actuation any number or combination of the pneumatic valves (812) that will immobilize organisms in the trapping chambers. The device (800) can further include signal processing circuitry or a processor configured to actuate one or more valves in a predetermined fashion to selectively direct multicellular organisms from the one or more sample reservoirs into the plurality of trapping chambers, control one or more devices to manipulate and/or interrogate a sample so as to manipulate and/or interrogate a sample localized within one or more of the trapping chambers in the device, or combinations thereof.

The multi-trap microfluidic device can include one or more sample reservoirs, and a main channel containing one or more trapping regions fluidly connected to each sample reservoir. The main channels can serve to house and immobilize a population of individual organisms. The one or more trapping regions of the main channel can include one or more immobilization elements, including those described above, configured to immobilize a multicellular organism within the trapping region in order to facilitate the manipulation and/or interrogation of the multicellular organism.

Figure 16:
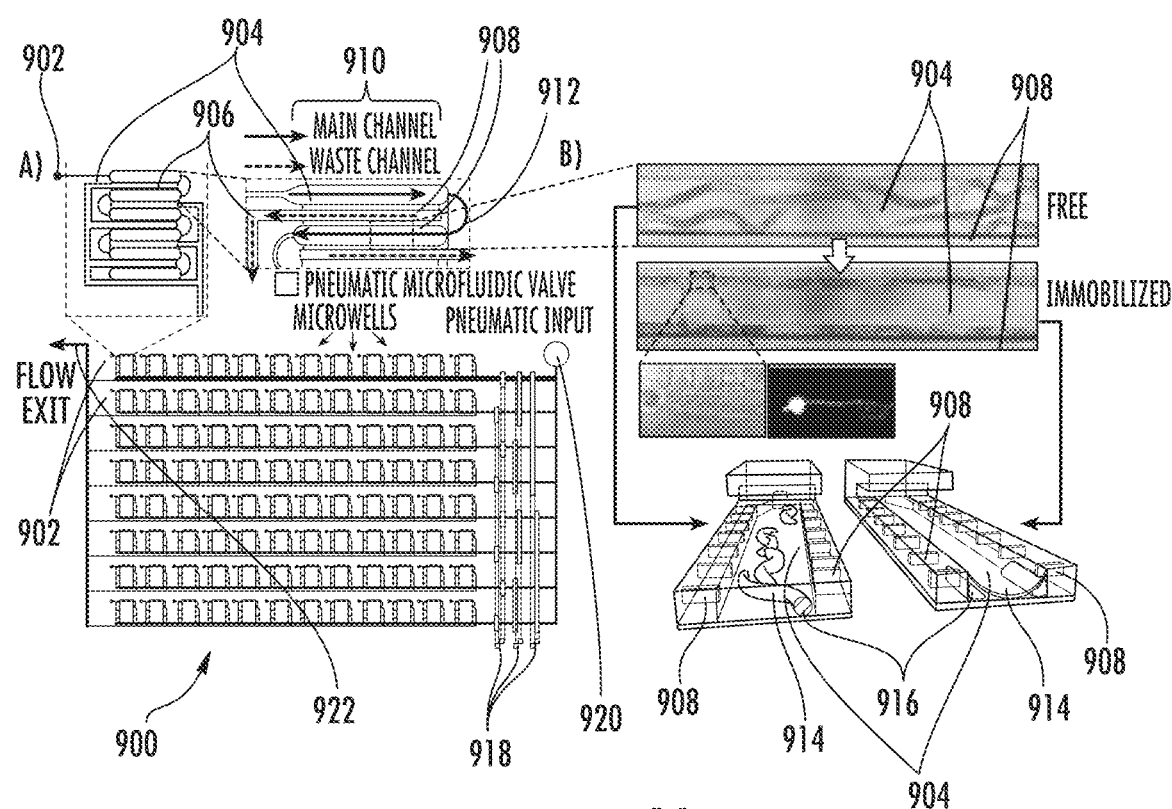
FIG. 16 is a schematic illustration of an example multi-trap microfluidic device which includes main channels containing a plurality of trapping regions. Multiple *C. elegans* worms can be loaded from a single population into each main channel, where they are free to reside and move freely prior to pressurization of the valves in the trapping regions of the main channel. The valves can be pressurized to immobilize the organisms for high resolution interrogation of individual organisms.
Figure 17:
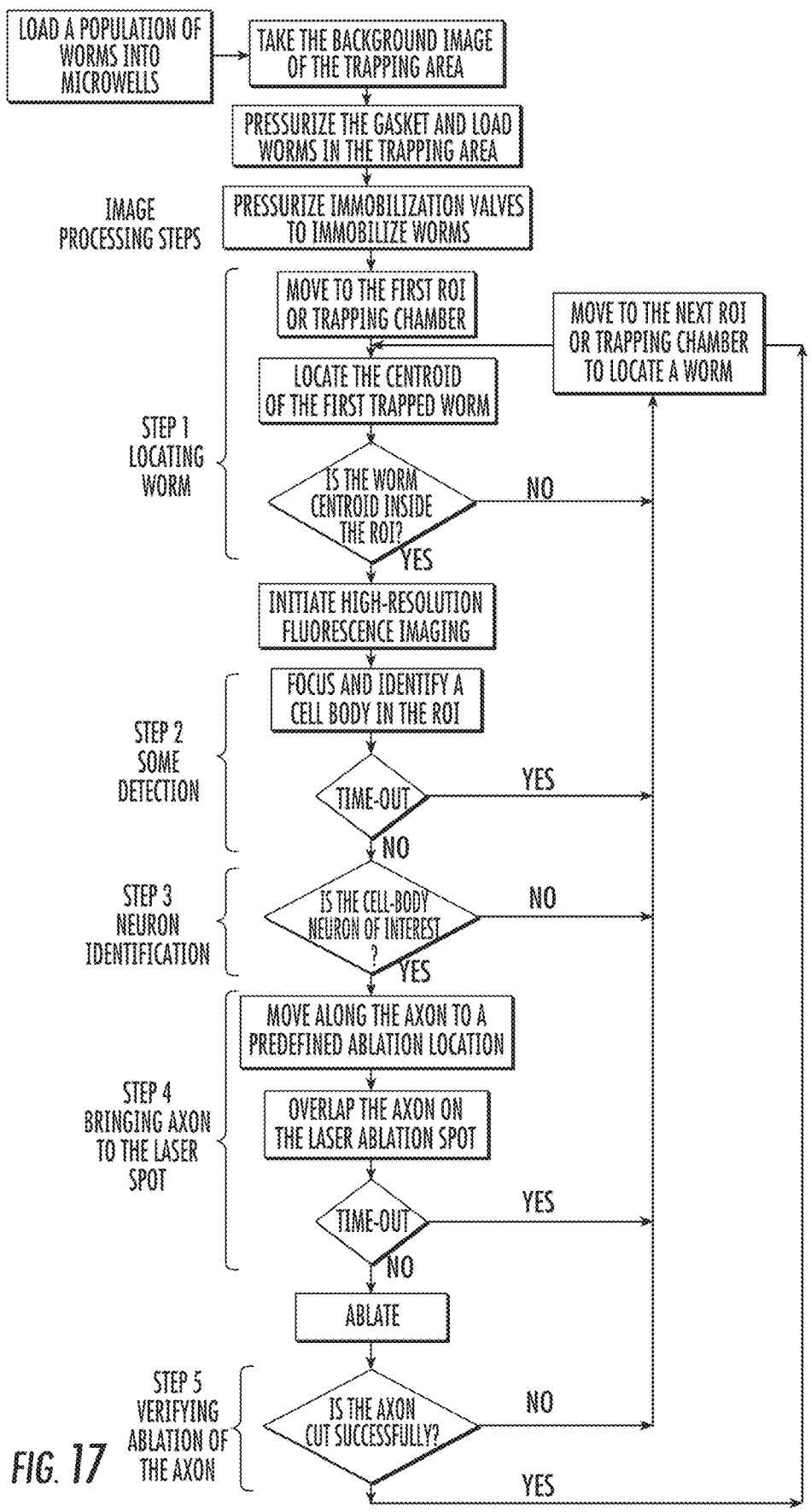
FIG. 17 shows an example of an automation flow chart for laser axotomy in a multi-trap microfluidic device.

An example multi-trap microfluidic device is illustrated in FIG. 16. The device (900) can contain one or more sample reservoirs (902), a main channel (904) fluidly connected to each sample reservoir (902), a waste channel (906) fluidly connected to each of the main channels (904), and a sieve structure (908) fluidly connecting the main channel (904) to the waste channel (906). The sieve structure (908) can comprise fluid flow paths that fluidly connect the waste channel (906) to the main channel (904), each fluid flow path having a height, width, and length selected in accordance with the dimensions of the multicellular organisms, such that the multicellular organisms (916) cannot pass through the fluid flow path.

The dimensions of the channels, orientation of the channels, and combinations thereof in the device can be selected to be identical or similar to those described for the multiplexer microfluidic devices and sample processing elements above. For example, in some embodiments, the main channels, waste channels, or combinations thereof have a height and a width. In some embodiments, the main channels can have a length that is no less than the longest cross-section of the organism being studied, and a width is at least four times longer than the longest dimension of the shortest cross-section of the organism being studied. In some embodiments, the main channels, waste channels, or combinations thereof independently have a height that ranges from about 0.1 micron to about 1000 microns (e.g., from about 1 micron to about 750 microns, from about 1 micron to about 500 microns, from about 100 microns to about 750 microns, from about 5 microns to about 500 microns, or from about 5 microns to about 150 microns). In some embodiments, the main channels, waste channels, or combinations thereof independently have a width that ranges from about 1 micron to about 1000 microns (e.g., from about 1 micron to about 750 microns, from about 1 micron to about 500 microns, from about 100 microns to about 750 microns, from about 5 microns to about 500 microns, or from about 5 microns to about 150 microns). The dimensions of the main channel can vary along its length.

Referring again to FIG. 16, each of the main channels (904) can comprises one or more trapping regions (910) and optionally one or more non-trapping regions (912). The one or more trapping regions (910) of the main channel can include one or more immobilization elements, including those described above, configured to immobilize a multicellular organism within the trapping region in order to facilitate the manipulation and/or interrogation of the multicellular organism. In some cases, the one or more trapping regions (910) further comprise a plurality of protrusions extending from a side wall of the main channel (904). The protrusions can extend from one or more of the side walls of the main channel. The protrusions can be configured to physically restrict the multicellular organism (916) within the trapping region (910).

In certain embodiments, the one or more trapping regions (910) further comprise a valve configured to mechanically restrict a multicellular organism (916) within the trapping region (910). In certain embodiments, the valves is a pneumatic valve comprising a control layer vertically stacked above or below the trapping region of the main channel that is not fluidly connected to the main channel, and is separated from the main channel by a horizontal, thin membrane (914). When the control channel is unpressurized, the trapping region is unobstructed, and organisms within the trapping region can move freely. When pressure is applied to the control channel, the membrane (914) deflects into the trapping region of the main channel (904) and immobilized the organisms within the trapping region (910).

The device (900) can further include one or more devices to manipulate and/or interrogate the sample configured so as to manipulate and/or interrogate a sample localized within one or more of the trapping regions of the main channel. Suitable devices to manipulate and/or interrogate the sample include those described for the sample processing elements described above.

The device (900) can further comprise one or more additional microfluidic features to facilitate device operation. For example, the device (900) can further comprise a gasket system configured to pressurize one or more of the one or more sample reservoirs (902). In some cases, the plurality of pneumatic valves (914) in the device are fluidly connected to a single pneumatic input (920). Additional pneumatic valves (918) can be positioned along one or more of the channels coming out of the pneumatic input (920) to precisely control the individual valves (914) above a given device unit. These additional valves (918) allow for the actuation of any number or combination of the pneumatic valves (914) that will immobilize organisms in the trapping chambers. The device (900) can further include signal processing circuitry or a processor configured to actuate one or more valves in a predetermined fashion to selectively direct multicellular organisms from the one or more sample reservoirs into the plurality of trapping chambers, control one or more devices to manipulate and/or interrogate a sample so as to manipulate and/or interrogate a sample localized within one or more of the trapping chambers in the device, or combinations thereof.

Microfluidic Device Fabrication

The microfluidic devices described herein can be fabricated using standard soft lithography techniques known in the art. See, for example, Unger, M. A., et al. Science, 288:113-116 (2000) and Thorsen, T., et al. Science, 298: 580-584 (2002).

Devices with microfluidic features can be fabricated from a number of materials including, but not limited to glass, SU-8 epoxy resin, polydimethylsiloxane (PDMS), polymethyl methacrylate (PMMA), polyurethane methacrylate (PUMA), theromset polyesters, polythiols, polyethylenes, polysilanes, and other polymers known in the art. Several general methods exist to fabricate the devices including, but not limited to replica molding (e.g. soft-lithography), hot embossing, injection molding, mechanical micromachining, and laser micromachining.

The present invention will be further understood by reference to the following non-limiting examples.

EXAMPLES

Example 1: Multiplexer Microfluidic Device for the Delivery of Worm Populations

A multiplexer microfluidic device configured to rapidly and automatically deliver multiple populations of *C. elegans* worms to a sample processing element was fabricated. The microfluidic device utilized multiplexed valve control, in which a series of pneumatically actuated microfluidic valves were configured to regulate flow of fluid containing the worms from cone-shaped reservoirs through on-chip microchannels. The cone-shaped reservoirs were designed to have dimensions, including diameters at their top surface, which are consistent with the dimensions of microwells in standard 96-well microplates. By using this on-chip valve arrangement and multiplexer architecture, the delivery of *C. elegans* worm populations from sixteen wells can be achieved without mixing of the populations by actuating only eight pneumatic valves.

Pneumatically activated microfluidic valves arranged according to the multiplexer architecture effectively increase experimental throughput per unit area of device footprint in automated microfluidic devices. This system of pneumatically driven microfluidic valves seals off or releases flow through various channels in the device. Depending on the number of channels one wishes to control, the device logic used, and the overall microchannel layout, the total number of pneumatically activated microfluidic valves required to control fluid traffic in the individual channels can be orders of magnitude fewer than the number of flow channels. Reducing the number of valves implies that a relatively simple setup can control and automate the handling of 100's or 1000's of samples loaded in the chip. Related microfluidic multiplexers have been described in the art. See, for example, Thorsen, T. et al. Science, 298:580-584 (2002), U.S. Pat. No. 7,143,785 to Maerkl, S. J., et al., and U.S. Patent Application Publication No. US 2011/0136252 to Tseng, H. R. et al. The microfluidic multiplexer device can effectively segregate and deliver sixteen different worm populations to a sample processing element in a rapid and automated fashion.

Figure 1D:
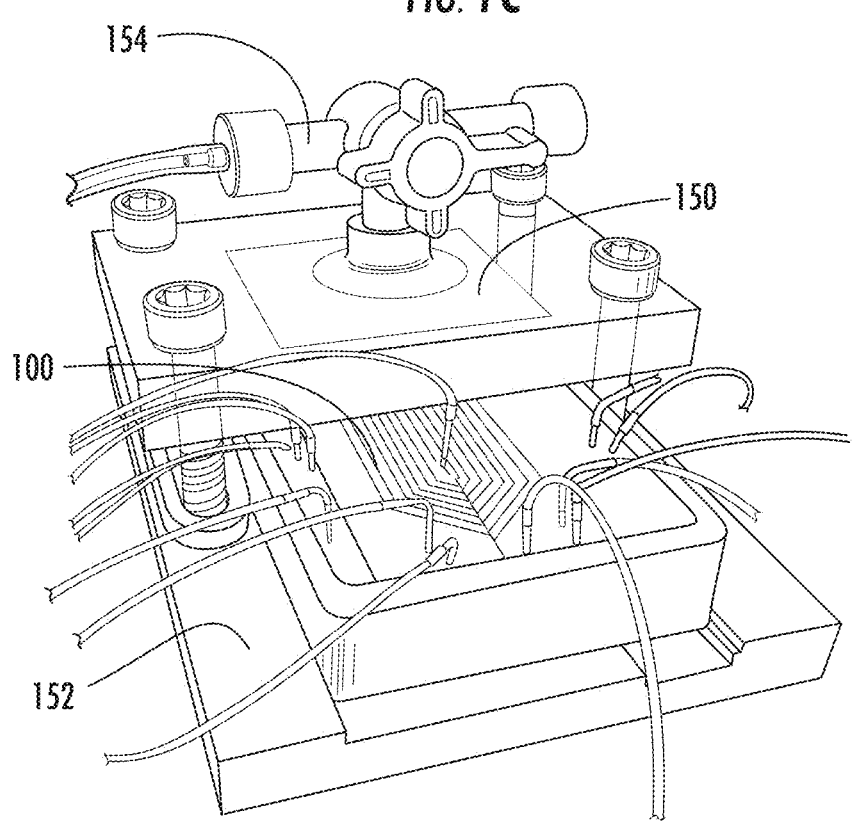
FIG. 1D shows the gasket system that was employed to pressurize the microwells of the multiplexer microfluidic device illustrated in FIG. 1A and provide a structure to hold the whole system.

The experimental setup also included pressure gauges, computer-controlled solenoid valves, fluid reservoirs, and the microfluidic device acting in concert to automate the delivery of different worm populations without mixing. A gasket system made of PMMA was employed to pressurize the microwells by sandwiching the microfluidic device with screw clamps (FIG. 1D). As pressure was applied to the microwells through the gasket, signal processing circuitry running an automation program opened and closed specific pneumatic valves to sequentially direct fluid flow out of a given microwell (see FIGS. 2A-2E). Once a microwell's sample population was delivered, fluid flow was reversed back to the microwell via pressurized flow from a fluid inlet to back wash any excess worms into their initial position and prevent sample cross-contamination. The microfluidic architecture and the sequence in which microwells were emptied also aided in preventing population mixing. In the main channel, worms flowing from an inlet channel would only pass by an inlet channel fluidly connected to microwells that had already delivered their sample populations.

The multiplexer microfluidic device produced fast, robust, and reliable worm population delivery. The device proved capable of extremely fast off-chip delivery of worms from the on-chip wells (~100-200 worms in under 5 seconds) with no drop-off in worm viability relative to control. By interfacing worms in liquid suspension (M9) via micropipette with fluid-primed microwells integrated into the device, bubbles were almost completely eliminated during device operation. The device could sequentially deliver sixteen populations through the main channel exit based on the pressure and timing used for worm delivery.

Materials and Methods

Device Fabrication

The microfluidic device was fabricated using standard soft-lithography techniques. Two molds patterned in photoresist on a silicon wafer were used to pattern the two layers of microchannels in the PDMS device. The "flow layer", which contained the worms, required two photolithography masks to pattern positive photoresist (AZ50-XT, Applied Electronic Materials Inc.) features and negative photoresist (SU-8 2025, Microchem Corp.) features. The positive resist was patterned wherever the flow layer overlapped with channels in the "the control layer," which was beneath the "flow layer". This arrangement effectively created on/off valves that seal via deformable membrane in these overlap regions. By ramping up the mold to 125° C. and keeping it there for 3.5 minutes, semi-circular curved channel cross-sections were formed in the positive resist. The curved geometry ensured that the valves would completely seal the channels in these locations. The average height of the "flow layer" was ~55 µm. The control layer mold, which serves as the template for the channels that actuate the on-chip valves, was also patterned using a single mask and negative photoresist. The control layer mold was ~36 µm tall.

The molds to pattern features into the elastomer (polydimethylsiloxane, PDMS, Dow Corning). PDMS mixed at a 10:1 base agent to curing agent ratio was poured onto the flow layer mold, which had conical P-1000 pipette tips pre-positioned on its well entrance ports by a PMMA holder surrounding the wafer. The pipette tip holder was supported with a PMMA barrier, which surrounded the photoresist mold and allowed a ~1.4 cm thick layer of PDMS to be poured onto the mold. The flow layer piece was then cured and demolded.

Fluidic access holes were then punched in the appropriate locations. A layer of PDMS was then spin-coated onto the control mold to create on-chip valves that were ~20 µm thick. This layer with the mold was placed in a 65° C. oven until the spin-coated PDMS was partially cured. The PDMS flow layer piece was then bonded to the control layer via oxygen plasma treatment, and allowed it to sit in the 65° C. oven overnight for bond strengthening. Oxygen plasma treatment enhanced bonding between the flow layer piece and the partially cured surface PDMS on the control layer mold. After this process the flow and control layers were removed as one piece. Fluid access holes were drilled into the device. The entire device was then bonded to a sheet of 3/16" thick borosilicate glass via oxygen plasma treatment. The device was then left in 65° C. for at least 4 hours to enhance the glass to PDMS bonding.

Valve Control

The pneumatic control setup consisted of sixteen computer controlled three-way solenoid valves (The Lee Company) controlled through a voltage amplifier (ValveLink 8.2, Automate Scientific Inc.) via an NI-DAQ 6501 controller board (National Instruments), which was connected to a computer through a USB port. DI water was fed into the on-chip valve inlets and M9 solution into the fluid inlets through the solenoid valves, which were fluidly coupled to the chip and air-pressurized fluid reservoirs. The three-way solenoid valves that fed pressurized fluid to the on-chip valves, were also hooked up to a vacuum (-60 kPa gauge pressure), so that the on-chip valve channels would be exposed to negative pressure when they were in the "off" or open position. This increased opening speed of the valves and led to faster on-chip responses to the automated control program.

A LabVIEW automation software was developed to control actuation of the solenoid valves, which control the pressure in the pneumatically activated microfluidic valves and delivery of pressurized air to the gasket and flush channel reservoirs for the timed delivery of worms sequentially from the on-chip microwells.

Device Fluid Priming

After securing all of the fluidic connections on the device, 100 µL of M9 solution was loaded into each on-chip microwell. The device was then sandwiched between a gasket (FIG. 1D, 150) and a chip holder (FIG. 1D, 152) using screws and washers to seal the microwell inlets to the gasket. The device was primed with fluid by inducing flow through the fluid inlet channels until there were no longer any bubbles coming into chip from their entrances. All of the on-chip valves, excluding those that block off the fluid inlet channels (these channels eventually lead to fluid reservoirs) were then opened, and the microwells were pressurized at 7.5-10 psi (~50-70 kPa). Once fluid completely filled the microchannels, valves 130 and 132 (FIG. 1A) were closed to block flow out of the chip, while pressure was applied (via a pressurized input line; FIG. 1D, 154) to the gasket in order to pressurize the fluid within the device to the point where air bubbles were forced to diffuse out of the bulk PDMS. This degassing procedure was performed for a short period, and after less than 10 minutes, all bubbles were removed from the device channels. All on-chip valves were then closed prior to sample loading.

The gasket was loosed to retrieve the chip for worm loading by first removing excess fluid from each of the microwells until ~10-20 µL of M9 solution remained. For fluidic flow rate experiments, the microwells could be filled with M9 via syringe or pipette. For worm delivery experiments, worms prepared in M9 suspension were loaded into the device at density of ~100-200 worms per on-chip well. After loading the wells, the gasket was sealed to the device again. The samples were incubated for approximately 5 minutes in the device to allow the worms to settle to the bottom of the wells prior to processing.

Measurement of Fluid Flow Rates

The device was primed with M9 solution so that there were no bubbles in the microchannels. The microwells were then filled with M9 solution. The valves were actuated using an automated valve sequence such that that fluid would pass from a specific microwell as different pressures were applied to the microwells for specified time periods. Fluid exiting the device via the downstream terminus of the main channel was collected in a fluid reservoir, and massed using a high-resolution scale (1 mg, Ohaus Inc.) immediately after sample collection to negate effects of evaporation.

Worm Culture Techniques

Preparing NGMSR Plates Seeded with Bacteria

Saturated cultures of HB101 *E. Coli* were grown by inoculating 250 mL of LB Broth, Miller (Fisher Scientific) with a single colony and incubating the culture for 24 h at 37° C. We seeded 10 cm NGMSR (Streptomyosin-Resistant Nematode Growth Media) plates with bacteria by adding 1-2 mL of saturated HB101 to each plate and leaving the plates did not get delivered during the sequence were collected afterwards in order to determine the total number of worms initially loaded in each well.

Previously measured fluid flow rates and well channel distances were used to postulate adequate timings for the full population delivery from each well. Based on these calculations and preliminary experiments, a timing of 2.8 seconds for step 1 with the maximum pressure (138 kPa) was applied through the gasket to empty the slowest wells in the device. This timing was applied to all of the wells to ensure maximal delivery success across the chip. Various gauge pressures were applied to the gasket and the fluid reservoir connected to fluid inlet 122 (FIG. 1A; 5-20 psi, 34.5-138 kPa). A 20 psi (138 kPa) gauge pressure was applied to the fluid reservoir connected to fluid inlet 126 (FIG. 1A) throughout the experiments. Population size repeatability was characterized across different delivery pressures. The timings of each automated step in the sequence for each microwell and pressure tested are included in Table 2 below. The actuation scheme specific to Well 1 is also included in Table 2.

TABLE 2

Timings for automated delivery sequence applied to each well and device truth table for delivery from Well 1.

| Step | Timing (s) | 154 | 124 | 115 | 110 | 130 | 128 | 132 | 122 | 126 |
|---|---|---|---|---|---|---|---|---|---|---|
| 1 | 2.8 | 1 | 0 | 0 | 0 | 0 | 1 | 0 | 1 | 0 |
| 2 | 0.5 | 0 | 0 | 1 | 1 | 0 | 1 | 0 | 1 | 0 |
| 3 | 0.7 | 0 | 1 | 1 | 1 | 1 | 0 | 0 | 0 | 1 |
| 4 | 0.7 | 0 | 1 | 0 | 0 | 0 | 0 | 1 | 0 | 1 |

"1" indicates the valve/fluid reservoir is pressurized, while "0" means that it is not pressurized.

with their lids closed at room temperature for 2-3 days for drying. NGMSR pads were prepared with Nistatin (anti-fungal, Fisher Scientific, 0.01 mg/mL) and Streptomosin sulfate (anti-bacterial, Sigma Aldrich, 0.2 mg/mL).

We used the following strains in our experiments: SK4005: zdIs5 [(Pmec-4::gfp)+lin-15(+)] I, CZ1200: juIs76 [(Punc-25::gfp)+lin-15(+)] II; lin-15b(n765) X, TU3311: uIs60 [Punc-119::yfp+Punc-119::sid-1], and TU3595: uIs72 [pCFJ90 (Pmyo-2::mCherry)+Punc-119::sid-1+Pmec-18::mec-18:: gfp]; sid-1(pk3321); him-5(e1490) V; lin-15b (n744) X.

Preparation of Synchronous Worms

We transferred a large population of gravid adult worms grown on seeded NGMSR plates to a small volume (0.3 mL) of a 1:2 mixture of 5 M sodium hydroxide to sodium hypochlorite (bleach). After 2-3 minutes, the adult bodies are mostly dissolved, leaving unhatched embryos intact. We spun down this suspension with a centrifuge, removed the supernatant, and then added 1 mL, of distilled $H_2O$ to wash out the bleaching solution. We repeated the washing step two more times, and pipetted the embryos onto an unseeded NGMSR plate. After 12 hours, most of the embryos reached to the L1 life stage. These worms were then transferred to seeded NGMSR plates, where they reached the L4 life stage after an additional 24-28 hours.

Timed Loading Experiments with Worms

The microfluidic device's worm delivery efficiency was evaluated by placing worm suspensions (~100-200 worms/well, strain: SK4005) that had reached the L4 life stage into the device's microwells, and running the automation sequence of valve actuations to induce flow through each well at designated pressures and timings (See FIGS. 2A-2E). The worms exiting the main channel were collected in a 96-well plate, and counted using stereoscope. Worms that After the sequence was applied to a single microwell, step 3 (FIG. 2D) was repeated once more to flush out additional fluid from main channel. If no worms were found in this fluid, it served as confirmation that all animals released in the main channel from the microwell were delivered during the four steps of the automated sequence.

Testing Worm Population Segregation

The ability of the automated sequence and microfluidic device architecture to keep worm populations segregated while delivering the populations was evaluated by loading four different worm strain populations (SK4005, CZ1200, TU3595, and TU3311) into microwells of the device. Each *C. elegans* strain had a different set of neurons labeled with endogenous fluorescent markers, facilitating visual differentiation of the strains. Each of the four strains was placed into a set of 4 microwells. The automated delivery sequence was then run at the maximum operational gauge pressure (20 psi, ~138 kPa) to deliver the worm populations from each microwell. The populations were collected in microwells of a 96-well plate. Each worm collected was evaluated using a fluorescent stereoscope to examine the morphology of their fluorescently-labeled neurons and confirm their strain type. The number of worms belonging to each strain within each population sample collected was counted.

Worm Viability

The effect of delivery on worm viability was also investigated. Four populations of *C. elegans* worms were loaded into four representative wells on the device, and delivered using the automated delivery sequence. 20 randomly chosen living worms from each sample collected were placed onto separate NGMSR growth pads, and compared to a control sample of worms from the original worm suspension that was used to load the microwells. The worms were kept at 16.5° C. throughout the viability scoring process. The animals were scored every 24 hours. Worms were considered dead if they did not move, did not respond to touch with platinum wire, or crawled off the agar pad. Whenever necessary, worms were transferred to new seeded plates to separate them from their progeny and contaminants. The log-rank test was used to determine statistical differences between test populations and control. P-values<0.05 were considered statistically significant.

Results and Discussion

Design Considerations

Design of the multiplexer microfluidic device for worm population delivery required addressing four major design considerations: 1) interfacing with 96-well plate format microwells in a simple and efficient manner, 2) delivering multiple worm populations without cross-contamination, 3) achieving fast and repeatable worm population size delivery during device operation, and 4) hands-free automation within these constraints.

The design efforts culminated in a computer-controlled multiplexer microfluidic device with built-in conical microwells for simple population loading. The microfluidic device also featured an optimized microchannel/microvalve architecture, which facilitated the rapid (less than 5 sec per well) and automated delivery of C. elegans populations from sixteen different microwells without cross-contaminating populations.

Conical microwells having dimensions consistent with the microwells in traditional microwell plates were integrated directly into the microfluidic device for fast and simple loading of multiple worm strains into the microchannels (FIG. 1C). The microchannel architecture and sequence of automated valve actuations were configured to prevent cross contamination between worm strains in different microwells during device operation. As shown in FIGS. 1A and 1B, the inlet channels (106) emerging from the individual microwells (1-16) interface at the main channel (102) in a staggered arrangement relative to inlet channels on the intersecting opposite side of the main channel. During the automated sequence, the computer program delivers worms from the microwell connected via an inlet channel that intersects the main channel closer to the downstream end of the main channel exit before delivering from other microwells upstream. The staggered channel arrangement, delivery sequence, and the placement of valves in proximity to the intersection of each inlet channel with the main channel ensures that worms from a given inlet channel will not enter the inlet channel of a microwell that has not yet had its worms delivered.

Several pressure and timing combinations were investigated to understand how many worms could be repeatedly delivered from using the device. A computer program was used to handle all of the valve actuation and pressure-to-fluid application during the experiments.

Built-in Conical Microwells for Sample Loading

The first design consideration was addressed by integrating an array of microwells within the microfluidic device. Specifically, a molding method was used to produce identical conical microwells that could be filled with standard micropipettes. The microwells were fluidly connected to the inlet channels in the multiplexer microfluidic device. With a height of ~1.4 cm, the wells were ~5 mm in diameter at their openings and tapered down to 1.1 mm in diameter at the well channel entrance (FIG. 1C).

Initially, attempts were made to interface the multiplexer microfluidic chip to a standard multiwell plate; however, the operation of the interfaced system was prone to challenges. Specifically, a reusable hard polymer (PMMA & fluoropolymer) gasket containing an array of integrated microwells was fabricated and evaluated. The hard polymer gasket was designed to be plugged into the PDMS multiplexer microfluidic device. The microwells in the gasket were interfaced with the inlet channels in the microfluidic device via metal tubing sticking out of gasket's bottom side.

While loading worm samples into this gasket with a pipette was simple, sample leakage between the metal tubing and the PDMS was a significant problem. In addition, aligning all sixteen metal tubes on the bottom side of the gasket with the sixteen inlet channels in the multiplexer microfluidic device was technically challenging. Additionally populations of animals could potentially accumulate in the gasket wells or in the metal coupler, and cause contamination. By integrating the microwells directly into the multiplexer microfluidic chip (as opposed to providing sample reservoirs as a separate structural component that can be fluidly connected to the inlet channels of the multiplexer microfluidic device), sample leakage was eliminated and initial sample loading was simplified.

In the finalized device, most worms loaded in fluid suspension would sink and concentrate at the bottom of the conical wells in a couple of minutes; staging them at well channel entrances before delivery. Having the entire worm population placed at the channel entrance shortened the distance animals traveled on-chip and the timing necessary to deliver a similar number of worms. Wells built into the chip simplified initial population staging and prevented sample leakage.

Automated Worm Delivery

FIGS. 2A-2E illustrate the automated valve actuation sequence used to deliver worm populations from the microwells using the multiplexer microfluidic device illustrated in FIG. 1. For purposes of illustration, FIGS. 2A-2E illustrate the valve actuations used to deliver worms from a first microwell (1, FIG. 2A). These steps can then be repeated to deliver sample populations from a second microwell (5, FIG. 2B) in the device, as discussed in more detail below.

FIG. 2A schematically illustrates the elements of the multiplexer microfluidic device prior to delivery of worms from a first microwell (1). In this case, all valves in the multiplexer microfluidic device are in the closed position. Prior to delivery, the worms are pre-staged upstream of a valve (110 in the case of the first microwell 1, and 112 in the case of the second microwell 5) positioned along each fluid inlet channel (106). The closed valves prevent passage of the worms past the valves.

In step 1 (FIG. 2B), fluid flow is directed from the first microwell (1) to the exit of the main channel (e.g., a sample processing element from the fluid outlet, 134) by pressurizing the gasket and the appropriate valves (i.e., opening valves 110, 115, 130, and 132). Simultaneously, fluid flow was initiated from fluid inlet 122 by opening valve 124 and applying pressure to a fluid reservoir fluidly connected to fluid inlet 122. This causes worms to flow from microwell 1 to the exit of the main channel (e.g., a sample processing element from the fluid outlet, 134).

In step 2 (FIG. 2C), microwell 1 is no longer pressurized via the gasket, and valves 110 and 115 are closed. Fluid flow was continued from fluid inlet 122 to wash any excess animals from the main channel.

In step 3 (FIG. 2D), valves 124 and 130 were closed, and fluid flow was initiated from fluid inlet 126 by opening valve 128 and applying pressure to a fluid reservoir fluidly connected to fluid inlet 126. The fluid flow from fluid inlet 126 was to wash any excess animals from the main channel and tubing connecting the device to its ultimate destination (e.g., a sample processing element). Since fluid inlet 126 has an essentially limitless fluid reservoir and faster flow rate per unit pressure than any of the well channels, it can quickly finish the worm population delivery without exhausting a given well's small fluid supply. Using a minimum amount of a well's fluid during delivery reduces the risk of bubble introduction into the microchannels.

In step 4 (FIG. 2E), valve 132 was closed, and valves 115 and 110 were opened. Fluid flow was continued from fluid inlet 126 to wash any remaining animals from the main channel and inlet channel back to the first microwell 1.

This automated valve actuation sequence could then be repeated to deliver sample populations from additional microwells in the multiplexer microfluidic device.

Population Segregation

Channel Architecture Solutions

The multiplexer microfluidic device was configured to prevent cross-contamination of distinct sample populations (e.g., different worm populations) delivered from different sample reservoirs of the device (e.g., microwells). First, a valve was positioned in proximity to the intersection of each inlet channel with the main channel. The valve was configured to control flow between the inlet channel and the main channel. This design element prevented sample populations from one microwell from proceeding up an inlet channel connected to another microwell in the device. Second, a fluid inlet channel was fluidly connected to the main channel upstream from the inlet channels. This fluid inlet could be used, as described above, to wash out remaining members of a sample population between the delivery of each sample population from each sample reservoir. Third, the inlet channels were configured such that the intersections of the inlet channels and the main channel were staggered, meaning that where an inlet channel forms an intersection with the main channel, a second inlet channel does not intersect the main channel at the same point (i.e., the entrances of two inlet channels do not sit directly across from one another along the main channel). Finally, the intersections of the inlet channels and the main channel were designed to be non-perpendicular. By eliminating a sharp-angled intersection, the unpredictable flow of samples (e.g., worms) around sharp corners was eliminated.

These design features prevented worms from cross-contaminating other microwells during automated device operation. Video observation of automated device operation using worm sample populations revealed no worms accidently flowing into an inlet channel connected to another microwell.

Automation Sequence and Population Segregation

To achieve the sequential delivery of distinct sample populations from multiple wells in a multiplexer microfluidic device, the order in which the microwells were unloaded was selected in order to reduce the time needed to unload the worm populations, and to minimize the cross-contamination of sample populations.

With reference to FIG. 1A, the microwells were unloaded in a sequence such that microwells connected to the main channel by inlet channels sharing an upstream valve (e.g., sharing valve 110, 111, 112, or 113) in common, were all delivered using the sequence described above before moving on to the next series of wells. For example, fluid flow from microwells 1-4 is regulated by valve 110; therefore microwells 1-4 are all delivered prior to delivering sample populations from microwells 5-16. By unloading microwells in this fashion, the number of washing sequences required (e.g., step 4 described in FIG. 2E) are minimized. For example, sample populations can be delivered from 1-4 using steps 1-3 (FIGS. 2B-2D), for the first three microwells that share valve 110, while skipping step 4 until the fourth microwell is unloaded. Then, the automated program can perform step 4 on all four microwells simultaneously to wash back any excess worms in the inlet channels to their respective sample reservoirs.

Again with reference to FIG. 1A, the order of microwells unloaded within a column group (i.e., the order with which microwells sharing a given valve 110, 111, 112, or 113) and the order in which the column groups were unloaded was selected such that the microwells whose inlet channels intersect with the main channel furthest downstream have their sample populations delivered earliest in the sequence (e.g., microwells 1-4 were delivered before microwells 13-16). In this way, a specific population of worms traveling from an inlet channel into the main channel only flows past inlet channels fluidly connected to microwells from which sample populations have already been delivered.

Figure 3A:
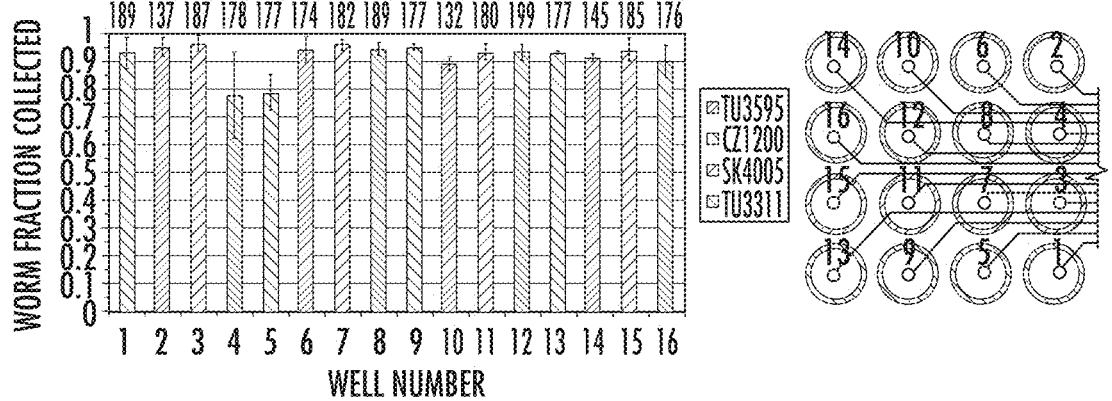
FIG. 3A is a bar graph plotting the fraction of worms collected from a given microwell that are of the same strain loaded into the well from which they are collected following the automated delivery of different strains of worms from each well of the multiplexer microfluidic device shown in FIG. 1A. The fraction of worms of the loaded strain delivered from each well of the multiplexer microfluidic device is included above each bar in the graph. In the case of FIG. 3A, identical strains of worms were loaded into each microwell in a given row of the 4:4 matrix of microwells of the multiplexer microfluidic device. There was no mixing between delivered populations.

To validate the ability of the multiplexer microfluidic device in FIG. 1A as well the automated delivery sequences described above to deliver sample populations rapidly without cross-contamination of populations from different microwells, four different strains of *C. elegans* worms were loaded into the microwells of the microfluidic device. The four strains were loaded in the device such that each microwell within each column of the 4:4 matrix of microwells in the device illustrated in FIG. 1A was loaded with a different *C. elegans* strain: populations of TU3311 worms were loaded in microwells 1, 5, 9, and 13; populations of SK4005 worms were loaded in microwells 3, 7, 11, and 15; populations of CZ1200 worms were loaded in microwells 4, 8, 12, and 16; and populations of TU3595 worms were loaded in microwells 2, 6, 10, and 14. All sample populations were then delivered using the sequences described above. Populations of worms delivered from each microwell were collected, and then analyzed to determine the fraction of the worms collected from the microwell that were of the strain placed in the microwell for delivery. The results are plotted in FIG. 3A. These results conclusively eliminated the possibility of mixing of the sample populations between microwells within the same given column of the microwell array; however, mixing between populations in microwells of the same given row was not yet ruled out.

Figure 3B:
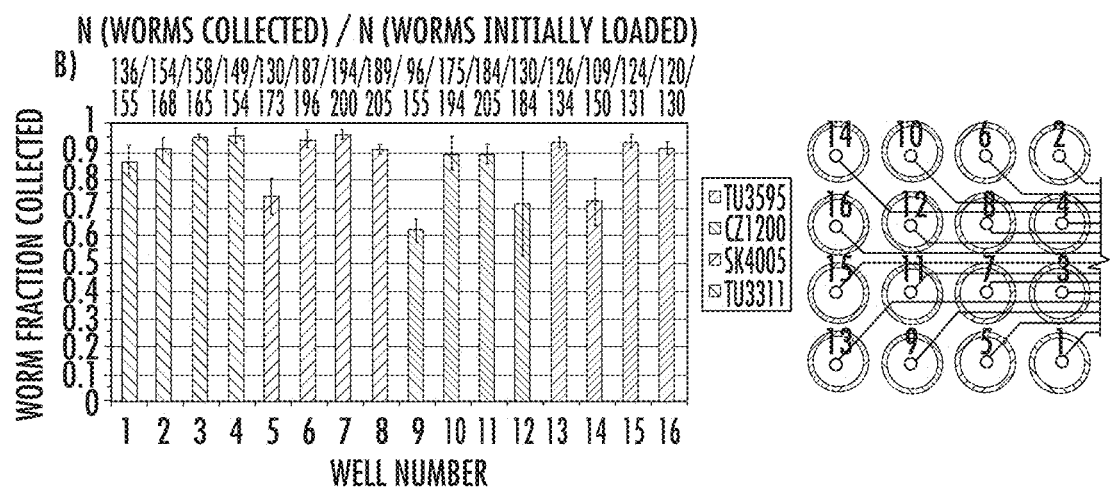
FIG. 3B is a bar graph plotting the fraction of worms collected from a given microwell that are of the same strain loaded into the well from which they are collected following the automated delivery of different strains of worms from each well of the multiplexer microfluidic device shown in FIG. 1A. The average fraction of worms of the loaded strain delivered from each well of the multiplexer microfluidic device is included above each bar in the graph. In the case of FIG. 3B, identical strains of worms were loaded into each microwell in a given column of the 4:4 matrix of microwells of the multiplexer microfluidic device. There was no mixing between delivered populations.
Figure 3B:
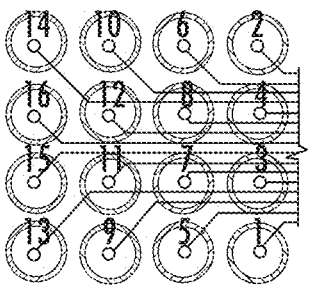

To ensure that mixing between microwells within the microwells making up a given row of the 4:4 matrix of microwells in the device illustrated in FIG. 1A was not significant, the experiment was repeated with each column being loaded with a different *C. elegans* strain: populations of TU3311 worms were loaded in microwells 1, 2, 3, and 4; populations of SK4005 worms were loaded in microwells 5, 6, 7, and 8; populations of CZ1200 worms were loaded in microwells 9, 10, 11, and 12; and populations of TU3595 worms were loaded in microwells 13, 14, 15, and 16. All sample populations were then delivered using the sequences described above. Populations of worms delivered from each microwell were collected, and then analyzed to determine the fraction of the worms collected from the microwell that were of the strain placed in the microwell for delivery. The results are plotted in FIG. 3B. Once again, the experiment demonstrated no cross-contamination from sample population to sample population.

These experiments demonstrated the multiplexer microfluidic device's ability to deliver 16 different sample populations to a desired location in a rapid and automated fashion without significant cross-contamination of the sample populations.

Flow Rates

Flow rates across the microfluidic to the main channel outlet were measured with several applied pressures from the gasket system. These experiments elucidated adequate timings for population delivery from each microwell, and established operational benchmarks for proper device function. For each microwell tested, applied pressures ranging from 2.5-20 psi, at 2.5 psi increments (~17-138 kPa in ~17 kPa increments) were examined, and compared to theoretical calculations based on the flow resistance imposed by the microchannel geometries.

In the multiplexer microfluidic device, inlet channel lengths varied according to their proximity to the main channel exit. Microwells 1-4, 5-8, 9-12, and 13-16 were designated as the four main microwell reservoir groups based on their distance from the main exit channel. All microwells in a given group were roughly the same distance from the main channel exit. Thus, data collected from one well in each group provided an adequate picture of flow rate behavior across the different microwells.

Measured flow rates generally varied linearly with applied pressure (linear regression $R^2=\sim 0.99$ for all measured data) and overlapped with the theoretically expected values within 10% (FIG. 2). Since fluidic resistance is directly proportional to channel length, the longer channels had lower flow rates given the same pressure at the gasket. The results implied that one would have to linearly adjust the pressures or timings applied to the microwells via the gasket system to deliver the same number of worms across microwells with different inlet channel lengths. Such differences were easily accounted for in the automation software, which allowed for millisecond resolution adjustments to the timings of every automation step for each microwell.

Sources of slight deviations from theoretical flow rates were most probably a result of the elastic properties of PDMS. At the higher pressures, it is possible for the PDMS channel cross-sections to expand and effectively decrease the channel's fluidic resistance. This may be the cause for the slightly higher-than-predicted flow rates observed above 80 kPa in microwells 2 and 8. Conversely, throughout the lifetime of the device, a general drift towards lower flow rates was observed. It is possible that this is the result of the increasing rigidity of PDMS due to increased cross-linking. This drift can be eliminated by either baking the devices at high temperatures to enhance curing and cross-linking, or by simply waiting 2-3 weeks until device rigidity and flow rates have stabilized.

Animal Viability after Delivery Through the Device

When compared to a control group, animal viability was not seriously affected by delivery of the worms through device. The lifespan of 20 worms was tracked for each condition tested. In all cases, every single worm survived at least 6 days. Table 3 further summarizes the total average lifespan of worms delivered through the different wells with 5 psi, 10 psi, and 20 psi applied to the gasket during the automated delivery sequence.

TABLE 3

Average animal lifespan (days) for delivery through on-chip wells with different pressures

| Well # | Pressure | | |
|---|---|---|---|
| | 5 psi (35 kPa) | 10 psi (69 kPa) | 20 psi (138 kPa) |
| Well 2 | 19.1 ± 3.7 days | 17.8 ± 4.6 | 17.9 ± 6.3 |
| Well 6 | 16.8 ± 4.1 | 17.2 ± 5.1 | 18.7 ± 3.8 |
| Well 10 | 17.4 ± 4.3 | 17.3 ± 4.7 | 17.2 ± 6.1 |
| Well 14 | 17.1 ± 5.1 | 19.2 ± 3.2 | 15.2 ± 3.9 |

* n = 20 worms for all conditions, including control

Comparing to the average lifespan of worms in our control group (17.8±6.6 days) no statistically significant decrease in average lifespan was observed in worm populations delivered via the multiplexer microfluidic device.

Fast Worm Population Delivery

The conical cross section of the microwells enabled a majority of the sample population of worms loaded into a given microwell to settle at the base of the sample reservoir (i.e., in proximity to the inlet channel entrance, FIG. 1C, right side).

Using this microwell design changes and optimized timings in the automated delivery sequence, quick and nearly complete delivery of the worm sample populations loaded into the microwell sample reservoirs was achieved. After initial testing, it was determined that, despite different flow rates across the different microwells in the device, a timing of 2.8 seconds for Step 1 of the automated sequence would be adequate to deliver most worms loaded into any of the microwells.

Figure 4:
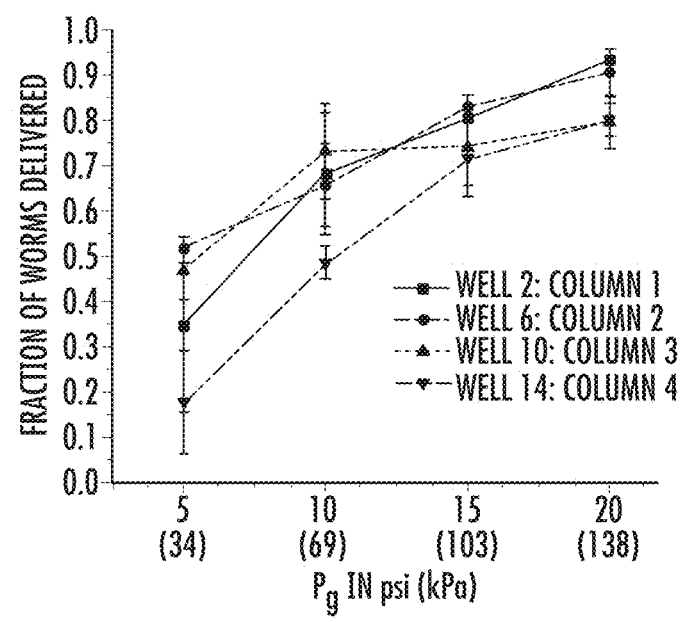
FIG. 4 is a plot of the fraction of worms loaded in microwells 2, 6, 10, and 14 from each columns 1-4 of the multiplexer microfluidic device that are delivered to the outlet of the device as a function of different pressures applied to the microwells (in psi and kPa).

FIG. 4 is a graph plotting the fraction of the initially loaded worm sample population delivered during the automated sequence across the operational gauge pressures applied to the gasket. As a majority of the worms settled to the bottom of the microwells, it was not necessary to empty the entire microwell contents to deliver a majority of the worms from a given microwell. Because the fluid level in a given microwell never went below the initial loading volume, bubbles never entered the inlet channels. At the maximum pressure applied to the gasket (20 psi, 138 kPa), the multiplexer microfluidic device only required 4.7 seconds per microwell to deliver 80-93% of the worm population initially loaded into the microwells. This speed was achieved in a fully automated process. The delivery speed achieved by this platform is nearly an order of magnitude faster than any other platform capable of delivering worm populations from microwells without bubbles.

Conclusions

The multiplexer microfluidic device could deliver up to 16 different worm populations in sequence to a desired location from its 4×4 array of well-plate format sample reservoirs without any significant mixing between populations. The device utilized an automated loading sequence to produce repeatable flow rates and worm population delivery sizes. The flow and worm delivery rates varied from microwell to microwell depending on the specific resistance of individual inlet channels. The platform was able to deliver on average more than 90% of the contents of each well (~100-200 worms) in 4.7 seconds without contaminating the samples with bubbles; capabilities not seen in other more complex worm population delivery platforms based on suction.

Example 2: Microfluidic Laser Axotomy Platform—a Microfluidic Sample Processing Element An automated microfluidic platform for performing fast laser axotomies on single worms was designed, fabricated, and tested. The microfluidic design uses a T-shaped structure and two-way flow to load and eject worms in orthogonal directions. The device also includes a deformable membrane, which upon application of pressure, traps worms against the optical interface during surgery. The device includes a peristaltic-like gate at the entrance of the trapping chamber to ensure loading of a single worm at a time in the trapping chamber. These microfluidic features minimize worm manipulation errors, such as trapping multiple worms or sending a non-axotomized worm into the pool of axotomized worms. They also increase axotomy throughput.

The transportation, positioning, and immobilization of worms were fully automated. By controlling the synchronized actuation of microfluidic and external solenoid valves, the automated software could redirect flow within the device, and allow worms to be processed serially. For identification and targeting of the axon of interest for laser ablation, an image processing algorithm was used.

Materials and Methods
Device Fabrication

Standard soft-lithography techniques were used, with some modifications to fabricate the two-layer microfluidic device described here. The bottom layer that transports the C. elegans, is hereafter termed as the "flow layer." The top layer that when pressurized both immobilizes the worms and actuates the valve-like structures on the chip will be referred to as the "control layer."

Briefly, SU-8 resists (MicroChem) were used to create molds for the polydimethylsiloxane (PDMS; Sylgard 184, Dow Corning Corp.) microfluidic structures. To begin, SU-8 3005 was spin-coated onto a 4" silicon wafer to a thickness of 9 μm and the sieve structures (i.e., array of short flow outlets located in the trapping chamber and staging chamber) were patterned with a photomask using the recommended processing protocols given by the manufacturer. SU-8 2025 was then applied atop the sieve structure at a thickness of 35 μm and the remainder of the flow layer mold was created by alignment and exposure through a second photomask using a mask aligner (MA6/BA6, Suss MicroTec). The mold for control layer was fabricated out of combined patterns of a positive photoresist (AZ 50XT) and negative photoresist (SU-8 2025). A reflow process was used after positive resist development to create semi-circular curved channel cross-sections in the positive resist by ramping up the mold to AZ50-XT's glass transition temperature (123° C.) and keeping it there for approximately 3.5 minutes. The wafers with the developed SU-8 molds were modified with a fluorinated silane (SIT8173.0, Gelest Inc.) that served as a release agent. All film thicknesses were verified with a stylus profilometer (Dektak 6M, Veeco).

PDMS (at 10:1 resin:crosslinker) was thoroughly mixed, degassed in a vacuum oven at room temperature, poured onto the control layer mold to a thickness of ~5 mm, degassed again, then cured at 75° C. in an oven for 30 minutes. To create the flow layer, PDMS was spin coated onto the flow layer mold at 1700 rpm for 33 s and allowed to rest at room temperature for 5 min, resulting in a uniform ~50 μm-thick PDMS layer with an approximately 20 μm-thick PDMS film covering the top of the SU-8 features. The PDMS on the flow layer mold was then partially cured on a hotplate at 75° C. for approximately 13 min. The thick control layer was aligned and bonded on top of the partially cured flow layer mold with the aid of a stereoscope. To improve the bonding strength between the two PDMS layers, the wafer was placed in an oven at 65° C. overnight.

The two-layer PDMS device was then peeled from the flow layer mold, and then 23 gauge holes were punched through the PDMS for making external fluidic connections. The device was then bonded to a 25×50 mm no. 1.5 cover slip using the same $O_2$ plasma conditions described above and finally placed in an oven at 65° C. for 4 h to enhance the PDMS-glass bonding. Sterile polyethylene tubing (Intramedic) was connected to the device using 22 gauge steel couplers (Instech Solomon) inserted into the punched PDMS holes, and if necessary, the connection was sealed with a small amount of acrylic glue prior to pressurization.

Optomechanical Setup

The laser axotomy setup incorporates optics to deliver femtosecond laser pulses for surgery into a home-built epi-fluorescence microscope. Briefly, axotomies were carried out using a train of 200 femtosecond laser pulses of 10 nJ. A regenerative Ti-Sapphire amplifier (Spitfire, Spectra Physics) seeded by a mode-locked tunable Ti-Sapphire (Tsunami, Spectra Physics) provided 220 fs (FWHM) laser pulses at a center wavelength of 780 nm and a repetition rate of 1 kHz. The beam energy was measured with an energy meter (PJ10, Ophir) prior to performing all axotomies and adjusted with two sets of half wave plates/cube beamsplitters pairs. To calibrate the three-dimensional location of the laser's focal volume, we used a small ablation spot on the surface of a microscope slide as a reference. A high numerical aperture objective lens (Plan-Apochromat, 63×, 1.4 NA, oil-immersion, Zeiss) tightly focused the laser beam to a $1/e^2$ spot size of 620 nm.

Automated microscopy was performed on the same setup with a 5× air objective (Plan-Apochromat, NA=0.16, Zeiss) and the 63× oil-immersion objective (Plan-Apochromat, NA=1.4, Zeiss). For fluorescence imaging of green fluorescence protein (GFP) labeled axons, a mercury arc lamp (XCite 120, EXFO) provided the excitation light source going through a FITC filter set (Semrock). A three-axis translation stage made of individual actuators (LTA-HS, Newport) and operated by a single controller (ESP301-3, Newport) positioned the samples. These stages could translate at up to 5 mm/s with a minimal incremental motion of 100 nm and a lateral resolution 35 nm (achieved after backlash compensation). High precision positioning was performed by a three-axis piezoelectric actuator (MAX302, Thorlabs) with a theoretical resolution of 20 nm and a travel range of ±10 μm for each axis. A CCD camera (1392×1040 pixels with 6.45 μm pixel size, CoolSnap ES, Photometrics) captured the images with fields of view (FOV) of 1.8×1.34 $mm^2$ at 5× magnification (1.29 μm/pixel, 1.88 μm resolution at 500 nm) and 143×107 $μm^2$ at 63× magnification with 1.4 NA (102 nm/pixel, 214 nm resolution at 500 nm).

For controlling the device flow layer, pressurized external fluid chambers controlled by three-way solenoid valves (Lee Company, LHDA0521111H) were coupled to the chip via a manifold (Lee Company, LFMX0510418). These chambers contained M9 buffer solution (22 mM $KH_2PO_4$, 22 mM $Na_2HPO_4$, 85 mM NaCl, 1 mM $MgSO_4$, in $dH_2O$). To minimize debris, all M9 buffer was passed through 1.2 μm in-line filters (Acrodisc, Pall Corp.) prior to entering the microfluidic device. Valves were independently actuated with a multichannel amplifier (Automate Scientific) that was controlled with a DAQ card (USB6501, National Instruments). All automated stage positioning, valve actuation, and image processing was performed with a custom-written LabVIEW (National Instruments) program.

C. elegans Culture

C. elegans were maintained on nematode growth medium streptomycin-resistant (NGMSR) agar plates seeded with HB101 E. coli bacterial culture using standard procedures at 16.5° C. The regenerating capabilities of the touch receptor neurons (namely, ALM and PLM) were routinely studied using the strain SK4005 [zdIs5[Pmec-4::GFP; lin-15(+)] I], which expresses GFP in the six touch receptor neurons.

Populations of age-synchronized worms were prepared by collecting and isolating embryos following hypochlorite treatment. Gravid adults were lysed with a small volume of a 2:1 mixture of sodium hypochlorite and 4 M sodium hydroxide, and the collected eggs were suspended in M9 buffer overnight on a rocker to aerate. The embryos hatch overnight, arrested in L1 stage until food is reintroduced. The L1 larvae were then placed on NGMSR agar plates seeded with HB101 *E. coli* and allowed to grow for 48 hours at 16.5° C. at which point the L1 larvae have grown into young L4 animals that can be isolated for use.

Cleaning Procedure of the Nematodes

L4 stage worms were picked up from the agar plates and placed in centrifuge tubes filled with 1.5 ml of M9 buffer. Then, these tubes were placed in an ice water bath for approximately 5 minutes. The cold temperature temporarily paralyzes the worms and they settle down at the bottom of tube. The supernatant of M9 buffer and small debris is then removed, while leaving the worms at the bottom of the tube. This procedure is repeated 3 times before loading the worms in the chip. Cleaning procedure sustains the continuity of the automation process because debris can clog the sieve structures and thin channels.

Laser Axotomies on Agar Pads

Agar pads were prepared by sandwiching 0.9 mL of melted 4% agar between two microscope slides that were then pulled apart upon cooling to create a flat, uniform surface. For anesthetization, worms were transferred with a platinum wire into a small droplet of 5 mM levamisole (Sigma) in M9 buffer that was placed in the center of the solidified agar pad. Just prior to laser axotomy and follow-up fluorescence imaging of recovery, a coverslip was placed on top of the worms. Manual axotomies were performed on the same upright setup used for automated surgery, described above. Subsequent imaging of recovering worms was performed on an Olympus microscope (BX-51) with a 60×, NA=1.35, oil immersion objective. The statistical significance of recovery data was calculated using the Fisher Exact Test.

Results and Discussion

Microfluidic Device Design

A key design consideration when developing an automated approach to perform laser axotomies on *C. elegans* is optimizing the delivery of a single worm from a large, on-chip population into the trapping chamber, while minimizing the degree of spatial variability in the trapped position of the worm. The ability of trapping worms at the same location with high degree of repeatability affects the maximum speed at which the worm can be targeted by the image processing software. In addition, to reduce ambiguity in axon re-growth data, other delivery errors, such as trapping multiple worms or sending a non-axotomized worm into the pool of axotomized worms must be considered.

With these concerns in mind, a T-shaped axotomy device was designed that enabled automated delivery and trapping of worms (see FIG. 5A). The T-shape design of the trapping chamber (504) possesses two major advantages that facilitate the desired full-automation of the axotomy process: first, it permits a repeatable immobilization location of the worms, which significantly saves time and complexity for automatically locating the worm via image processing, and second, it allows for a decoupling of the injection and the flushing channels, thus permitting a precise and simple unloading of the worms after axotomy. The device includes a staging chamber (510) and loading chamber (502) configured to precisely deliver the animals one by one to the center of the trapping chamber (504). The worms are pushed against an array of narrow, short flow outlets that practically form a microfluidic sieve (505) fluidly connected to the trapping chamber (504). The pressure drop across the sieve immediately straightens the delivered worms into an elongated configuration just before actuating valve 522 to mechanically restrict the worm within the trapping chamber. Off-chip, two-way solenoid valves control fluid flow through a fluid inlet (506) fluidly connected to the trapping chamber and an exit area (509), as required, when loading each worm in the trapping chamber and unloading after axotomy.

In order to conserve optimal focusing of the laser beam and thus axotomy precision, flow channels with semicircular cross-sections were not used. As a consequence, standard pneumatically activated microfluidic valves cannot form a complete seal to completely block fluid flow. To fabricate pneumatic-type valves which completely block fluid flow would require that there be a thin layer of PDMS or a control layer between the worm and the coverglass in the trapping chamber. This extra PDMS layer in the optical path would introduce an index of refraction mismatch and spherical aberrations at focusing distances beyond 30-40 µm, substantially reducing the effective numerical aperture and seriously compromising the precision of both imaging and surgery. It has previously been shown that a deflected PDMS membrane can almost completely seal a 30 µm-deep and 120 µm-wide rectangular channel, leaving a 10 µm gap in the bottom corners of the channel. Therefore, the inlet of the staging chamber 510 was designed to be, at the least, 120 µm wide beneath the gate valves 520 and 521 to prohibit L4-stage *C. elegans* from passing through. All channels above valve structures on the device had their channels widened to effectively block worms during valve closure.

Several filter structures were incorporated into the device to prevent unwanted debris from clogging the sieve structures and affecting device performance. Despite the removal of particulate matter from the M9 buffer with a 1.2 µm filter before introducing it into the microfluidic device, an accumulation of a small amount of microscopic particles was still observed. This unwanted debris mainly originated from agar particulates and molted worm cuticles. To ensure an automated operation without interruptions or a decline in performance, an array of staggered filter structures (512) with gaps ranging from 50 µm down to 10 µm were incorporated at the entrance of each flow channel. These in-line microfluidic filters are highly effective at collecting the debris even after performing many axotomies. At the entrance of the loading chamber, the array consists of pillars 30 µm apart. This optimized distance between the pillars allows for the passage of worms, but blocks debris from entering the trapping area and clogging the sieve structures.

Progression of Valve Actuation and Flow

The control layer in the microfluidic device operates all the microfluidic valves to synchronize all the procedures (loading, trapping, axotomy, and unloading of the worms) in a fully automated manner. Specifically it serves to stage worms for serial processing, trap them individually for laser surgery, and control flows throughout the device as explained below. The majority of the flow in the device is driven by external solenoid valves connected with tubing to ports on the chip.

FIGS. 5B-5H show the sequence of valve and flow progression at each step during automation. The device was loaded with a population of worms (530) by blocking all flow channels except the small flow exits provided by sieve structures (501) fluidly connected to the loading chamber (FIG. 5B).

Once a population of worms was loaded into the loading chamber (502), a peristaltic-like gate is used to stage worms for serial injection into the trapping chamber (504) (FIGS. 5C-5E). The gate is operated by actuating two valves located on either side of the staging chamber (510): a first valve (520) positioned in proximity to the intersection of the loading chamber (502) and the staging chamber (510) that is configured to regulate fluid flow from the loading chamber to the staging chamber; and a second valve (521) positioned in proximity to the intersection of the staging chamber (510) and the trapping chamber (504) that is configured to regulate fluid flow from the staging chamber and the trapping chamber. Sieve structures (503) are fluidly connected to the staging chamber (8 µm tall and 10 µm wide, intersecting both sides of the staging chamber). The sieve structures act to direct the worm between the first valve (520) and the second valve (521) during staging. The staging process involves two steps. In the first staging step, valve 520 is opened, and pressure is applied to the loading chamber (FIG. 5C). Valve 521 remains closed. As a result, fluid flow is directed from the loading chamber (502) and through the sieve structures (503) fluidly connected to the staging chamber (510). This fluid flow directs a worm (530) from the loading chamber (502) into the staging chamber (510).

To prevent multiple worms from entering the staging chamber simultaneously, the dimensions of the staging chamber were selected in view of the approximate dimensions of the organism being delivered, such that only a single organism can be present within the staging chamber at a time. In this case, the staging chamber (510) was designed to have a height of 30 µm and a width of 35 µm. These values roughly correspond to the approximate diameter of the middle portion of an L4-stage worm. Moreover, the length of the staging chamber was 600 µm long, which is approximately the length of an L4-stage worm.

Once the worm travels into the staging chamber, the second staging step is performed. In the second staging step, valve 520 is closed, capturing a single worm (530) within the staging chamber (510) (FIG. 5D).

Once the worm is located in the staging chamber, the worm is then injected into the trapping chamber (504) by reversing the flow through the sieve structures (503) fluidly connected to the staging chamber (510), and opening valves 521 and 522 (FIG. 5E). The injection step lasts for approximately 1000 ms to allow the worm (530) to flow into the trapping chamber (504), and to straighten the worm against the sieve structure (505) fluidly connected to the trapping chamber. The reversed flow through the sieve structure fluidly connected to the staging chamber (503) prevents a second worm from flowing from the loading chamber (502) into the staging chamber (510) while the first worm is injected into the trapping chamber (504). In this way, only a single worm is delivered to the trapping chamber (504) at a time.

After the worm (530) is injected into the trapping chamber (504), valve 522, positioned over the trapping chamber (504), is closed in a pumping manner (repeatedly opened and closed before finally being closed) so as to avoid unfavorable folding of the worm against the sieve structure (505) fluidly connected to the trapping chamber (504) (FIG. 5F). When closed, valve 522 traps and flattens the worm (530) against the sieve structure (505) fluidly connected to the trapping chamber (504).

Once the worm (530) is positioned within the trapping chamber through the first steps of the image processing in the automation software, a translation stage moves to the center of the worm body, the white light (an LED array) is turned off, and the objective is switched from 5× to 63×, to prepare for automated surgery. Then the automation software proceeds to positioning the neuron of interest, focusing on and targeting the axon via image processing algorithms, which are explained below. The laser axotomy is then automatically performed (531) (FIG. 5G).

After finalizing the automated axotomy, the objective is switched back to 5×, the white light is turned on, and, the software simultaneously actuates several valves to unload the worm (530) from the trapping chamber (504) via the exit area (509) (FIG. 5H). This process involves opening the valve in the trapping chamber (522) and either the valve (523) controlling fluid flow through the first microfluidic channel in the exit area (507) or the valve (524) controlling fluid flow through the second microfluidic channel in the exit area (508). One of these microfluidic channels flows to a vessel to collect worms on which successful axotomies are performed, while the second microfluidic channel flows to vessel to collect worms on which the axotomy procedure is unsuccessful (which is subsequently discarded). Flow through the sieve structure (505) fluidly connected to the trapping chamber (504) is reversed to push the worm away from the sieve structure against which it is fluidly restricted. Fluid flow is then initiated through a fluid inlet (506) fluidly connected to the trapping chamber (504) to push the worm (530) from the trapping chamber (504) out through the exit area (509). In addition, fluid flow through the sieve structures (503) fluidly connected to the staging chamber (510) is reversed to flow back towards the loading chamber (502) so as to prevent clogging at the intersection of the loading chamber and the staging chamber in anticipation of the next cycle.

The cycle was then repeated by staging a second worm (FIG. 3C) and proceeding throughout the cycle. For the entire duration of the automated platform operation, a constant head pressure of ~15 kPa is used to continually drive flow through the loading chamber and move worms into the staging chamber.

The automated process was repeated until axotomies were performed on the desired number of worms. The rest of the worms loaded into the device can then be removed from the chip by opening all the valves and reversing the flow through the sieve structure (505) fluidly connected to the trapping chamber (504). The automated staging of a single worm took an average of 5.5 seconds, and the automated axon identification and targeted ablation required 12 to 18 seconds. The choice of the loading scheme with a staging step, substantially eliminates the possibility of trapping multiple worms. The entire process of staging, trapping, and axotomy including switching objective lenses takes about 25 seconds per axon on average.

Image Processing for Automated Identification and Targeting of Axons

Figure 6:
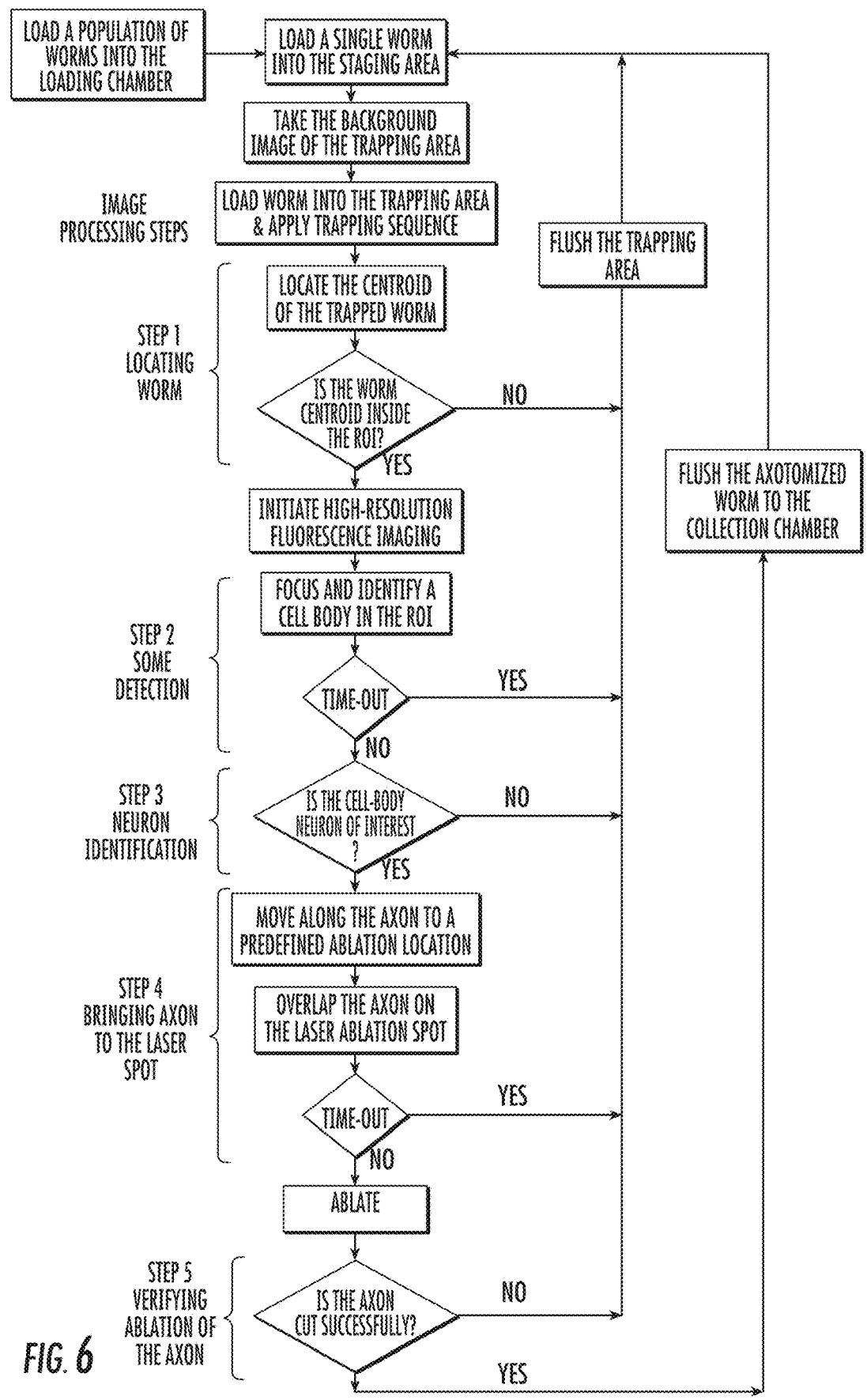
FIG. 6 is a flow chart illustrating the steps in the automated process, including the image processing algorithms used to perform laser axotomy, performed by the microfluidic sample processing element shown in FIG. 5A during processing of a worm.

As discussed above, the sample processing element was configured to perform laser axotomies on worms within the trapping chamber. A computer program was developed to perform the axotomies automatically on the mechanosensory ALM neuron using a five step procedure: (1) identify the location and center of the worm body in the trapping chamber; (2) focus coarsely and detect a cell body in the small FOV; (3) focus finely on the cell body to determine if the cell body is the neuron of interest and its orientation; and (4) focus finely on the targeted axon while moving it to the location of the laser focal point for precise axotomy. A flow chart describing the steps of the automation process, including the image processing steps, is included as FIG. 6. The automation code is designed to identify the GFP labeled, anterior longitudinal microtubule (ALM) neurons, shown in FIG. 9, panel A.

Step 1: Identification of the Worm Location and Center

Figure 7:
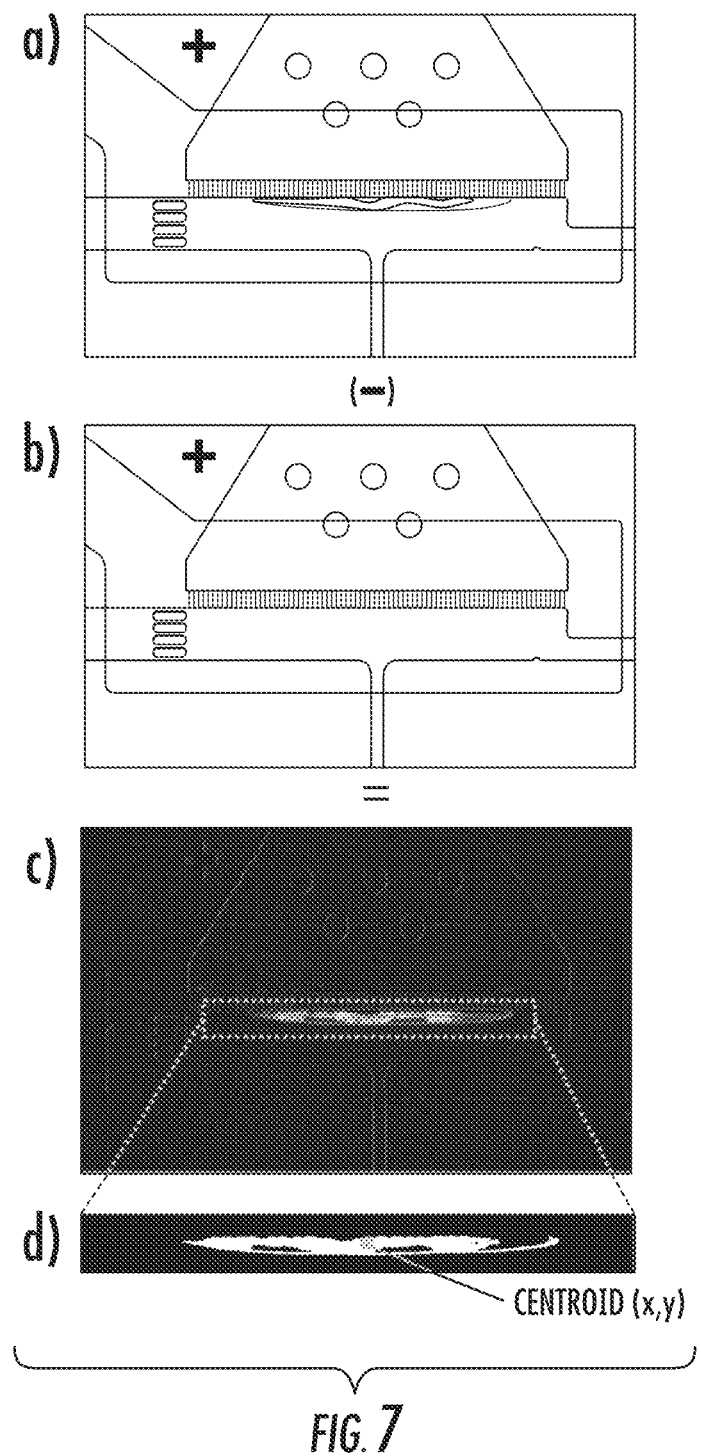
FIG. 7 illustrates the image processing methodology used to automatically perform laser axotomy on a *C. elegans* worm located in the trapping chamber of the microfluidic sample processing element shown in FIG. 5A. It specifically illustrates step 1 in the automation process as described in the flow chart presented in FIG. 6, to identify the location of the *C. elegans* worm within the trapping area and its centroid. Panel A shows a bright-field image of an immobilized worm. Panel B shows the image of the same immobilization area that was collected without a worm loaded while the deflecting membrane in the trapping area is actuated. Panel C shows the image of the worm body as obtained by subtracting the image in Panel B from the image in Panel A. Panel D shows the detected center of the worm's body after using an image thresholding and particle filtering that generates a high degree of contrast in a pre-determined ROI (defined as the borders of the trapping area).

Once a worm is immobilized within the trapping chamber (FIG. 5F), it is necessary to identify its centroid (position) and bring it to the center of the high magnification (63×) FOV for focusing. The known neuroanatomy in *C. elegans* enables verifying the location of the ALM cell body and also aids in accurately positioning the FOV for precise ablation of the ALM process. For that purpose, an image processing algorithm based on background subtraction and thresholding was used. By processing low magnification optical images, the algorithm calculated the location of the worm immobilized in the trapping chamber, as shown in FIG. 7.

Determining the centroid of the trapped worm serves as the first step towards identifying the exact location of the targeted axon. After a worm is loaded into the trapping chamber against the sieve structure (505) fluidly connected to the trapping chamber (504) and immobilized using valve 522, an image of the worm was captured and compared with a baseline image of the same 5×FOV with the valve membrane deflected, but without the worm loaded. By subtracting the baseline image from the snapshot of the trapped worm, the background is removed, leaving only the worm in the processed image. The subtraction operation removed nearly all non-worm objects. After getting the subtracted image, the automation program proceeded with extracting a Region-of-Interest (ROI), and then applying thresholding on the extracted image. In order to avoid any small non-worm objects in the thresholded image, a particle filter was used to filter out the areas with a total pixel size smaller than 300 pixels.

With this information, the 63×FOV could be sensibly moved to the expected location of the ALM neuron based on the known anatomy of the worm. The main advantages of using image subtraction in this automation step was that it eliminated the need for the implementation of complex and time-consuming pattern recognition algorithms, and its function is completely independent of the worm developmental stage.

Steps 2-4: Automated Identification and Targeting of Axons

Figure 8:
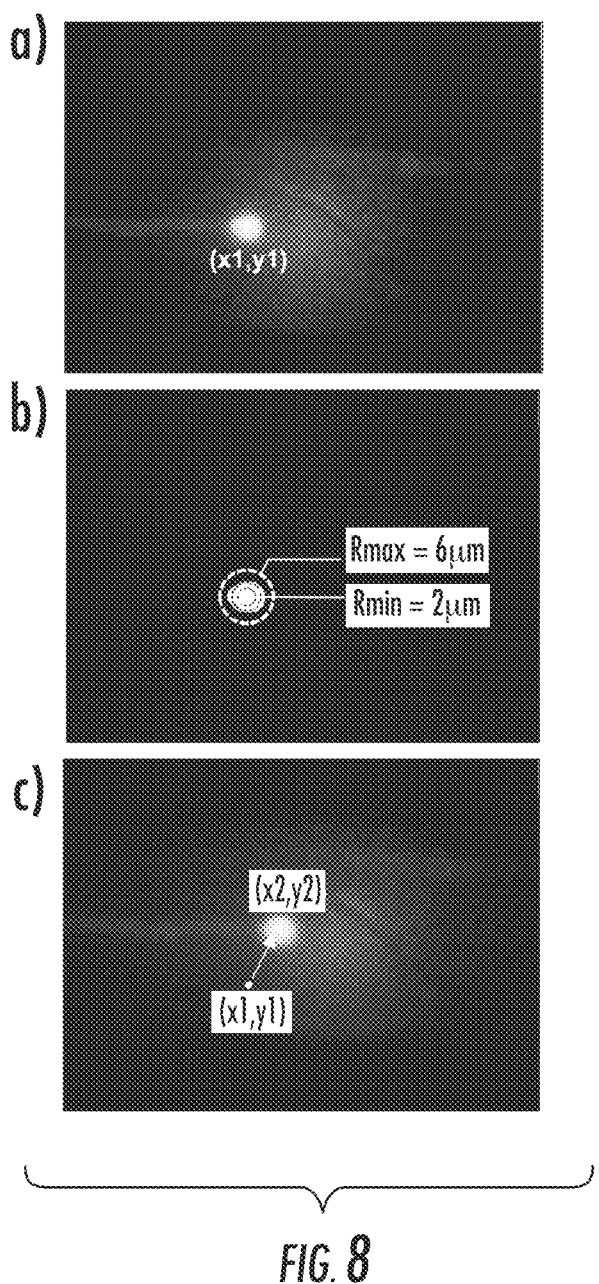
FIG. 8 illustrates the image processing methodology used to automatically perform laser axotomy on a *C. elegans* worm located in the trapping chamber of the microfluidic sample processing element shown in FIG. 5A. It specifically illustrates step 2 in the automation process as described in the flow chart presented in FIG. 6, to identify a cell body in the small FOV. Panel A shows a fluorescence image of the detected cell body in the small FOV. After the approximate location of the cell body (predicted as the ALM neuron) has been determined in white light by finding the worm's centroid using the 5× objective, the 63× lens is moved into place, in fluorescent illumination, and the focal plane is positioned at the worm-glass interface. The automation program moves the stage with the aid of translation-stage towards in-focus location of the cell body closer to the glass interface while grabbing fluorescence images at each location. At each step, the automation program thresholds the images to a pre-determined intensity cutoff which is about 8 times of mean intensity of the whole image at each individual z location. Panel B shows the thresholded fluorescence image of the cell body. In the thresholded fluorescence images, the automation program looks for objects with circular shapes (red circle in Panel B) having diameters between 2 µm to 6 µm (dashed circles in Panel B). The red circle shows the detected cell-body. The dashed circles refer to the lower and upper limits of detected cell body diameter. Panel C shows the fluorescence image of the cell body relocated to the center of the FOV. After determining the relative location of the detected cell body compared to the center of the FOV, the software program moves the cell body to the center of the FOV for further image processing steps.

The automation software could perform axotomies on both ALM neurons. Namely, the surgeries were performed either on the right side of the worm targeting the ALMR or on the left side targeting the ALML. The ALM process ran anteriorly from the soma located close to the centroid of the worm, as shown in FIG. 9, panel A. Within each worm, axons from the ALML and ALMR neurons run along opposite sides of the body, while the AVM neuron travels along the ventral cord of the worm. Since *C. elegans* crawl on either side, the ALML and ALMR are situated in approximately the same vertical plane on opposite sides of the worm (FIG. 9, panel B). The axon of the AVM will lie in a different focal plane than either of the two ALM axons and is also outside the vertical plane that roughly passes through both ALMs. Therefore, either the ALMR or the ALML will be closer to the objective lens, depending on which side of the worm is pressed against the coverglass. FIG. 8 and FIG. 9 (panels C-F) illustrate an example axotomy where the ALM axon closest to the objective lens was automatically chosen as the target during surgery. Note also that when surgeries are performed on ALMs, no distinction is made between the ALML and ALMR.

The automated identification and targeting of axons in the small FOV was a three-step process. First, circle detection was performed via coarse focusing to identify a cell-body in the small FOV. A fine focusing was then performed and the targeted neuron was identified by detecting the axon at the sides of the neuron. Finally, the axon was moved into the laser ablation volume by adjusting the focus (z axis) and then bringing the axon to the correct position (y axis). By re-adjusting the z axis in the region of ablation, errors resulting from imprecise leveling of the worm are minimized.

Detection of a cell-body through coarse focusing proceeded as follows. After the approximate location of the ALM was determined in white light by finding the worm's centroid using the 5× objective, the 63× lens was moved into place, in only fluorescence illumination (white light was turned off), and the focal plane was positioned at the worm-glass interface. The translation stage was then stepped in 2.5 μm increments in the z-direction into the worm, and towards the in-focus location of the bottom-most ALM neuron until a circular shape was detected, corresponding to the cell body (FIG. 8). To carry out this detection, the software collected fluorescence images of the GFP labeled neurons at each 2.5 μm z-step and thresholded them to a pre-determined intensity cutoff which is 8 times of mean intensity of the whole image at each individual z location. The cutoff was determined empirically until the software could successfully detect a cell body. This cell body-locating process provided a fast method for roughly locating a z-position just short of optimal focus using a large translation step size. FIG. 8 shows an example where the program located the cell body and moved the stage to bring the cell body to the center of the 63×FOV close to the location of the laser spot.

Fine focusing on the targeted neuron then proceeded as follows. To determine the z-location of best focus, the variance of pixel intensity of each frame was used as the focusing function for direct image-to-image comparison from a z-stack collected at 0.5 μm steps using the piezoelectric actuator for translation (FIG. 9, panel C). The image with the highest variance of pixel intensity correlates to the most in-focus z-position. The sample variance of pixel intensity for each frame in the stack was defined as $$s_{MN}^2 = \frac{1}{MN} \sum_{i=1}^{M} \sum_{j=1}^{N} [I_{ij} - \bar{I}], \tag{1}$$

where $I_{ij}$ is the intensity of a single pixel in the image and $\bar{I}$ is the average pixel intensity of an M×N array of pixels. Before the variance of intensity of each frame was calculated, a 2D Laplacian of Gaussian (LoG) bandpass filter was convolved with each image in order to simultaneously reduce high-frequency noise and enhance the intensity of the axon. The LoG-filtered image is given as:

$$f_{LoG(x,y)} = \nabla^2 g(x,y) * f_0(x,y), \tag{2}$$

where $$\nabla^2 g(x, y) = \frac{x^2 + y^2 - 2\sigma^2}{\sigma^4} e^{-\left(\frac{x^2+y^2}{2\sigma^2}\right)}, \tag{3}$$

$f_0(x, y)$ is the pre-filtered image.

By passing through the point of largest intensity variance, the optimal focus for performing axotomies was determined. After locating the device at the best focus, the automation program created two small rectangular Region-of-Interests (ROI) on the left hand and right hand sides of the cell body to determine the relative location of the axon with respect to soma (shown in FIG. 9, panel D). The program then looked for the straight edges on each side. The existence of a straight edge is what differentiates the ALM neuron from the other nearby neuron, AVM. After determining the axon location and verifying that the cell body is the neuron of interest, namely one of the ALM neurons, the translation stage goes 60 μm in the corresponding direction along the axon (FIG. 9, panel E).

In the final step before axon ablation, the axon-of-interest was brought to the focus of laser spot by fine focusing. The automation software collected z-stack images at 0.5 μm steps using the piezo-actuator and searched for the highest pixel intensity variance. The piezoelectric actuator then moved to the precise y-position of the axon so that the axon was well aligned with the ablation target, given an axon diameter of ~300 nm. The $1/e^2$ diameter of the ablation spot was estimated to be ~620 nm. With the 63× objective, these dimensions correspond to three and six pixels respectively, giving a positioning tolerance for axotomy of approximately one pixel on either side of the axon. Due to the positioning hysteresis of the piezoelectric actuators, a closed-loop proportional control algorithm was incorporated based on imaging to drive the actuators. Briefly, the CCD captures the focused image, and then processed the image to find the sub-pixel center of the axon in the y-axis. The distance on the image in pixels between the axon center and the ablation spot was converted into a physical distance based on pre-calibration, which in turn served as a feedback to the closed-loop control that commanded the distance that the piezoelectric actuator translated. The process was repeated until the axon was within ~1 pixel from the ablation target. FIG. 9, panel F illustrates stage locations (x, y, and z) as a function of time for typical auto-focusing and axon positioning.

*C. elegans* Survivability and Axonal Reconnection Success Rate on a Chip

Figure 11:
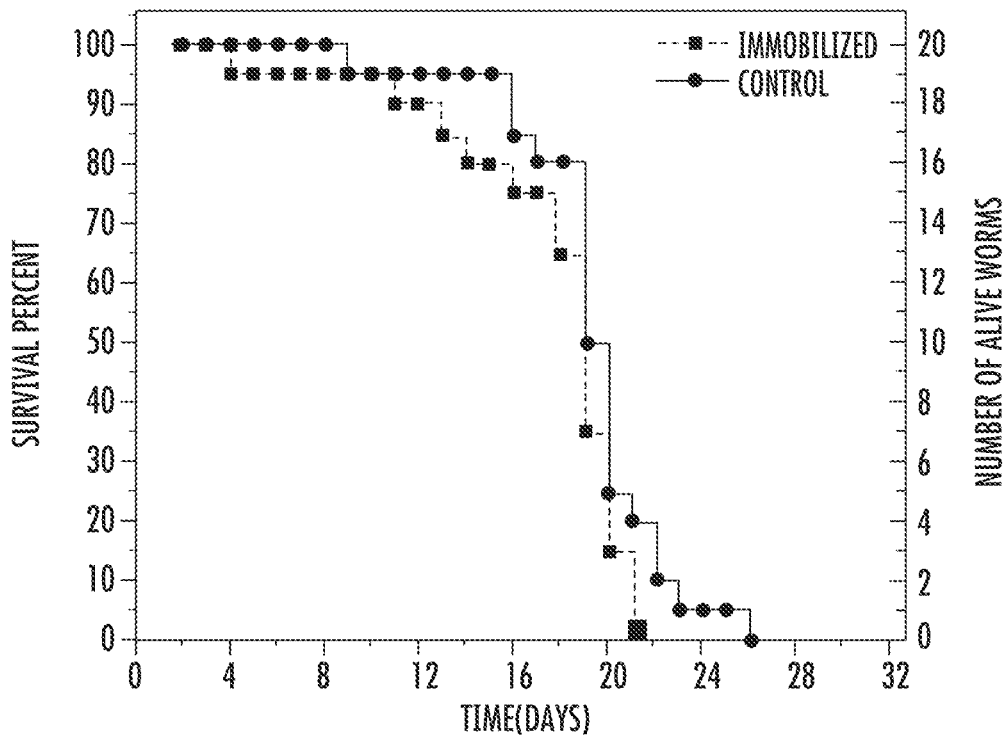
FIG. 11 is a graph plotting the percent survival of a group of worms immobilized in the microfluidic sample processing element shown in FIG. 5A with an applied pressure of 155 kPa for 30 seconds (black dashed trace with squares, n=20) and a control group (gray solid trace with circles, n=20) as a function of time (days).

To determine the effect of the immobilization procedure and the valve actuation in the microfluidic chip, a full cycle of valve actuation was performed as described above. Differently from the general automation progress, worms were trapped for 30 seconds at a pressure of 155 kPa. The same synchronization and cleaning procedure were used for the control group and trial group. The trapped worms were collected on NGM pads and compared with the control group. The viability of each population was evaluated every 24 hours. The worms were transferred to new NGMSR pads whenever needed. FIG. 11 is a plot illustrating the daily change in survivability rate (measured as survival percent) for the control group and the trapped group. A Log-Rank test was used to determine the difference between the viability of trapped group and control group. No statistically significant difference was found (P=0.71) between two groups.

Figure 10:
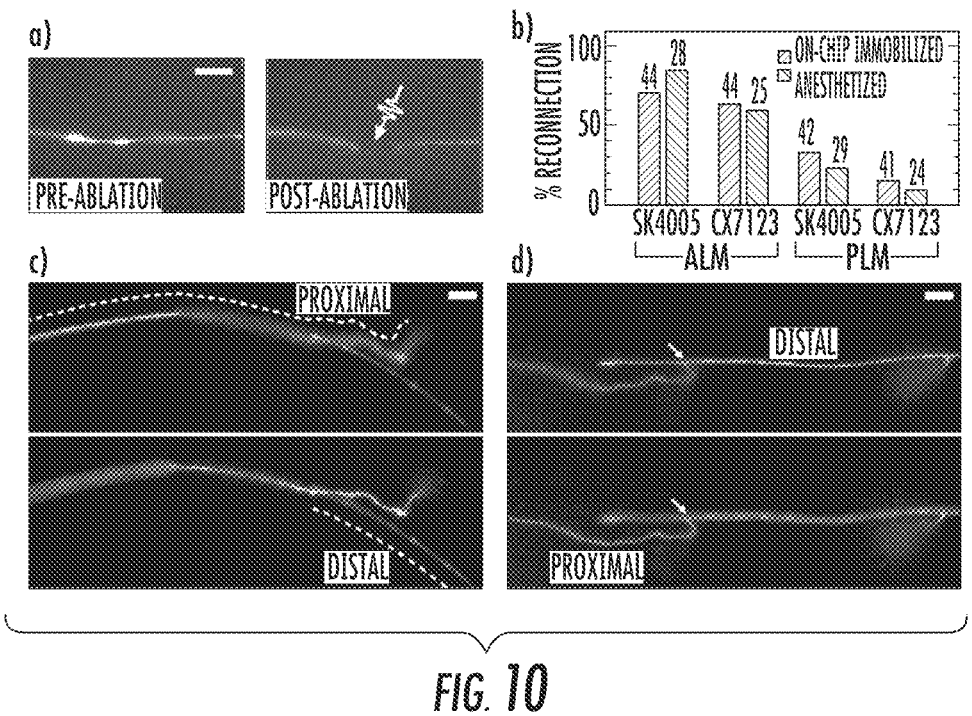
FIG. 10 illustrates the process of axonal reconnection following automated axotomies performed using the microfluidic sample processing element shown in FIG. 5A. Panel A is a fluorescence micrograph illustrating ALM neuron of a worm before and after laser ablation. Rates of neural re-growth with reconnection after axotomy performed using the microfluidic sample processing element shown in FIG. 5A were compared to rates of neural re-growth with reconnection after axotomy performed by manual ablation on agar pads using anesthetics. Two different *C. elegans* strains were evaluated, with axotomies being performed on ALM and PLM axons. After 24 hours of post-surgical recovery at 20° C., the axotomy sites were re-imaged to check for signs of re-growth and reconnection. Panel B is a plot of the percent reconnection observed for different *C. elegans* strains having axotomies performed by automated ablation (black bars) or manual ablation (gray bars). Panel C includes fluorescence micrographs taken in two different focal plans illustrating neural re-growth with a lack of reconnection after axotomy. Panel D includes fluorescence micrographs taken in two different focal plans illustrating neural re-growth with reconnection after axotomy.

To determine axonal reconnection rates following laser axotomy using the microfluidic sample processing element (FIG. 10, panel A), the worms were ejected from the microfluidic device, collected in a tube filled with M9 buffer, and then transferred to seeded agar plates for recovery. After 24 h of post-surgical recovery at 20° C., the axotomy sites were re-imaged to check for signs of re-growth and reconnection. Axonal reconnection rates in the ALM neurons after axotomies performed by either the automated surgery platform with physical trapping or by manual ablation on agar pads using anesthetics for immobilizing the worms were compared (FIG. 10, panel B). Two primary criteria were used to describe robust reconnection: (i.) proximal re-growth trajectories intersecting the distal axon and (ii.) a lack of beading or fragmentation in the distal axon that normally marks the beginning of Wallerian degeneration. For example, re-growth with a lack of reconnection is evident in the images taken at two focal planes shown in FIG. 10, panel C, whereas reconnection by the proximal end of the axon is clearly observed in FIG. 10, panel D. As shown in FIG. 10, panel B, no statistically significant differences in reconnection probabilities between ALM axons severed with the automated approach and those cut with manual surgery using anesthetics was observed.

Conclusions

An automated microfluidic platform for performing laser axotomies in living *C. elegans* has been designed. No statistical differences for reconnection probabilities between axotomies performed manually and with our automated approach were found. Synchronized valve and flow progression allowed rapid transport and immobilization of worms in a serial manner. The automated platform used image processing algorithms for locating and targeting axons for ablation. The performance of axotomies was up to the standards likely required for productive, high-throughput screening studies. This automated platform provides an opportunity to perform high-throughput genetic screening to identify the molecular mechanisms involved in inhibiting or promoting nerve regeneration and degeneration. With slight modifications of the image processing algorithms, the automated platform can easily ablate cell bodies of the targeted neurons as well for phenotypical studies.

Example 3: Trapping Chambers Containing One-Way Particle Flow Valves

Device Description

Example trapping chambers containing one-way particles were prepared. The trapping chambers can be incorporated in, for example, sample processing element or devices designed to trap and/or process multiple unique populations of model organisms in parallel while maintaining segregation between the populations.

Figure 14A:
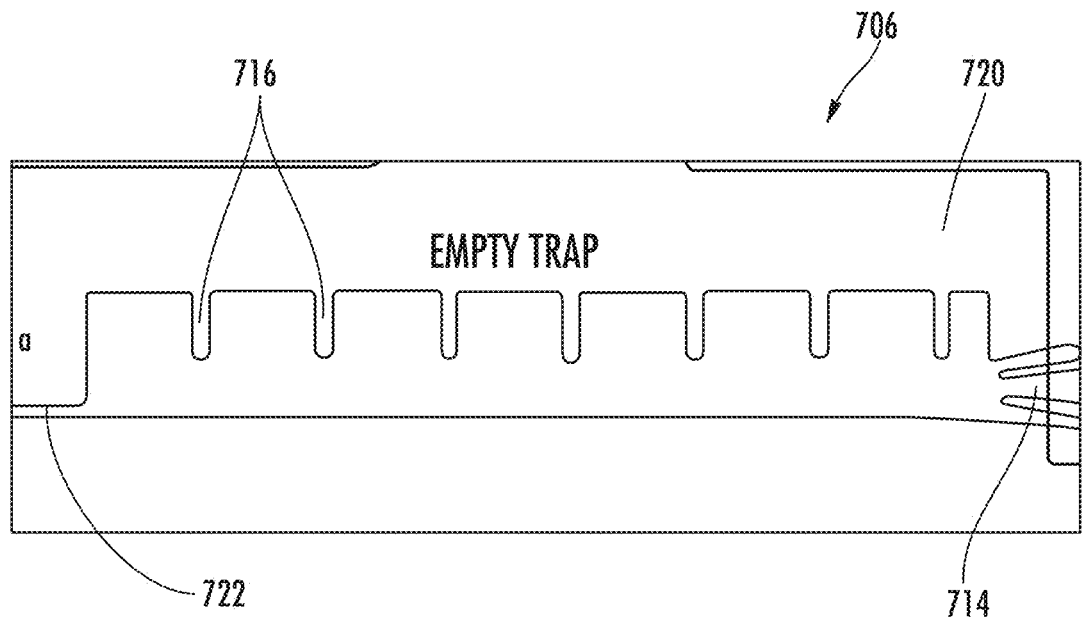
FIGS. 14A-14C are photographs illustrating a trapping chamber configured to be incorporated in the microfluidic sample processing element illustrated in FIG. 13.
Figure 14B:
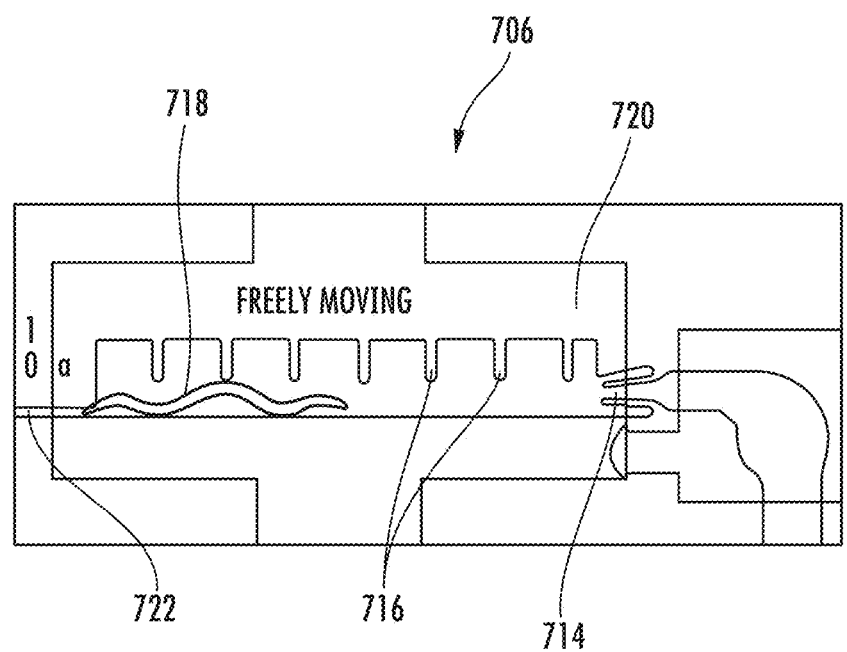
Figure 14C:
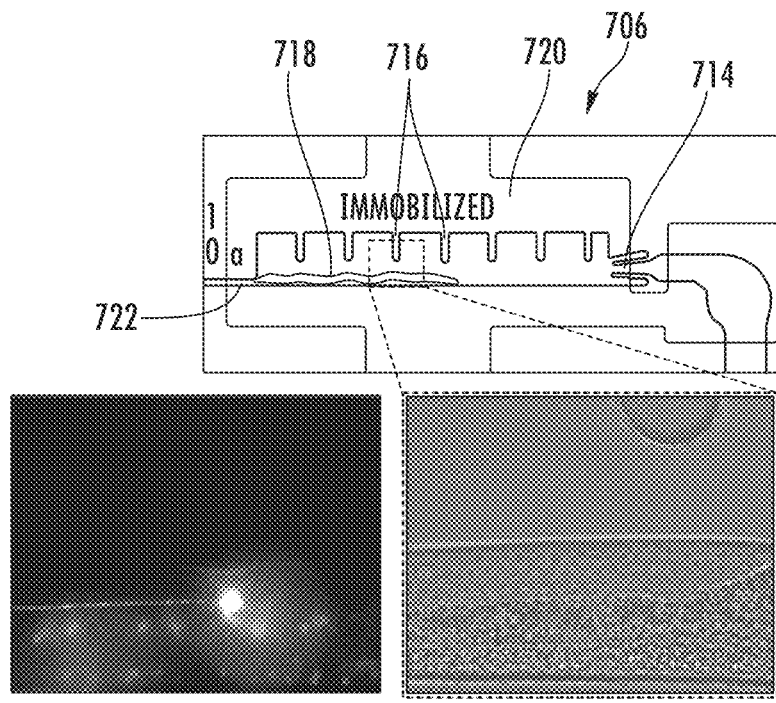

An example trapping chamber is illustrated in FIG. 14A. The trapping chamber (706) can comprise a one-way particle valve (714) configured to control the flow of a multicellular organism (718) between the outlet channel (704) and the trapping chamber (706), and an exit channel (722) fluidly connected to the trapping chamber (706).

Above these trapping chamber resided a deformable membrane (720) that deflected toward the channel floor when pressurized to immobilize the animal (718) against one of the channel walls. Multiple protrusions (716) extended from the channel wall opposite of the sidewall that the worm rested against during immobilization. These restrictions kept the animal in a repeatedly optimal orientation for imaging and nanoaxotomy by ensuring the animal's entire body was resting against one sidewall of the immobilization trap when the membrane was pressurized. This orientation ensured that the worm's body was not unfavorably crushed by immobilization membrane. Another set of protrusions (one-way particle flow valves, 714) at the entrance of the immobilization traps were orientated such that animals could easily enter the traps but could not easily exit between immobilization steps.

Device Fabrication

Standard soft-lithography techniques were used, with some modifications to fabricate the two-layer microfluidic device described here. The bottom layer that transports the *C. elegans*, is hereafter termed as the "flow layer." The top layer that when pressurized both immobilizes the worms and actuates the valve-like structures on the chip will be referred to as the "control layer."

Briefly, SU-8 resists (MicroChem) were used to create molds for the polydimethylsiloxane (PDMS; Sylgard 184, Dow Corning Corp.) microfluidic structures. To begin, SU-8 2025 was spin-coated onto a 4" silicon wafer to a thickness of ~35 μm and the flow layer was patterned with a photomask using the recommended processing protocols given by the manufacturer. The same process was repeated to create the valve control layer on another 4" wafer, which was ~50 μm in thickness. The wafers with the developed SU-8 molds were modified with a fluorinated silane (SIT8173.0, Gelest Inc.) that served as a release agent. All film thicknesses were verified with a stylus profilometer (Dektak 6M, Veeco).

PDMS (at 10:1 resin:crosslinker) was thoroughly mixed, degassed in a vacuum oven at room temperature, poured onto the control layer mold to a thickness of ~5 mm, degassed again, then cured at 75° C. in an oven for 30 minutes. To create the flow layer, PDMS was spin coated onto the flow layer mold at 1700 rpm for 33 s and allowed to rest at room temperature for 5 min, resulting in a uniform ~50 μm-thick PDMS layer with an approximately 20 μm-thick PDMS film covering the top of the SU-8 features. The PDMS on the flow layer mold was then partially cured on a hotplate at 75° C. for approximately 13 min. The thick control layer was aligned and bonded on top of the partially cured flow layer mold with the aid of a stereoscope. To improve the bonding strength between the two PDMS layers, the wafer was placed in an oven at 65° C. overnight.

The two-layer PDMS device was then peeled from the flow layer mold, and then 23 gauge holes were punched through the PDMS for making external fluidic connections. The device was then bonded to a 25×50 mm no. 1.5 cover slip using the same $O_2$ plasma conditions described above and finally placed in an oven at 65° C. for 4 h to enhance the PDMS-glass bonding. Sterile polyethylene tubing (Intramedic) was connected to the device using 22 gauge steel couplers (Instech Solomon) inserted into the punched PDMS holes, and if necessary, the connection was sealed with a small amount of acrylic glue prior to pressurization.

Example 4: A 'Plug and Play' Sixty-Four Well Microfluidic Delivery Device

To facilitate large scale high-throughput screens sample populations, systems should maximize the number of samples they can process while maintaining compatibility with current automated bio-screening platforms, such as robotic liquid-handling systems that use standard well plate sample holders. Provided herein is a microfluidic chip and corresponding gasket system that make a significant step towards bridging this gap. The chip utilizes the maximum area of a 96-well plate footprint to house 64 sample wells for holding populations, in addition to on-chip valve inputs. Subsequently, the gasket system not only pressurizes the wells to drive population delivery, but also brings individual pneumatic inputs to the on-chip valves. This design makes the system behave in a plug and play fashion. After loading samples into the wells, one simply secures the chip inside the gasket without needing to plug in many semi-permanent tubing inputs for each valve. A new automation software and electronic pneumatic system regulate flow such that faster, more complete, and more consistent delivery rates are achieved: 94% of the loaded population in a given well is delivered from a given well.

Overview

Figures 18A, 18B, 18C, 18D:
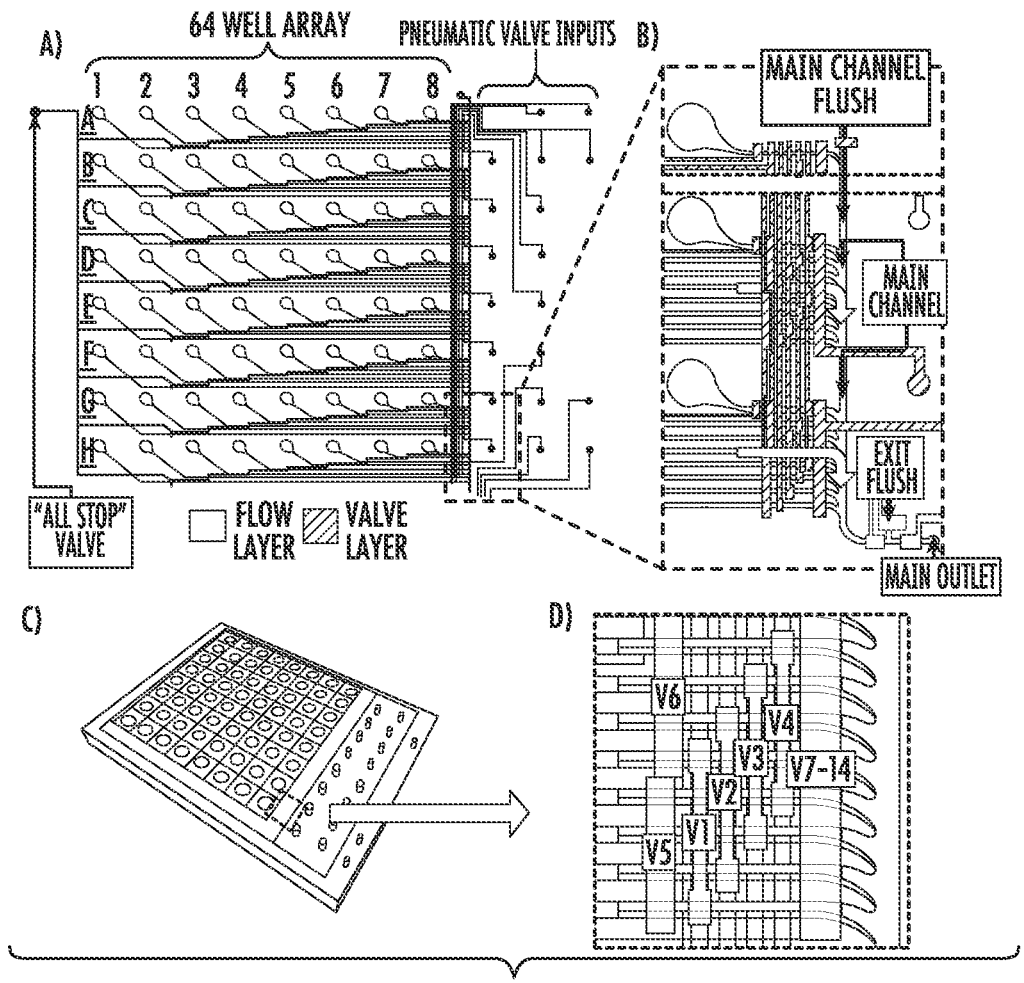
FIG. 18 illustrates a 64 sample well microfluidic device. Panel A is a schematic of the two-layer microfluidic device with the array of 64 well plate-format reservoirs and multiple pneumatic valve inputs. The flow layer houses the populations and the valve layer contains the pneumatic on-chip valves inputs. Each well is referenced by the row (A-H) and column designation (1-8). Panel B illustrates certain functional areas of the device: worm populations arrive to the Main Channel from well reservoirs one-by-one via the paths indicated by the arrows. Flush channels help with completing delivery without mixing. Panel C is an image of the microfluidic device with a section of multiplexed valves that regulate a row of reservoirs in the array indicated by the dashed square. Panel D is an image of the interface of well channels from a single row in the reservoir array with the Main Channel. The set of corresponding multiplexed on-chip valves is indicated by the gray outlines and corresponding valve names (V1-V14).

A microfluidic platform that can handle multiple populations of organisms (e.g., *C. elegans* worms) and that is compatible with well plate handling systems is described. The device is illustrated in FIG. 18. The device contains 64 well plate-format sample reservoirs, each of which can hold a distinct worm population. The device interfaces with pneumatic control inputs in a simplified plug and play fashion. These design elements enable simpler operation of the platform and will facilitate high-throughput screens on imaging platforms at a much larger scale.

We previously characterized the fluidic flow rates, worm population delivery rates, and animal viability of the 16-well device. This first iteration was capable of delivering each population in less than 5 seconds, an order of magnitude faster than the most advanced worm population delivery systems. Applying the knowledge gained while designing this device, we created a system with a four-fold increase in well plate-format reservoirs (64) and a more robust gasket apparatus to improve throughput and usability. We also updated the hardware and software components to give more consistent and controlled worm delivery rates. In the first generation system, we were able to deliver between 80-93% of given populations loaded into the on-chip wells in under five seconds. We engineered this second iteration platform with larger channel cross-sections and integrated dynamic electronic pressure regulators to achieve delivery at twice the speed of the 16-well device at an average rate of 94% of the total population loaded in each well.

The 16-well devices described above were capable of delivering each population in less than 5 seconds, an order of magnitude faster than the most advanced worm population delivery systems. The 64 well plate-format 'plug and play device' described below provides a four-fold increase in well plate-format reservoirs (64), and a more robust gasket apparatus to improve throughput and usability. The hardware and software components were also update to give more consistent and controlled worm delivery rates. In the first generation system, between 80-93% of given populations loaded into the on-chip wells were delivered in under five seconds. The 64 well plate-format 'plug and play device' with larger channel cross-sections and integrated dynamic electronic pressure regulators achieved delivery at twice the speed of the 16-well device at an average rate of 94% of the total population loaded in each well.

A main innovation in this second generation system is the pneumatic gasket. To make the platform more amenable to automated fluidic plate-handling systems used in high-throughput biological research and drug screens, the number of tubing ports plugged into the microfluidic chip was reduced. Instead of delivering pressurized fluid to the on-chip multiplexed valves via tubing, air-pressure was delivered through the gasket via individual ports to small liquid-filled wells built into the chip that interfaced with the on-chip valves. These ports were embedded in the gasket and sealed around each on-chip valve input with a small O-ring. This approach made the chips more modular and transportable between experimental steps, so they could be loaded with up to 64 *C. elegans* populations via conventional pipetters or liquid handling systems. An "all-stop" valve was integrated at the interface of each well-plate reservoir to the microchannels to prevent animals from escaping from the wells into the chip when the device was not in the gasket. After filling the chip with worm populations, the gasket clamp firmly sealed the gasket to the chip, and subsequently, the pneumatic inputs were activated to commence population delivery to an automated imaging platform.

Design and Testing

The 64-Well Population Delivery Chip

The 64-well microfluidic multiplexer chip's design is illustrated in FIG. 18. As in the 16-well chip described above, the device included several conical well plate-format sample reservoirs connected to a single microfluidic channel patterned in PDMS, and flow in these channels could be regulated in any desired configuration by a multiplexed system of on-chip pneumatic valves. Similarly to the previous design, each channel originating from a well plate format reservoir intersects with the Main Channel that is connected to flush inputs residing upstream of all of the well channel intersections (Main Channel Flush) and near the exit of the device (Exit Flush) (Panel B of FIG. 18).

Microfluidic Chip Well Channel Array and Valve Design

In the 16-well chip there were four well reservoir "groups" in the device that were organized by column in the reservoir array and corresponding valves regulated fluid flow in these columns. Multiplexed valve control relied on two valves opening at once to permit flow through a specific well. One of these valves would choose the row (V1-V4) and the other valve would choose the column (V5-V8) in the well plate format reservoir array. For example, opening V6 would permit flow through column 1 only, while V5, V7, and V8 were closed. Concurrently, opening V1, while V2-V4 were closed would allow flow through third row down in the well array (Wells 3, 7, 11, and 15). Thus, only opening these two multiplexed valves would exclusively allow flow through Well 3. As previously described, this design coupled with the proper order of serial population delivery conferred specific advantages to minimizing the number of flush back steps needed and eliminated cross-contamination during the automated delivery sequence.

Similarly, in the 64-well device, the wells were organized into eight column groups, each consisting of eight wells. In this case, single valves controlled flow in two out of the eight columns of the device, and an additional valve would be regulate one of these two valves in every subset of two columns (refer to Table 4 below and Panel D of FIG. 18).

TABLE 4

Valve Regulation Column Groups. FIG. 18 shows valve and column locations in the device.

| Shared Valve | Column Number in Array |
| --- | --- |
| V1 | 1 and 5 |
| V2 | 2 and 6 |
| V3 | 3 and 7 |
| V4 | 4 and 8 |
| V5 | 1, 2, 3, 4 |
| V6 | 5, 6, 7, 8 |

Valves V5 and V6 are responsible for choosing between the two columns regulated by each of the above valves. For example, exclusively opening V1 and V5 opens flow through only through column 1 in the 64-well device. Simultaneously, each of the valves, V7-V14 specify which one of the 8 rows (A-H, Panels A and D of FIG. 18) is being addressed. The valve arrangement motif in Panel D of FIG. 18 shows how all of the aforementioned valves are arranged for each row in the array (rows A-H). This modular structure simplified designing the device and the automation sequence, which will be discussed shortly. However, based on the binary multiplexing logic, 64 wells should only require 12 multiplexed valves for flow regulation ($2 \times \log_2(n)$ valves controls "n" channels), while our system uses 14. Having two fewer valves may have slightly simplified the hardware design, but would have forced us to give up a more straightforward valve design with the modular motifs for each row in the well reservoir array.

Well Plate Reservoir "all-Stop" Valve

In terms of compatibility with liquid handling systems, the chip's "all-stop" valve prevented samples loaded into the wells from flowing into the device microchannels before interfacing with the gasket (Panel A of FIG. 18). This all-stop valve was actuated via a stand-alone pneumatic input that did not require an external feed pressure. This configuration permitted off-platform loading of the chip's 8×8 array of well plate-format reservoirs without sample populations escaping the wells into the Main Channel or cross-contaminating other samples. Once the populations were loaded into the device, all of the other on-chip valves could be closed via the gasket to stop flow and sample escape throughout, permitting release of the "all-stop" valve.

Microfluidic Device Fabrication

The flow layer mold was fabricated with larger channel heights to achieve faster flow rates in comparison to the 16-well device (~55 μm versus ~110 μm). Channel collapsing events during PDMS-PDMS bonding of the flow layer to the spin-coated control layer were almost completely eliminated. For the flow layer, the ratio of the channel height to width in the 16-well device was 1:6, where as the 64-well device had a ratio of ~1:3. The taller channel heights prevented collapsing and bonding of the channel ceiling to the substrate in the most parts of the device. With the 16-well iteration, extra care had to be taken during this bonding step to avoid these collapsing events by applying very limited pressure to the PDMS piece in crucial device locations.

Figures 19A, 19B, 19C:
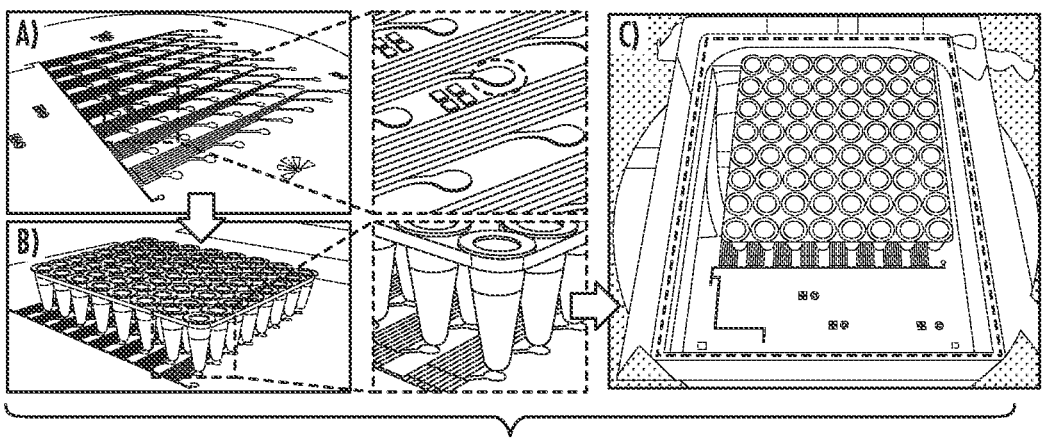
FIG. 19 illustrate the process of making the 64 sample well microfluidic device illustrated in FIG. 18. In Panel A, a six-inch silicon wafer is shown with the patterned photoresist to mold the PDMS features. A sample input port is highlighted with the blue circle. In Panel B, an 8×8 well section of a PCR plate is aligned with the population input ports in the mold. In Panel C, an acrylic barrier piece (dashed lines) is then placed around the area patterned in photoresist, and PDMS is then poured into its inner boundary.

An 8×8 section of a PCR well plate was used for molding the well reservoirs into the chip (Panels A-C of FIG. 19). This technique greatly simplified well mold alignment with flow layer population input ports (Panel A of FIG. 19). During fabrication of the previous 16-well device, an acrylic guide was used to individually position 16 P-1000 pipette tips at precise positions on the resist mold. This procedure required a great deal of manual dexterity and could require up to an hour to complete. It was difficult to position one pipette tip on the mold without creating movement in the acrylic positioner and displacing a previously placed pipette tip. Using the single 64-well section of a PCR plate to mold wells in the flow layer required much less time and concentrated effort since this process only required positioning a single object in the correct position, as opposed to 16 or 64 pipette tips.

To ensure proper alignment of the device's flow layer piece to the control layer during bonding, the flow layer mold was scaled to account for the inherent shrinkage that occurs in PDMS due to exposure to specific temperatures and baking times. This scaling was necessary to accommodate for the alignment tolerances of the densely arranged valve and channel features in the large area design. Based on previous studies, it was predicted that the device area of the flow layer piece in the plane of the silicon mold would isotropically shrink across the planar device area by ~1.3% from the original mold area. The shrinkage forced us to purposely increase the area of the photoresist patterned mold by the predicted shrinkage factor to guarantee that channels in the flow layer aligned adequately with valve channel patterns in the control layer. When alignment was properly executed, all of the on-chip valves overlapped sufficiently with the designated flow layer channels. An important factor in this procedure was having simultaneous confirmation that alignment markers on opposite ends of the device were properly placed. Thus, two stereoscopes were used to visualize the markers during bonding. Having one stereoscope coupled to a camera that displayed its field of view on a nearby monitor and the other serving as a manual scope proved sufficient for alignment.

Creating such a large area device required modification of the glass to PDMS bonding procedure to minimize bonding defects and valve leakages. In particular, when both the large area PDMS device (~8 cm×~10 cm) and the glass were placed in the plasma chamber, maintenance of uniform plasma across the entire surface of both pieces mostly likely became more difficult to maintain. Without uniform exposure to plasma, regions of poor bonding between the glass and PDMS resulted, causing cross-talk between valves in the device. These defects were minimized by first exposing the glass and then the PDMS piece to the plasma separately, so that these pieces could be placed in the central area of the plasma chamber and receive a relatively strong and uniform oxygen plasma dose across their surfaces.

Gasket System Design Considerations

The main design goals of the gasket system in 64-well device platform were to simplify the system operation workflow and increase the platform's amenability to high-throughput liquid handling systems. Improvements to usability were achieved by replacing the semi-permanent tubing interfaces used to operate the on-chip valves in the devices described above (which are ubiquitous in the microfluidics field) with air-delivery lines permanently built into the gasket itself (FIGS. 20 and 21). Each time a new chip was loaded into the gasket system, there was no need to manually plug in each valve input to the chip by hand because the air-delivery lines in the gasket were designed to align and seal with the on-chip interfaces. By reducing the number of tubing inputs and creating a gasket and computer-control system that could still individually address each valve and consequently each on-chip well plate reservoir, this gasket system now acted more as a 'plug and play' platform into which the microfluidic multiplexer chip could be quickly inserted.

Acrylic Gasket Component

Figures 21A, 21B, 21C:
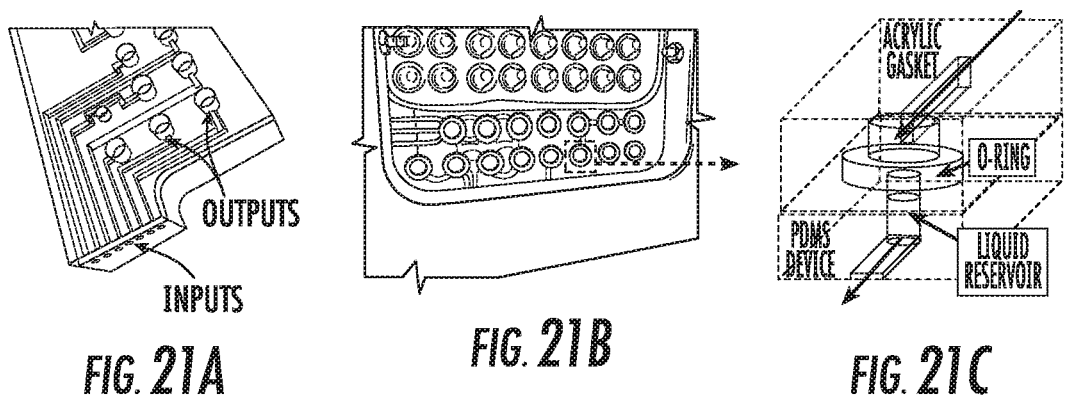
FIGS. 21A-21C illustrate pneumatic on-chip valve actuation from the gasket system.

The gasket system was composed of custom machined parts. A two-layer acrylic-rubber hybrid gasket delivered pressurized air to the microfluidic on-chip valve inputs and well reservoir array. The top layer was an acrylic piece consisting of machined indentations that would serve as air delivery lines. A thinner acrylic slab was then bonded on top of the surface of the thicker acrylic part to cover the indentations and effectively create sealed channels. Precisely positioned holes in the thin acrylic piece served as pneumatic exits for these channels where the gasket interfaced with the microfluidic chip. The placement of the openings allowed air to travel from the gasket's pneumatic inputs to specific on-chip valves (FIG. 21). The openings on this second acrylic layer were bordered by rubber o-rings. When the clamp was tightened around the gasket and the chip, the hard rubber O-rings resisted the compression by vertically deforming the PDMS on the top surface of the chip and pressing against the gasket, creating a tight seal. These seals could resist up to ~207 kPa (30 psi) at the microfluidic valve interface (FIGS. 21B-21C) and ~138 kPa (20 psi) from the chamber above the well plate reservoir array (FIG. 21B).

Inside the gasket, there were 18 air-delivery lines to pressurize the fluid in each on-chip valve and the well plate-format reservoirs (FIG. 20). Vertical holes were drilled through the entire gasket at locations where tubing interfaced the chip to deliver liquid into the device for the flush channel inputs (Exit Flush, Main Channel Flush). Preliminary tests indicate that fluid inputs for flush channels could also be fed via a sealed gasket feed, as opposed to the metallic tubing interfaces plugged directly into bulk PDMS.

The dense packing of all of these various pneumatic interfaces on the bottom surface of the gasket required the use of the O-rings in order to maintain the seals. Originally it was projected that a thin layer of PDMS across this surface with air-access holes would be sufficient to create the necessary air-tight seals against the various inputs on the microfluidic device surface. This approach was used with the gasket for the 16-well device. However, the previous device's gasket was exerting compression force on much smaller area on the surface of the chip surrounding the well plate-format reservoirs when compared to the 64-well system. Secondly, the previous gasket was not required to seal small valve inputs that were located several centimeters from the clamping screws. The current gasket clamp exerts compression force directly on the outer perimeter of the gasket and relies on the rigidity of the gasket material to transfer this force to every interface between the gasket and the microfluidic chip. With PDMS between these junctures, pneumatic cross-talk and leakage between valve inputs occurred as a result of excessive PDMS deformation at pressures above ~207 kPa (30 psi). Instead, securing more rigid rubber O-rings directly to the acrylic surface and tightening the gasket clamp maintained all of the individual seals to the microfluidic chip across the required pressure ranges (FIG. 21).

The Gasket Clamp

A clamp sandwiched the gasket and the PDMS device (FIG. 20). This clamp was fabricated from two aluminum pieces that could reversibly latch to each other and compress the gasket and the chip together such that desired pneumatic input pressures were maintained. A single twist latch on each of the four sides of the top clamp piece fastened to corresponding hooks protruding from the bottom clamp piece. Twisting all four latches till they could no longer be displaced provided enough force to seal the corresponding pneumatic inputs to the microfluidic chip via the O-rings. The top clamp piece fit snugly onto a step machined onto the topside of the gasket for simple and repeatable positioning.

The gasket clamp had to be tightened to the highest degree possible without damaging the acrylic or the chip in order to guarantee adequate sealing and pressure maintenance, especially inside the chamber above the wells. Occasionally, subtle air leaks between the O-rings and the PDMS chip's surface were observed via submersion of the device in a water bath and tracking emerging bubbles, but the system maintained the desired pressures robustly.

Automated Delivery System Design

Several approaches were considered to achieve uniform and repeatable population size delivery across all of the well plate format reservoirs assuming that an equal number of worms were loaded in each well. One avenue could have been to design the microchannel geometries and dimensions in the multiplexer chip such that all of channels emerging from single wells had a uniform fluidic resistance across all channels. This approach would ensure that uniform pressure and timing parameters during automated delivery would result in equal fluid volumes and population sizes being dispensed from each well. However, achieving this would require building channels with variable widths and/or heights. Variable heights would have required the patterning of several layers of photoresist on a single mold; a time consuming process due to the multiple iterations of fabrication optimization. The variability of photoresist feature height typically seen in the patterning of even a single layer would have made achieving the desired dimensions challenging. Concurrently, varying the channel widths would require a range of dimensions that would have prevented us from spacing the reservoirs in the equal spacing of 96 well plate arrangement, unless a vastly different design was considered.

Thus, a robust approach was assumed that would minimize the time needed for delivery of a maximum proportion of the populations as quickly as possible, while simultaneously addressing the variability in feature sizes encountered in photolithography. Voltage-controlled pressure regulators were used to control pressure applied at junctures in the microfluidic multiplexer that would require variable pressure application to induce almost uniform delivery rates for each well in the device: the chamber above the wells in the gasket and the fluid reservoir coupled to the Main Channel Flush line. Experimentally measured flow rates were taken from each well, and used to deduce the potential time of flight for a given population of worms from each well plate format reservoir for a range of pressures. With this information, appropriate pressures to be applied at the on-chip wells and the Main Channel Flush via the automation software and electronic variable pressure regulators were selected in order to deliver the same proportion of each loaded population from each well in a minimal time period.

Flow Rates

To develop an automated sequence, the pressure dependent flow rates were characterized in certain functional areas of the device, chiefly through the well plate-format reservoirs and the flush channels. From this information in addition to the channel dimensions characterized during fabrication of the chip, estimates of fluid velocities and time of flight of the sample populations could be obtained. The required time to deliver populations within feasible pressure parameters to the exit of the device could then be determined.

Flow rates and time of flight through four representative wells in the chip were characterized. Looking at the schematic in Panel A of FIG. 18, it can be seen that up until the Main Channel intersections, every well channel in a given column (1-8) has the same length and architecture, and concurrently every row (A-H) of well channels has the same arrangement of eight unique channel lengths. Given the same pressure drop across the wells to the Main Outlet, the only major variable parameter in terms of flow rates between equivalent well channels of different rows (e.g. D5 versus G5) are the distances of their intersections with Main Channel from the Main Outlet (Panel B of FIG. 18). With these considerations in mind, the flow rates in the longest and shortest well channels (columns 1 and 8, respectively) in rows that were the nearest and farthest (rows H and A, respectively) from the Main Outlet were characterized to cover the full range of possible flow rates in the device.

Figure 22:
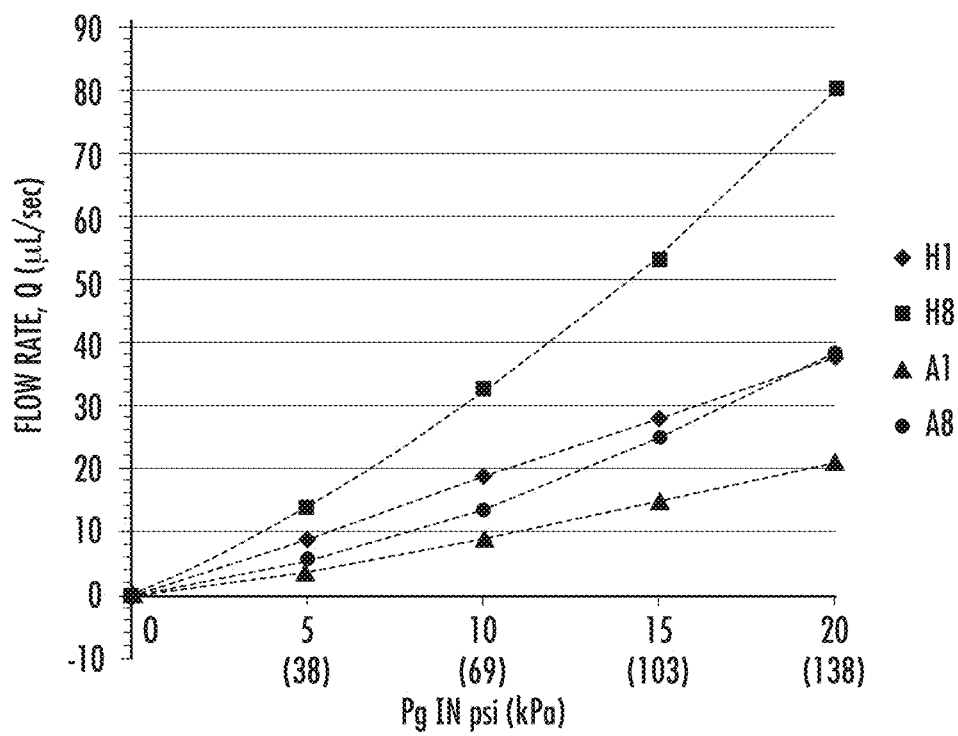
FIG. 22 is a plot of the measured fluid flow rates in four representative wells (H1, H8, A1, and A8) of the 64-well population delivery chip illustrated in Panel A of FIG. 18 as a function of applied gauge pressure at the gasket. The dotted lines are polynomial fits to the measured data.

The data shows that flow rates through Well H8 are the fastest because the path length from its well reservoir entrance is the shortest amongst all the wells in the device, resulting in the smallest fluidic resistance (FIG. 22). Concurrently, flow rates through Well A1 are the slowest in the device since its path length and fluidic resistance is largest of the wells. Based on the device design, all other wells should have flow rates for a given air pressure applied at their entrances that would fall somewhere between the flow rates measured for Well H8 and Well A1.

Figure 23:
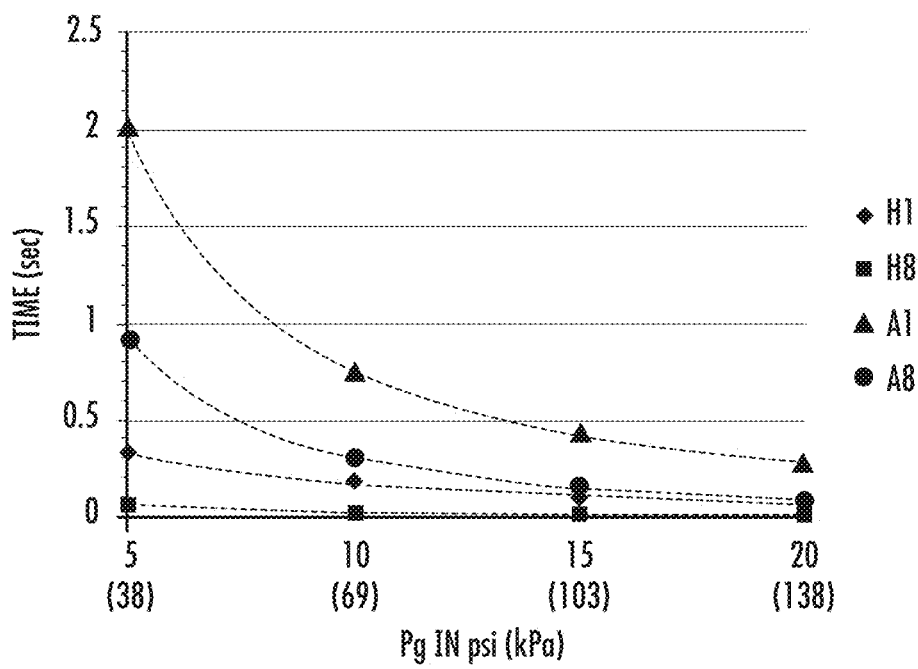
FIG. 23 is a plot of the time of flight from four well entrances (H1, H8, A1, and A8) of the 64-well population delivery chip illustrated in Panel A of FIG. 18 to the Main Outlet as a function of pressure applied at the gasket. The dotted lines are power law fits to the data.

Dividing the flow rates by the average channel cross-sectional area of a given well channel provided the average fluid velocity through the channel. Using this data along with the path length from well entrance to the Main Outlet, we could see that for pressures at 10 psi or higher applied to the gasket, all wells in the device had time of flights under 1 sec between the well and the Main Outlet (FIG. 23). This implied delivery could be achieved much faster than in the 16-well device, which needed around 2.5 seconds to initially move a majority of the population out of the well, followed by additional flush steps. The main source of flow rate improvement was due to doubling the channel cross-sectional areas across the device, thus decreasing the overall fluidic resistance.

Automated Delivery Sequence

Figure 24:
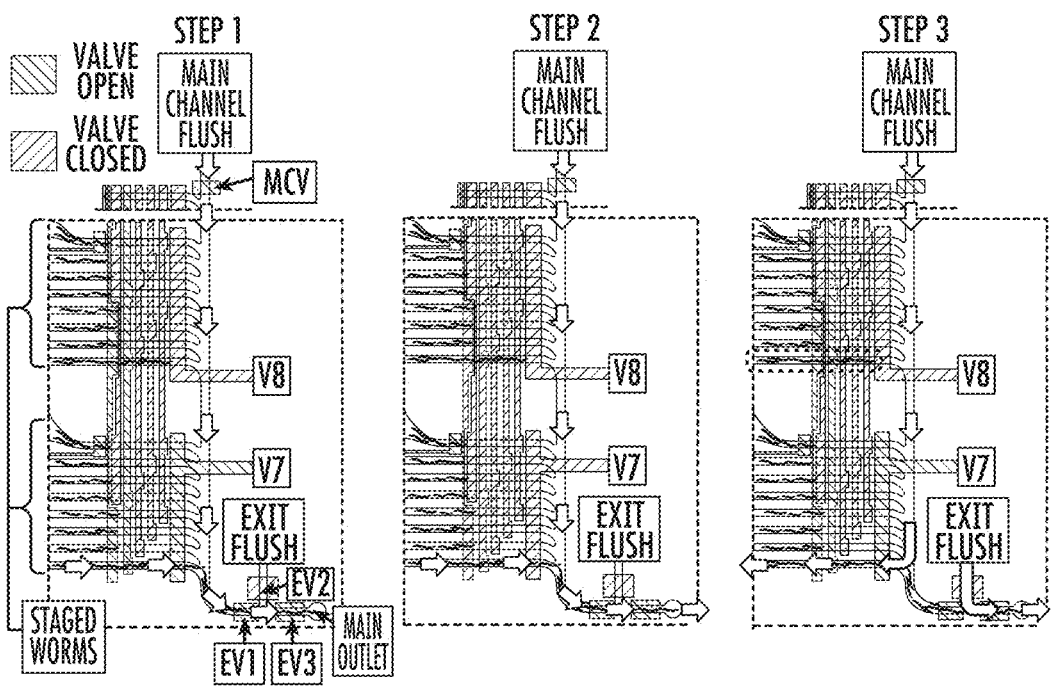
FIG. 24 is a schematic drawing illustrating the automated delivery sequence for delivery from Well H1 of the 64-well population delivery chip illustrated in Panel A of FIG. 18. Step 1: Worms (curved black line segments) loaded in the wells are staged near the valves closest to the well entrances. Appropriate valves open as the gasket is pressurized to send the population from Well H1 to the main channel, where Main Channel Flush then accelerates the worms' transport to the main exit. Step 2: Excess worms are cleared from the main channel by flow from Main Channel Flush. Step 3: Flow from Exit Flush delivers the worms from the Main Outlet to an off-chip location, as Main Channel Flush is simultaneously directed backwards to push remaining worms in the well channel back to Well H1. In the schematic for Step 3, a dashed rectangle indicates the next population to be delivered (Well GJ). An alternative version of Step 3 can be executed for the final well in a given column, such that all wells in the column receive a simultaneous flush back flow from the Main Channel Flush.

The steps of the automated delivery sequence for sending a population from a single well (Well H8) is shown in FIG. 24. Briefly, after worms from every well have been staged at the first set of valves nearest to their entrances (V5 and V6) the platform pressurizes the fluid in the wells and opens the corresponding valves to allow delivery of worms from Well H8 to the Main Outlet, while simultaneously sending pressurized fluid from Main Channel Flush toward the exit as well. Like the previous device, this flow from the Main Channel Flush prevents worms from spontaneously flowing in the wrong direction. After a majority of the population has passed the multiplexed valve section (V1-V14), these valves close and the Main Channel Flush continues to send fluid to push the worms to their desired location off chip and through the coupling tubing. This step also clears out any remaining worms out of the Main Channel. Finally, flow from Main Channel Flush is directed back towards the well to clear out worms caught between the multiplexed valves during Step 1. This is accomplished by opening the multiplexed valves and closing off the exit. Simultaneously, the Exit Flush continues the population delivery by sending flow through the Main Outlet to the external destination.

The third step in the automation sequence essentially executes Steps 3 and 4 of the sequence described above. This strategy saves a significant amount of time during the delivery process, while still ensuring that the various worm populations will not cross-contaminate. Table 5 describes the valve actuation scheme and timings for the sequence steps. Valve and fluid input names refer to components described in FIGS. 18 and 24.

TABLE 5

Timings for the automated delivery sequence applied to each well and device truth table for delivery from Well H1 of the Device shown in Panel A of FIG. 18.

| Step | Timing (s) | Gasket | V1 | V5 | V7 | EV1 | EV2 | EV3 | MCV | MCF | EF |
|---|---|---|---|---|---|---|---|---|---|---|---|
| 1 | 1.5 | 1 | 0 | 0 | 0 | 0 | 1 | 0 | 0 | 1 | 0 |
| 2 | 0.75-1.25 | 0 | 1 | 1 | 1 | 0 | 1 | 0 | 0 | 1 | 0 |
| 3 | 0.25 | 0 | 0 | 0 | 0 | 1 | 0 | 0 | 0 | 1 | 1 |

"1" indicates the valve/fluid reservoir is pressurized, while "0" means that it is not pressurized.
MCF—Main Channel Flush, MCV—Main Channel Valve, EF—Exit Flush, EV—Exit Valve.
All other valves not described here remain closed throughout this example.

As described above, the order in which the well populations were delivered played a role in eliminating cross-contamination events and minimizing the total time to deliver all 64 wells. The two main strategies used with the first device's delivery sequence were to deliver from wells that interfaced with the Main Channel nearest to the Main Outlet before those that interfaced more upstream and the other approach was to select the order of wells emptied based on column groups. This minimized the possibility that any number of worms from an undelivered population will infiltrate the spaces between the multiplexed valves and move them to a position that would allow them to contaminate another population during its delivery.

Figure 25:
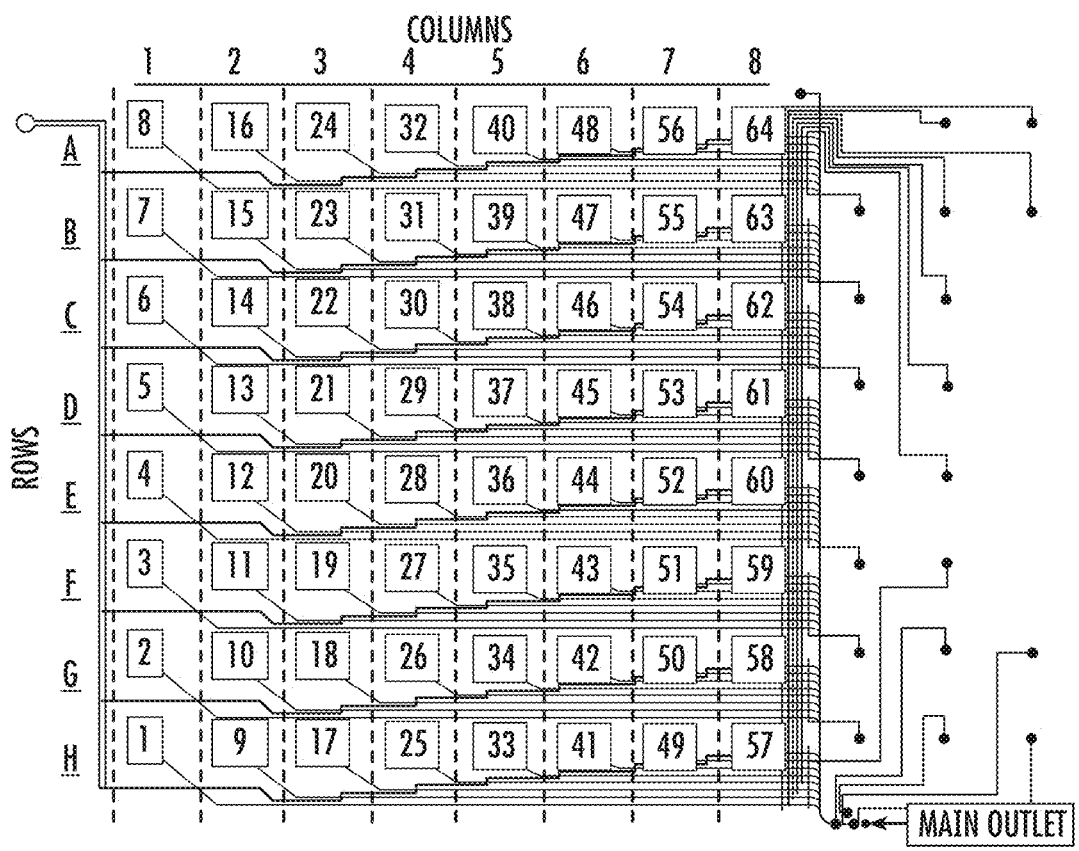
FIG. 25 is a schematic drawing of the 64-well population delivery chip illustrated in Panel A of FIG. 18 showing the optimized delivery order for emptying all 64 wells in the microfluidic device. Wells are labeled with their position in the serial delivery sequence during automated device operation.

Based on the device architecture and the sequence optimization considerations we developed an order for serially delivering from all 64 wells in the device. FIG. 25 labels each well based on its temporal position in the sequence. The progression of wells delivered ensures that each well in a given column is emptied before a well of another column is addressed, and the order guarantees that wells that interface the Main Channel closest to the Main Outlet will be emptied before their upstream counterparts. During the delivery sequence for the last well in a given column (any well in row A), the program executes a modified version of Step 3 in which flush back is performed on wells in the column in order to prevent any worms that have slipped past V5 or V6 from cross contaminating with subsequent samples.

Ultra-Fast Worm Population Delivery

Empirical measurements of flow rates through relevant wells in the device and initial tests with worm populations arrived at sufficient delivery times and pressures applied at the various pneumatically-driven inputs to achieve up to ~97% population delivery of the initially loaded population in under 3 seconds from the wells tested. Delivery through the four wells (A1, A8, H1, and H8) of the device were tested. Because of the device configuration, these represented the maximal and minimal flow rates per unit pressure applied to the gasket through their well channels and comprised the device's extremes for well channel distances from the Main Outlet. This strategy was meant to validate proper delivery from all wells in the device since the full range of critical parameters relevant to delivery rates would be evaluated.

Up to ~103 kPa (15 psi) pressure was applied at the gasket to the well reservoir array and varied the pressure sent to the Main Channel Flush fluid reservoir via the electronic pressure regulator to compensate for variable flow rates through the different well channels. This compensation was motivated by the finding that when the pressure applied to the well reservoirs through the gasket matched the pressure applied to the Main Channel Flush fluid reservoir during Step 1 of the sequence, worms occasionally would not even emerge from the wells, especially wells residing in row A. It was hypothesized that flow from Main Channel Flush overwhelmed or effectively blocked the simultaneous flow emerging from the well.

Figure 26A:
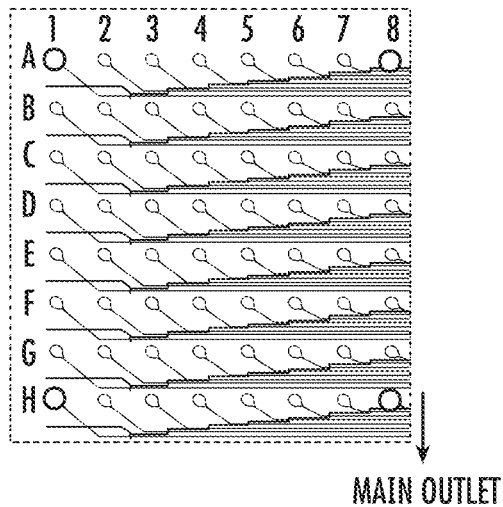
FIGS. 26A-26B illustrate worm population delivery rates for four representative wells in the 64-well population delivery chip illustrated in Panel A of FIG. 18.
Figure 26B:
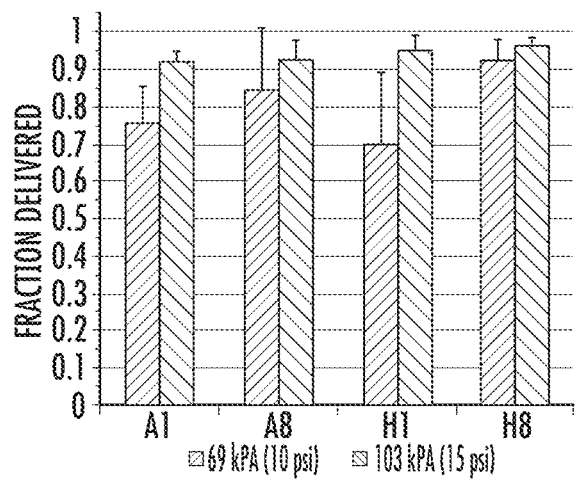
Figure 27:
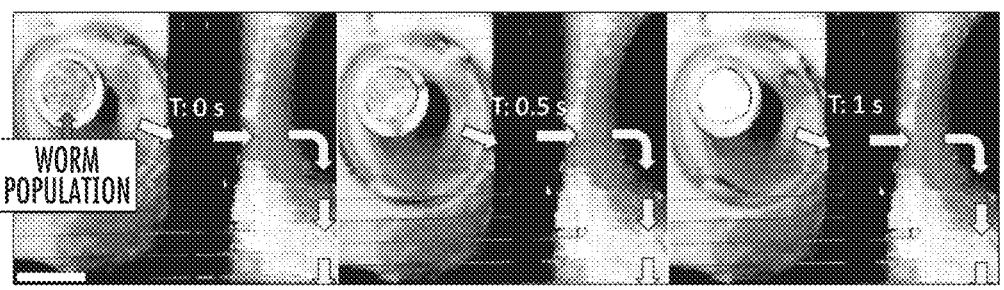
FIG. 27 illustrates ultrafast worm population delivery from a well in the 64-well population delivery chip illustrated in Panel A of FIG. 18. At time 0, worms have sunk to the interface of the well plate reservoir and the well channel. Delivery commences, and after one second the well is essentially empty. Scale bar is ~3 mm.

Applying variable pressures at the Main Channel Flush fluid reservoir enabled generation of fluid flow rates emerging from the Main Channel Flush that were a reduced fraction of flow rates coming out of the delivering well. Specifically, during Step 1 of the delivery sequence we found that setting the pressure so that the flow rate emerging at the Main Channel Flush input was seventy-five percent of the flow rate emerging from the well of interest minimized the flush channel interfering with the population delivery. For Well A8 setting the Main Channel Flush flow rate at sixty-five percent of the supposed well channel flow rate conferred a higher yield of worms than the seventy-five percent setting. Additionally, increasing the duration of Step 2 for this well by 0.5 seconds to clear a majority of the worms exiting the well from the Main Channel. For the timings used, pressures between ~69 and ~103 kPa (10-15 psi) at the gasket, along with the reduced factor pressure at the Main Channel Flush were sufficient adjustments in the sequence to achieve efficient delivery (FIG. 26, 10 psi: 81%±10 and 15 psi: 94%±2). These delivery rates were a considerable improvement over the performance of the 16 well device described above, where the range of delivery rates was ~80-93% when 20 psi was applied at the gasket and the Main Channel Flush reservoir. In fact, at ~103 kPa (15 psi) applied to the gasket and a Main Channel Flush, a nearly complete removal of the population from the well was observed in under 1 second (FIG. 27). These findings imply that the lower fluidic resistances and flow rate compensation mechanisms in the 64 well device setup result in far more consistent and efficient population delivery than what was achieved on the 16 well chip platform.

Preliminary tests showed that the established sequence timings were not sufficient to deliver measurable worm populations at ~35 kPa (5 psi) applied at the gasket. Step 1's time duration would have to be increased considerably to achieve valuable delivery rates at this pressure applied through the gasket. At the maximal pressure, applying ~138 kPa (20 psi) at the gasket caused leakage or "cross-talk" between flow from multiple wells, as the pressure was sufficient to overcome the valve sealing on-chip for a few of the wells. Since the 64-well device's flow layer channel height was nearly twice the height of the 16-well chip, the channel ceiling or "membrane" above the control layer was required to deform twice as much in the newer device. This channel height discrepancy could explain the improved sealing of the 16 well device's valves during the application of 20 psi at the gasket.

Experimental Validation of Population Segregation

To confirm that mixing between loaded populations in different wells of the device would not interfere with desired device operation, delivery sequence experiments were performed with multiple distinct strains loaded into the on-chip wells. Three separate populations where loaded into wells of the device illustrated in Panel A of FIG. 18. The populations were loaded in distinct orders along a given row (FIG. 28). The two strain preloading configurations allowed us to confirm whether or not there was cross-mixing of worms between wells in the given row. As mentioned earlier, each row within the device's well plate format reservoir array has the same motif of eight well channels with flow regulated by seven multiplexed valves. It was surmised that if mixing between the wells within a single row in the array were eliminated, particularly the row closest (row H) and the row farthest from the chip exit (row A), mixing between wells of any of the rows could be ruled out as a proof of concept. These rows contain the two extremes for two key worm delivery parameters: flow rates coming from wells within a given array column and the distance the worm populations must travel to reach the exit. Worms from wells in row A will be the least likely to reach the exit of the chip and be cleared from the main channel between deliveries from each well in the sequence with the optimized timing and pressure parameters.

Figure 28A:
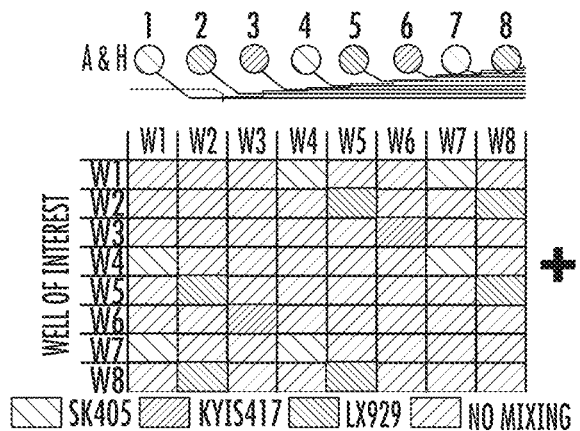
FIGS. 28A-28D illustrate the design of experiments used to test the ability of the device illustrated in Panel A of FIG. 18 to maintain population segregation between sample populations loaded in different sample reservoirs during delivery.
Figure 28B:
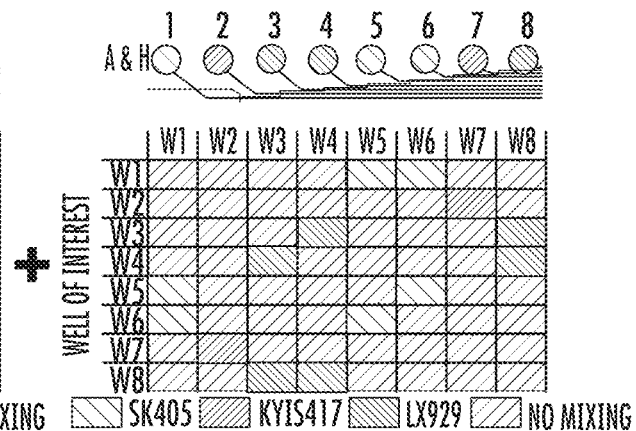
Figure 28C:
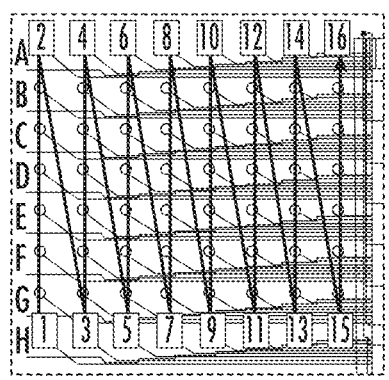
Figure 28D:
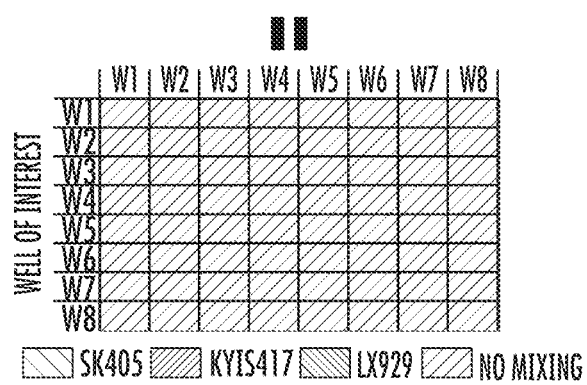

Three different strains were loaded and delivered in sequence according the configurations outlined in FIG. 28C. The figure shows a mixing truth table for the two configurations (FIGS. 28A, 28B, and 28D). Looking at a single well loading configuration, when a given strain is loaded into a subset of wells in the row, mixing between a given well of interest and wells that were preloaded with the same strain cannot be ruled out during the delivery sequence, even if the device is functioning properly. However, mixing between wells with different strains is easily confirmed, as indicated by the green mixing candidates. In FIG. 28D, the two loading configurations are compared and by overlapping their truth tables it is evident that all cases of mixing between wells in the rows are ruled out as long as only the strain preloaded in a given well is collected during the delivery sequence.

The sequence as outlined in FIG. 28C was run at ~103 kPa (15 psi) applied at the gasket. ~100 worms for each strain were preloaded in each well according to the configurations outlined in FIG. 28A, as well as 28B. Each configuration was run three times. In 91 out of 96 population deliveries from individual wells, zero cross-contamination of the wrong strain in a given well was observed. In the five cases in which any mixing was observed, the contaminating worms comprised on average <1.9%±0.6 of the total population delivered.

Additional experiments were performed to confirm that animals from row A were not contaminating animals from row H, since all wells belonging to the same column had the same strain pre-loaded into the them during the experiments outlined in FIG. 28 (e.g. well A3 and well H3 have the same strain). A distinct strain was preloaded in all wells in row A and a different strain was preloaded in the wells of row H. Tests were then performed that validated that there was no cross-contamination between the two rows during the delivery sequence.

The near elimination of cross-contamination between wells in the rows that were located at the device's two extremes in terms distance from the main exit was confirmed. Additional optimization of the delivery sequence can reduce cross-mixing to even more negligible levels, particularly increasing the duration of Step 2 by 0.1-0.5 sec when the Main Channel is being cleared of potential contaminating worms.

Materials and Methods

Device Fabrication

The microfluidic chip was fabricated using multilayered soft-lithography via techniques similar to methods established for the 16-well device described in the Examples above. In this case, the device molds were patterned on six-inch wafers as opposed to four inch wafers due to the larger device area. Using the fabrication methods described above, a control layer mold consisting of negative resist was patterned on one wafer and a flow layer mold consisting of negative and positive resist was patterned on the second wafer. The control layer thickness in this case was ~45 µm and the flow layer thickness was ~110 µm.

To create the 64 well plate-format reservoirs in the flow layer mold, first an 8×8 well section was cut from a conical 96 well PCR plate (Eppendorf Corp.) using a band saw. This piece was then cleaned by submersion in isopropyl alcohol and air-dried prior to applying of a drop of PDMS (10:1, elastomer: base agent) to the outer tip of each conical reservoir in the plate section. With the flow layer mold situated on a level hot plate, the PCR plate section was placed such that its conical wells sat on and aligned with the flow layer mold's population input ports (Panel A of FIG. 19). A hot plate set at 75° C. was used to cure the PDMS on the tips of conical wells and fix the PCR plate piece's location on the mold. After placing an acrylic barrier on top of the flow layer wafer mold, 90 grams of uncured PDMS (10:1, base agent: curing agent) was poured inside the perimeter of the barrier (Panel C of FIG. 19). The components were then placed in an oven at 72.5° C. for 3 hours to cure the PDMS.

The large area device was then bonded to its control layer via previously-described oxygen plasma treatment method. Due to the device's large area, optical alignment tools were used to properly position the flow layer relative to the control layer. Using two stereoscopes, the correct positioning of alignment markers on opposite sides of the device was confirmed before making the permanent bonding contact. A baking step was then performed, followed by bonding the device to 3 mm thick piece of custom-cut borosilicate glass.

Gasket System Fabrication

All components of the gasket system (FIG. 20) were machined via CNC or manual milling. The parts were fabricated so that the entire gasket system fit the footprint of standard well plates. A 12.5 mm thick acrylic part was machined to have multiple 2 mm×1 mm cross-section channels that terminated with 3 mm wide circular openings (FIG. 21A). A 3 mm thick acrylic part was then machined to fit flush against the larger piece described above. 3 mm holes were drilled into the acrylic part, such that the holes completely overlapped with the openings on the thicker acrylic part (FIG. 21A). Both parts were sandwiched between two 7×7 inch borosilicate glass sheets that were held in place by tightened screw clamps. The components were then placed in an oven at 70° C. for 30 min, followed by another 30 min bake at 145° C. The components were then placed back into an oven at 70° C. for 30 minutes, and then allowed to cool to room temperature.

The channels machined into the thick acrylic part were then sealed from the external environment except at the circular openings that overlapped with the equivalent features in the thinner part. Grooves were then machined around the entire circumference of each pneumatic output orifice. Rubber O-rings (Danco Inc.) were then secured into the inner edges of the grooves (FIGS. 21B-21C).

Figure 20A:
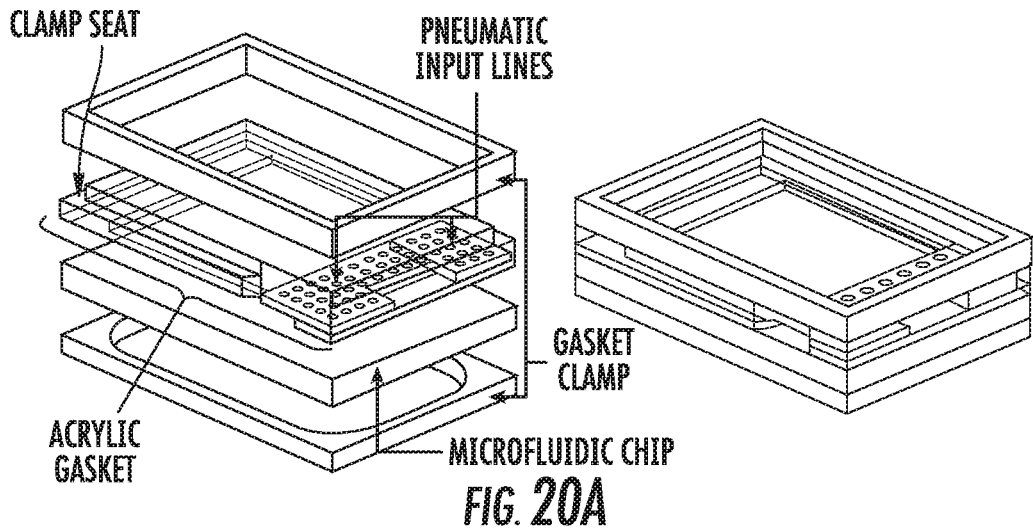
FIGS. 20A-20B illustrate the 64 sample well microfluidic device gasket system.
Figure 20B:
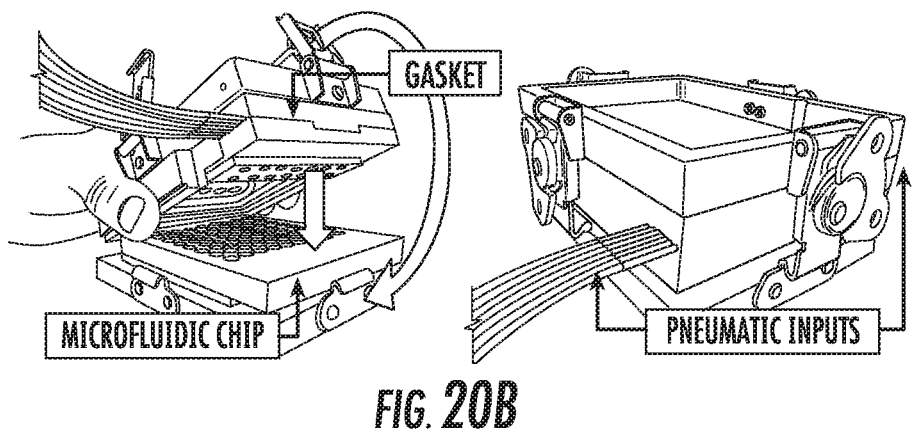

The pneumatic entrances for each air-input channel were machined into two of the short sides of the gasket (see FIG. 20 and FIG. 21A). A 5 mm×5 mm step was then machined on the top-side of the gasket for alignment of the gasket clamp (FIG. 20A). 17 gauge metallic couplers were then secured into these holes with adhesive for coupling to solenoid valves (FIG. 20B). Holes were then drilled through the entire thickness of the gasket where tubing from the flush lines would interface the microfluidic chip.

The gasket clamp was machined out of aluminum (a 12.5 mm thick piece and a 6.3 mm thick piece) (FIG. 20). Holes with screw threads were then drilled into the center of each of the four sides of the rectangular aluminum components of the clamp. Four twist latches (Fastenal Inc.) were secured to the perimeter of top aluminum part with screws. Corresponding latch hooks were screwed onto the four sides of the bottom aluminum piece of the gasket clamp, which would sit below the chip and the gasket.

Automation Software and Hardware Control

A set of twenty-one solenoid valves controlled by a custom automation program written in LabVIEW, regulated fluid flow in the multiplexer device by coupling pressurized fluid and air to the pneumatic inputs inside the gasket. Computer-controlled pressure regulators (QPV1, Proportion Air Inc.) controlled the dynamic pressure applied to the well plate format reservoir array and the Main Channel Flush's fluid reservoir.

Device Operation: Priming, Animal Loading, and Sequence Initiation

Tubing inputs for the Exit Flush, Main Channel Flush, and Main Exit (Panel B of FIG. 18) were plugged into the device via 22 gauge metal couplers (Instech Solomon). ~20 µL of filtered dionized water was loaded into each of the on-chip pneumatic microfluidic valve reservoirs (Panel C of FIG. 18). The chip and the acrylic gasket were then sandwiched and clamped together within the gasket clamp. 207 kPa (30 psi) was then delivered to each on-chip valve input via the gasket to fill the valve channels with DI water. After priming the valves, the Exit Flush delivered filtered M9 solution to the device to fill it with fluid and remove air bubbles. Valves one through eight (V1-V8, Panel C of FIG. 18) were then closed and ~70-105 kPa (~10-15 psi) was applied to the on-chip well plate reservoir array and the fluid coming into the chip via the Exit Flush input. The closed valves served as dead ends for fluid flow so that the pressurized fluid would force any air bubbles in the microchannels to diffuse through the bulk PDMS.

To load animals onto the chip after priming, a stand-alone pneumatic source, such as a syringe coupled to the "all-stop-valve" input (Panel A of FIG. 18) was pressurized to block flow out of the wells. After removing the chip from the gasket system, ~100-150 worms were then loaded via micropipette (P-200) coupled maximum recovery pipette tips into the desired wells and allowed to sink to the well bottoms (~5 min). Meanwhile, the chip was returned to the gasket system, and the on-chip valves were then pneumatically closed. At this point, the "all-stop-valve" was opened and the delivery sequence could commence.

Conclusions

A microfluidic multiplexer platform for ultra-fast delivery of *C. elegans* populations to optical interrogation systems was designed, fabricated, and characterized. The modular system consisted of a microfluidic chip with 64 wells for housing the distinct sample populations, and this chip interfaces with a gasket system that delivers pneumatic input to the on-chip valves and well plate format reservoirs. An "all-stop" valve that can be actuated without external pressurized input, blocks flow out of each population-housing reservoir, enabling sample loading at any location, and increases the chip's amenability with automated liquid handling systems.

The 64 well platform greatly improved upon the performance of the 16 well device in terms delivery efficiency and timing. All wells in the device were be able to deliver at least 92% of their preloaded population in fewer than 3 seconds, as opposed to the minimum of 80% in less than 4.7 seconds on the 16 well platform described above. This improvement in delivery consistency and efficiency could further reduce the time needed to perform large-scale high throughput screens. Furthermore, improving the sealing capabilities of multiplexed valves to avoid the cross-talk observed between wells at 20 psi applied at the gasket would further improve delivery efficiency. Increasing the length of the overlap regions between Valves 1-14 and the semicircular channels in the flow layer could improve the valves' sealing capabilities.

Increasing the duration of Steps 2 and/or 3 in the delivery sequence will most likely eliminate the negligible cross-contamination events observed during the population segregation validation experiments. Additionally, the higher applied pressures at the gasket enabled by improved valve sealing will lead to faster delivery during Step 1 of the sequence and decrease the likelihood that worms remain in the Main Channel.

The devices, systems, and methods of the appended claims are not limited in scope by the specific devices, systems, and methods described herein, which are intended as illustrations of a few aspects of the claims. Any devices, systems, and methods that are functionally equivalent are intended to fall within the scope of the claims. Various modifications of the devices, systems, and methods in addition to those shown and described herein are intended to fall within the scope of the appended claims. Further, while only certain representative devices, systems, and method steps disclosed herein are specifically described, other combinations of the devices, systems, and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated.

The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than where noted, all numbers expressing geometries, dimensions, and so forth used in the specification and claims are to be understood at the very least, and not as an attempt to limit the application of the doctrine of equivalents to the scope of the claims, to be construed in light of the number of significant digits and ordinary rounding approaches.

Unless defined otherwise, all technical and scientific terms used herein have the same meanings as commonly understood by one of skill in the art to which the disclosed invention belongs. Publications cited herein and the materials for which they are cited are specifically incorporated by reference.

What is claimed is:

1. A multiplexer microfluidic device comprising:
   (a) a main channel having a downstream end;
   (b) a plurality of sample reservoirs;
   (c) a plurality of inlet channels; and
   (d) a plurality of valves positioned along the inlet channels to regulate fluid flow through the inlet channels;
   wherein each inlet channel fluidly connects with the main channel to form an intersection;
   wherein each inlet channel fluidly connects a single sample reservoir to the main channel;
   wherein at least a first valve and a second valve are positioned along each fluid inlet channel to regulate fluid flow through the inlet channel, wherein the first valve and the second valve are independently operable, and wherein the first valve is positioned in proximity to the intersection of the inlet channel and the main channel; and
   wherein the plurality of valves in the device are configured such that operation of one or more of the plurality of valves selectively directs fluid flow through a predetermined inlet channel in the device; and
   wherein the downstream end of the main channel is structured to fluidly connect the main channel of the multiplexer multifluidic device to a sample processing element.

2. The device of claim 1, wherein the intersections of the inlet channels and the main channel are staggered.

3. The device of claim 1, further comprising signal processing circuitry or a processor configured to actuate one or more valves in a predetermined fashion to direct fluid flow through the microfluidic device.

4. The device of claim 1, further comprising a sample processing element fluidly connected to the downstream end of the main channel.

5. The device of claim 4, wherein the sample processing element comprises a device for optically interrogating a sample, a device for optically manipulating a sample, a device for physically manipulating a sample, or any combination thereof.

6. The device of claim 5, wherein the sample processing element comprises a microfluidic laser axotomy platform, a flow sorter machine, a white-light microscope, a fluorescence microscope, a confocal microscope, a two-photon microscope, a second harmonic generation microscope, a third harmonic generation microscope, an interference microscope, a microinjector, a device configured to perform laser surgery, a device configured to function as optical tweezers, a device configured to perform a photoconversion, a device configured to perform photo-bleaching, a device configured to conduct photo-polymerization, a device configured to perform optogenetics experiments, a device configured to perform an optoinjection, a device configured to phenotypically characterize organisms or cells, one or more electrodes configured to perform electrophysiological recording experiments, a magnetic device configured to interact with the sample, a spectrometers, mass spectrometers, gas chromatographs, or any combination thereof.

7. The device of claim 4, wherein the sample processing element comprises a sample processing element configured to individually process multicellular organisms which comprises:
   (a) a loading chamber fluidly connected to the main channel downstream from the inlet channels;
   (b) a staging chamber fluidly connected to the loading chamber to form an intersection;
   (c) a trapping chamber fluidly connected to the staging chamber to form an intersection;
   (d) a first valve positioned in proximity to the intersection of the loading chamber and the staging chamber to regulate fluid flow between the loading chamber and the staging chamber; and
   (e) a second valve positioned in proximity to the intersection of the staging chamber and the trapping chamber to regulate fluid flow between the staging chamber and the trapping chamber;
   wherein the height, width, and length of the staging chamber are selected in accordance with the dimensions of the multicellular organisms so as to permit only one of the multicellular organisms to be present within the staging chamber at a time, and
   wherein the first and second valves are configured such that sequential operation of the first valve and the second valve selectively directs a single organism first from the loading chamber into the staging chamber, and subsequently from the staging chamber into the trapping chamber.

8. The device of claim 7, further comprising one or more sieve structures fluidly connected to the loading chamber,
   wherein the sieve structures are fluidly connected to the loading chamber by fluid flow paths, each having a height, width, and length selected in accordance with the dimensions of the multicellular organisms, such that the multicellular organisms cannot pass through the fluid flow paths.

9. The device of claim 7, further comprising one or more sieve structures fluidly connected to the staging chamber, p1 wherein the sieve structures are fluidly connected to the staging chamber by fluid flow paths, each having a height, width, and length selected in accordance with the dimensions of the multicellular organisms, such that the multicellular organisms cannot pass through the fluid flow paths.

10. The device of claim 7, wherein the trapping chamber further comprises a plurality of protrusions extending from one side wall of the trapping chamber,
    wherein the protrusions are configured to physically restrict the multicellular organism within the trapping chamber.

11. The device of claim 10, wherein the protrusions extend from a side wall of the trapping chamber which further comprises a sieve structure,
    wherein the sieve structure is fluidly connected to the trapping chamber by fluid flow paths within the side wall, each having a height, width, and length selected in accordance with the dimensions of the multicellular organisms, such that the multicellular organisms cannot pass through the fluid flow paths, and
    wherein the fluid flow paths are configured to fluidly restrict the multicellular organism within the trapping chamber.

12. The device of claim 7, wherein the trapping chamber further comprises a valve configured to mechanically restrict a multicellular organism within the trapping chamber.

13. The device of claim 7, further comprising an exit area fluidly connected to the trapping chamber.

14. The device of claim 13, wherein the exit area comprises a first microfluidic channel and a second microfluidic channel and a first valve and a second valve,
    wherein the first valve is configured to control fluid flow through the first microfluidic channel, and
    wherein the second valve is configured to control fluid flow through the second microfluidic channel.

15. The device of claim 14 wherein the first valve and the second valve are configured to completely block fluid flow through the first microfluidic channel and the second microfluidic channel when the first valve and the second valve are in the closed position.

16. The device of claim 14, wherein the first valve and the second valve are 3-dimensional valves.

17. The device of claim 7, further comprising a device for optical interrogation configured to optically interrogate a multicellular organism within the trapping chamber.

18. The device of claim 1, further comprising a gasket system configured to pressurize one or more of the plurality of sample reservoirs.

* * * * *

UNITED STATES PATENT AND TRADEMARK OFFICE
CERTIFICATE OF CORRECTION

PATENT NO. : 11,192,109 B2
APPLICATION NO. : 16/038415
DATED : December 7, 2021
INVENTOR(S) : Adela Ben-Yakar et al.

Page 1 of 1

It is certified that error appears in the above-identified patent and that said Letters Patent is hereby corrected as shown below:

In the Claims

Claim 9, Column 76, Line 10, replace "connected to the staging chamber, p1" with --connected to the staging chamber,--.

Signed and Sealed this
Twenty-ninth Day of March, 2022

Drew Hirshfeld
*Performing the Functions and Duties of the*
*Under Secretary of Commerce for Intellectual Property and*
*Director of the United States Patent and Trademark Office*